US012788861B2

(12) United States Patent
Abdolahad et al.

(10) Patent No.: US 12,788,861 B2
(45) Date of Patent: Nov. 10, 2026

(54) DEACTIVATION OF CIRCULATING TUMOR CELLS (CTCs) IN THE BLOODSTREAM BY ELECTROSTATIC STIMULATION OF THE PERIPHERAL BLOOD

(71) Applicant: Mohammad Abdolahad, Tehran (IR)

(72) Inventors: Mohammad Abdolahad, Tehran (IR); Mohammad Reza Ghaderinia, Tehran (IR); Mohammad Ali Khayamian, Tehran (IR); Hamed Abadijoo, Tehran (IR); Shahriar shalileh, Tehran (IR)

(73) Assignee: Mandegar Advanced Medical Technologies Development Company (IR)

( * ) Notice: Subject to any disclaimer, the term of this patent is extended or adjusted under 35 U.S.C. 154(b) by 169 days.

(21) Appl. No.: 18/945,596

(22) Filed: Nov. 13, 2024

(65) Prior Publication Data

US 2025/0065027 A1 Feb. 27, 2025

Related U.S. Application Data

(63) Continuation of application No. 17/207,656, filed on Mar. 20, 2021, now Pat. No. 12,208,189.

(51) Int. Cl.
*A61M 1/36* (2006.01)
*A61N 1/40* (2006.01)

(52) U.S. Cl.
CPC ................. *A61M 1/36* (2013.01); *A61N 1/40* (2013.01)

(58) Field of Classification Search
CPC .................................. A61M 1/36; A61N 1/40
See application file for complete search history.

(56) References Cited

U.S. PATENT DOCUMENTS 12,208,189 B2 * 1/2025 Abdolahad .............. A61N 1/10
2017/0176414 A1 * 6/2017 Abdolahad ........ G01N 33/5011

* cited by examiner

*Primary Examiner* — Joseph M Dietrich

(57) ABSTRACT

A method for deactivating deactivating circulating cancer cells (CTCs). The method includes reducing viability of CTCs and/or destroying CTCs by applying a positive electrostatic field to bloodstream of a cancer patient.

18 Claims, 45 Drawing Sheets

1202

1204

1206

1208

2700

| Item | -PPECS | +PPECS |
|---|---|---|
| WBC (K/μL) | 5.5 ± 0.3 | 5.3 ± 0.5 |
| RBC (M/μL) | 4.7 ± 0.1 | 4.3 ± 0.3 |
| HGB (g/dL) | 14.9 ± 0.6 | 14.7 ± 0.4 |
| HCT (%) | 42.1 ± 1.4 | 41.2 ± 1.5 |
| MCV (fL) | 91.3 ± 3.5 | 87.7 ± 0.7 |
| MCH (pg) | 32.1 ± 0.2 | 30.6 ± 1 |
| MCHC (g/dL) | 33.25 ± 0.4 | 31 ± 0.5 |
| Platelets (K/μL) | 220 ± 30 | 203 ± 22 |
| RDW (%) | 11.8 ± 0.1 | 12 ± 0.4 |
| Neutrophils (%) | 59 ± 5 | 55 ± 2 |
| Lymphocytes (%) | 45 ± 5 | 42 ± 2 |
| Monocytes (%) | 2 ± 1 | 2 ± 1 |
| Eosinophils (%) | 2 ± 1 | 2 ± 1 |

FIG. 35

DEACTIVATION OF CIRCULATING TUMOR CELLS (CTCs) IN THE BLOODSTREAM BY ELECTROSTATIC STIMULATION OF THE PERIPHERAL BLOOD

CROSS-REFERENCE TO RELATED APPLICATION

This application is a continuation of patent application Ser. No. 17/207,656, filed Mar. 20, 2021, and entitled "DEACTIVATION OF CIRCULATING TUMOR CELLS (CTCs) IN THE BLOODSTREAM BY ELECTROSTATIC STIMULATION OF THE PERIPHERAL BLOOD", which is a continuation-in-part of U.S. patent application Ser. No. 17/063,689, filed Oct. 5, 2020, and entitled "INDUCING INTERNAL APOPTOSIS IN MALIGNANT TUMORS BY POSITIVE ELECTROSTATIC CHARGES", which is a continuation-in-part of U.S. patent application Ser. No. 16/027,315, filed Jul. 4, 2018, and entitled "INDUCING INTERNAL APOPTOSIS IN MALIGNANT TUMORS BY POSITIVE ELECTROSTATIC CHARGES", which takes priority from U.S. Provisional Patent Application Ser. No. 62/528,456, filed on Jul. 4, 2017, entitled "FIGHTING CANCER WITH THE POWER OF ELECTROSTATIC CHARGES AS NON-IONIZING RADIATION", which are all incorporated herein by reference in their entirety.

ACKNOWLEDGEMENT STATEMENT

Inventors would like to acknowledge University of Tehran, Tehran, Iran, for their sponsorship and assistance in a process of starting and developing of materials and supports for this application.

TECHNICAL FIELD

The present disclosure generally relates to cancer therapy, and particularly, to a device and method for destruction of metastatic tumors without any side effects using a positively electrical charged chip.

BACKGROUND OF THE INVENTION

Radiotherapy is one of the most desirable treatments of cancer because it induces a strong suppression to tumor growth and inhibits disease progression. The main disadvantage of radiotherapy, which is related to the risk of post radiation side effects, might be damage that occurs to organelles that are very close to the treated area. Even advanced guided radiotherapy methods such as intensity modulated radiotherapy (IMRT) and volumetric modulated arc therapy (VMAT) induce post radiation colitis and cardiac ischemia when applied in treating prostate and breast cancers, respectively.

The main mortality of cancer is due to the fact that malignant tumors are able to shed invasive cancer cells in lymphatic and circulatory systems. These cells, named circulating tumor cells (CTCs), play a major role in cancer metastases. As the abundance of CTCs is extremely rare in a blood sample of malignant patients (about 1-10 CTCs in 7 ml of blood), strong efforts have been made to design methods for highly efficient isolation and enumeration of CTCs from whole blood of cancer patients. Although a destruction of CTCs is more important than their detection, rare reports were published on in-vivo destruction of CTCs which all depended on detection of CTCs prior to destruction. Capturing the mesenchymal CTCs (MCTCs) is a fundamental challenge due to an absence of a selective biomarker (such as EPCAM for epithelial cells) for their targeting. Hence, free destruction of CTCs has not been achieved up to now.

Hence, there is a need for a device, system and method for cancer therapy, especially for treating malignant cancer without any post treated infections or side effects on normal (healthy) cells within a cancer-involving tissue. Additionally, there is a need for a method that is capable of selective tumor and cancer cells (e.g., CTCs) destruction without any effects on healthy regions. Therefore, applying non-ionizing radiation may be an appropriate alternative method for tumor destruction without any side effects on healthy areas. As low energy of such radiations suppresses their application, there is a need for any effective mechanism other than having high energy photons for probable use of low energy stimulations in cancer treatment.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for in-vivo deactivating circulating cancer cells (CTCs). The method may include deactivating CTCs by applying a positive electrostatic field to bloodstream of a cancer patient. In an exemplary embodiment, deactivating CTCs may include at least one of reducing viability of CTCs and destroying CTCs.

In an exemplary implementation, applying the positive electrostatic field to the bloodstream of the cancer patient may include accumulating positive electrostatic charges on an electrically conductive element by applying a positive electrostatic voltage in a range of 50 V to 50 kV to the electrically conductive element utilizing an electrostatic charge generator and exposing the bloodstream to the accumulated positive electrostatic charges by placing the electrically conductive element with the accumulated positive electrostatic charges thereon at a distance of less than 10 cm from a portion of the bloodstream. In an exemplary implementation, deactivating CTCs by applying the positive electrostatic field to the bloodstream of the cancer patient may be done over a daily time period in a range of 1 hour to 5 hours during at least three days.

In an exemplary implementation, deactivating CTCs by applying the positive electrostatic field to the bloodstream of the cancer patient may include circulating a portion of the bloodstream of the cancer patient's body inside a fluidic channel, placing the electrically conductive element on the fluidic channel containing the circulating portion of the bloodstream, accumulating positive electrostatic charges on the electrically conductive element by applying the positive electrostatic voltage to the electrically conductive element utilizing the electrostatic charge generator, and forming deactivated CTCs in the circulating portion of the bloodstream responsive to electrostatically stimulating of CTCs induced by the accumulated positive electrostatic charges.

In an exemplary implementation, circulating the portion of the bloodstream of the cancer patient's body inside the fluidic channel may include extracting the portion of the bloodstream of the cancer patient's body into the fluidic channel and re-injecting the portion of the bloodstream from the fluidic channel to the cancer patient's body. Where, extracting the portion of the bloodstream and re-injecting the portion of the bloodstream may be done continuously in a cycle.

In an exemplary embodiment, circulating the portion of the bloodstream of the cancer patient's body inside the fluidic channel may include circulating the portion of the bloodstream of the cancer patient's body inside a spiral u-shaped tube. In an exemplary implementation, circulating the portion of the bloodstream may include circulating the portion of the bloodstream at a flow rate in a range of 5 ml/min to 500 ml/min. In an exemplary embodiment, circulating the portion of the bloodstream may include extracting the portion of the bloodstream from the cancer patient's body utilizing a first peristaltic pump, passing the extracted portion of the bloodstream through the fluidic channel utilizing the first peristaltic pump, and transmitting the portion of the bloodstream from the fluidic channel to the cancer patient's body utilizing a second peristaltic pump.

In an exemplary embodiment, a flow rate of the portion of the bloodstream through each of the first peristaltic pump and the second peristaltic pump may be adjusted at a flow rate defined by:

Flow rate of bloodstream circulation (ml/min)=4× Weight of the cancer patient (Kg)

In an exemplary embodiment, placing the electrically conductive element on the fluidic channel may include placing at least one of an electrical conductive plate and an electrical conductive tape on the fluidic channel. In an exemplary embodiment, placing the electrically conductive element on the fluidic channel may include covering a layer of an electrically conductive material on at least one of an electrical insulator plate and an electrical insulator tape and placing the at least one of the electrical insulator plate and the electrical insulator tape with the covered layer of the electrically conductive material thereon on the fluidic channel.

In another exemplary implementation of the method, deactivating CTCs by applying the positive electrostatic field to the bloodstream of the cancer patient may include placing the electrically conductive element over skin of the cancer patient at a location of a superficial vein of the cancer patient, accumulating positive electrostatic charges on the electrically conductive element by applying the positive electrostatic voltage to the electrically conductive element utilizing the electrostatic charge generator, and forming deactivated CTCs in the bloodstream of the cancer patient responsive to electrostatically stimulating of CTCs induced by the accumulated positive electrostatic charges.

In an exemplary embodiment, placing the electrically conductive element over skin of the cancer patient may include placing a layer of an electrically conductive material over skin of the cancer patient. In an exemplary embodiment, placing the electrically conductive element over skin of the cancer patient may include forming the electrically conductive element by attaching the layer of the electrically conductive material on a substrate and placing the formed electrically conductive element over skin of the cancer patient.

In an exemplary embodiment, attaching the layer of the electrically conductive material on the substrate may include attaching the layer of the electrically conductive material on a layer of an electrical insulator material. In an exemplary embodiment, attaching the layer of the electrically conductive material on the substrate may include attaching a layer of electrically conductive nanostructures on the substrate. In an exemplary embodiment, attaching the layer of the electrically conductive material on the substrate may include attaching a layer of at least one of carbon nanotubes (CNTs), vertically aligned multi-walled carbon nanotube (VAMWCNTs), graphene, zinc dioxide (ZnO), Silicon nanowires (SiNWs), Silicon nanograss, $TiO_2$ nanotubes, $TiO_2$ nanowires, metallic layers and combinations thereof on the substrate.

In an exemplary embodiment, attaching the layer of the electrically conductive material on the substrate may include attaching the layer of the electrically conductive material on a three-layer substrate. In an exemplary embodiment, the three-layer substrate may include a layer of silicon (Si), a layer of silicon dioxide ($SiO_2$) grown on the layer of silicon, and a catalyst layer deposited on the layer of $SiO_2$. In an exemplary embodiment, the catalyst layer may be configured to grow the layer of electrically conductive nanostructures thereon.

BRIEF DESCRIPTION OF DRAWINGS

The drawing figures depict one or more implementations in accord with the present teachings, by way of example only, not by way of limitation. In the figures, like reference numerals refer to the same or similar elements.

FIG. 35 shows complete blood count analysis of blood for −/+PPECS groups, consistent with one or more exemplary embodiments of the present disclosure.

DETAILED DESCRIPTION

Figure 1:
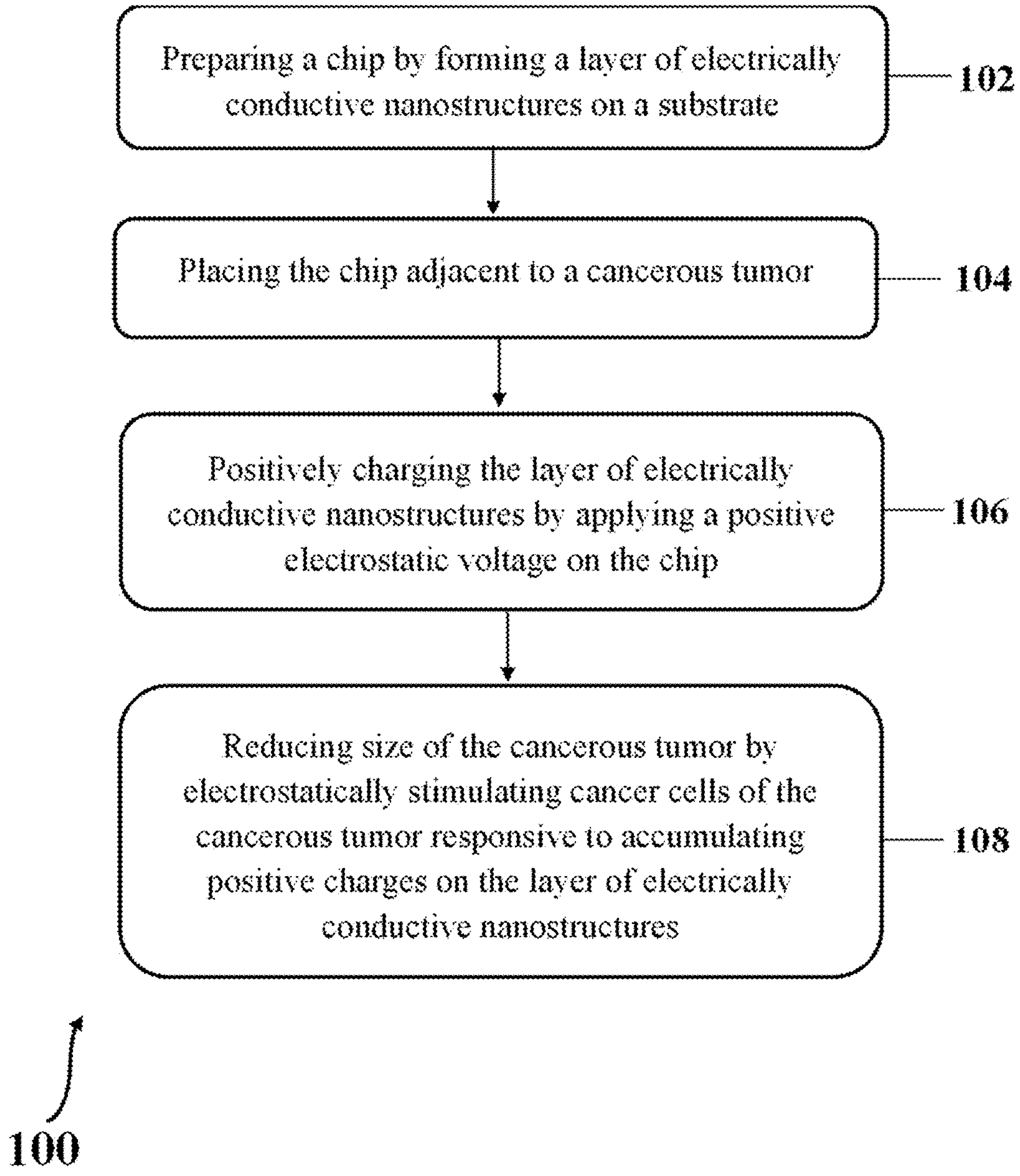
FIG. 1 illustrates an exemplary implementation of a method for tumor suppression, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Ionizing radiation plays a proven role in destruction of malignancies. Known doses of such radiation can play a critical role in cell death and mitotic arrest. However, therapeutic exposure can lead to damage and irreversible side effects for non-malignant surrounding tissues. Therefore, counteracting this process by a more safe and effective radiation is crucial. Ionizing radiation can damage cells in two different ways: directly by interacting with critical cellular targets or indirectly by generating free radicals.

Cancer cells respond to external chemical, mechanical or electrical stimulations differently from normal cells due to their non-regulated pathways in response to such external stimulations in comparison with normal cells' behavior. In exemplary embodiments of the present disclosure, it is shown that positive electrostatic charges (as a non-ionizing agent) causes cancerous/malignant tumor growth inhibition through tendency of cancerous/malignant cells to attract to positive charges or positively charged areas because of their negatively charged membrane and non-regulated proliferation pathways. This induces negative effects on the adhesion of malignant cells to the scaffold of the extracellular matrix in tissue followed by internal apoptosis in malignant cells.

Losing the attachment of malignant cells to the substrate or extracellular matrix (ECM) under the induction of positive electrostatic charges is the utilized mechanism in exemplary embodiments to electrostatically induce selective tumor killing. Regulated signaling pathways activated in normal cells do not permit them to be detached from the ECM in the response to non-programmed external electrostatic stimulation, as the internal apoptotic pathways are investigated for both normal and malignant cells.

Herein, an exemplary therapeutic procedure based on positive electrostatic charges named as electrostatic therapy (ET), as non-ionizing agent in cancer therapy is disclosed. The comparative attraction of normal and malignant cells (as electrically charged biological systems) to a float source of positive electrostatic charges produced and accumulated on an array of nanostructures may be illustrated by cells' vital pathways as well as cytoskeletal assemblies in post stimulated states. Attraction of malignant cells to the highly dense source of positive charges would diminish their adhesion to the substrate and activate internal apoptotic pathways through their degraded attachment to extra cellular matrix. In exemplary embodiments, unlike malignant cells, no functional response of normal cells to positive electrostatic stimulations, applied near a tissue, would be observed due to following regulative cellular proliferative pathways. This may be effective in selective treatment of malignant region without any side effects on normal tissues in cancerous patients. Simple handling by attachment of a charged patch without any hospitalization enables all day treatment without any thermal production or side effects to normal regions, making this exemplary method an improvement over all other radiative therapeutic methods.

It is worth noting that the exemplary method is completely different from tumor treating stimulations (TTF) in mechanism, because no destructive effect is observed on exposed malignant cells to positive electrostatic charges utilizing the exemplary method, meanwhile in TTF, a total alternative stimulation (150-200 kHz) independent from the negative or positive polarity is applied on cancer cells and their mitotic activity in metaphase gets disrupted. Moreover, the therapeutic period for complete elimination of a malignant tumor with an exemplary size of about 400 $mm^3$ in ET, utilizing exemplary methods, is less than one week but treatment by TTF has been designed in a long-time manner to prevent non-desired thermal production and skin irradiation. While no electromagnetic energy or flux would be transferred to the body or exposed tissue in ET, at least a temperature increment to about 41° C. has been reported beneath the electrodes of TTF.

Furthermore, potential clinical applications of ET may not require compliance of dose dependent treatment or avoiding from exposing the normal region as much as possible. In addition, this exemplary method may be locally applied to unrespectable tumors via interventional procedures, to stop micrometastases in confined spaces (for example, peritoncal seeds) or to treat tumor resection margins at the end of a tumor surgery.

FIG. 1 shows an exemplary implementation of method 100 for tumor suppression, consistent with one or more exemplary embodiments of the present disclosure. Exemplary method 100 may include preparing a chip by forming a layer of electrically conductive nanostructures on a substrate (step 102), placing the chip adjacent to a cancerous tumor (step 104), positively charging the layer of electrically conductive nanostructures by applying a positive electrostatic voltage on the chip (step 106), and reducing size of the cancerous tumor by electrostatically stimulating cancer cells of the cancerous tumor responsive to accumulating positive charges on the layer of electrically conductive nanostructures (step 108).

Figure 2A:
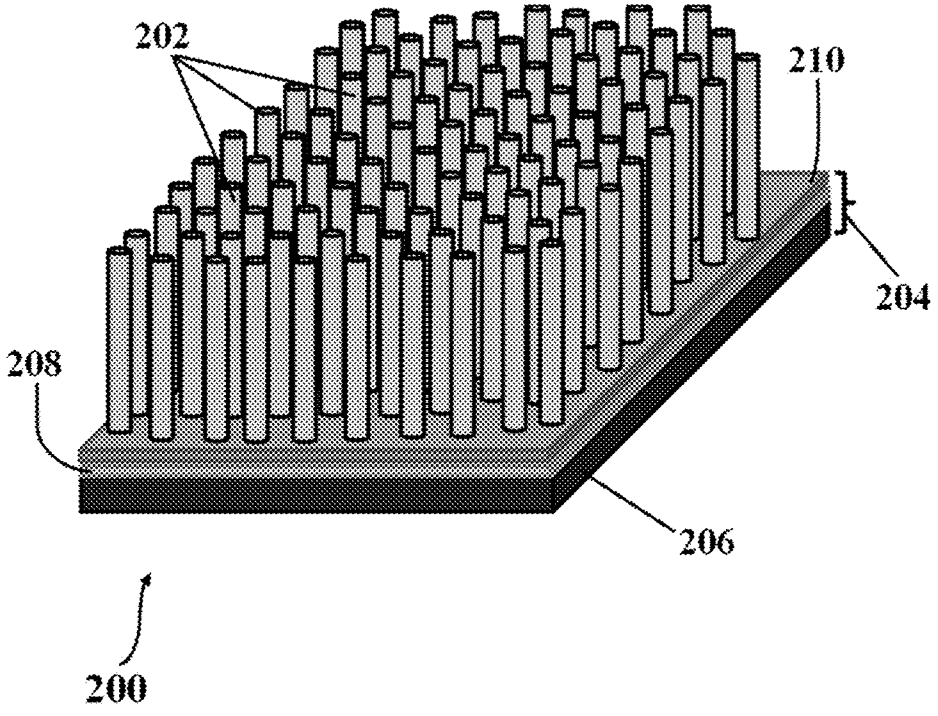
FIG. 2A illustrates a schematic view of an implementation of exemplary chip, consistent with one or more exemplary embodiments of the present disclosure.

Step 102 may include preparing the chip. FIG. 2A shows a schematic view of an implementation of exemplary chip 200, consistent with one or more exemplary embodiments of the present disclosure. Exemplary chip 200 may include a layer of electrically conductive nanostructures, for example, a layer (or an array) of electrically conductive nanotubes 202 that may be formed on exemplary substrate 204 that may include a silicon wafer 206.

In an exemplary implementation, exemplary chip 200 may include exemplary substrate layer 204 that may include a three-layer structure, including a layer of silicon (Si) 206, a layer of silicon dioxide ($SiO_2$) 208 grown on the layer of silicon, and a catalyst layer 210 deposited on the layer of $SiO_2$ 208. Exemplary chip 200 may further include an array of electrically conductive nanostructures, for example, the layer of electrically conductive nanotubes 202 grown on the catalyst layer 210. In an exemplary embodiment, the array of electrically conductive nanotubes 202 may include an array of carbon nanotubes (CNTs) grown on exemplary catalyst layer 210 that may include a layer of Nickel (Ni).

Figure 2B:
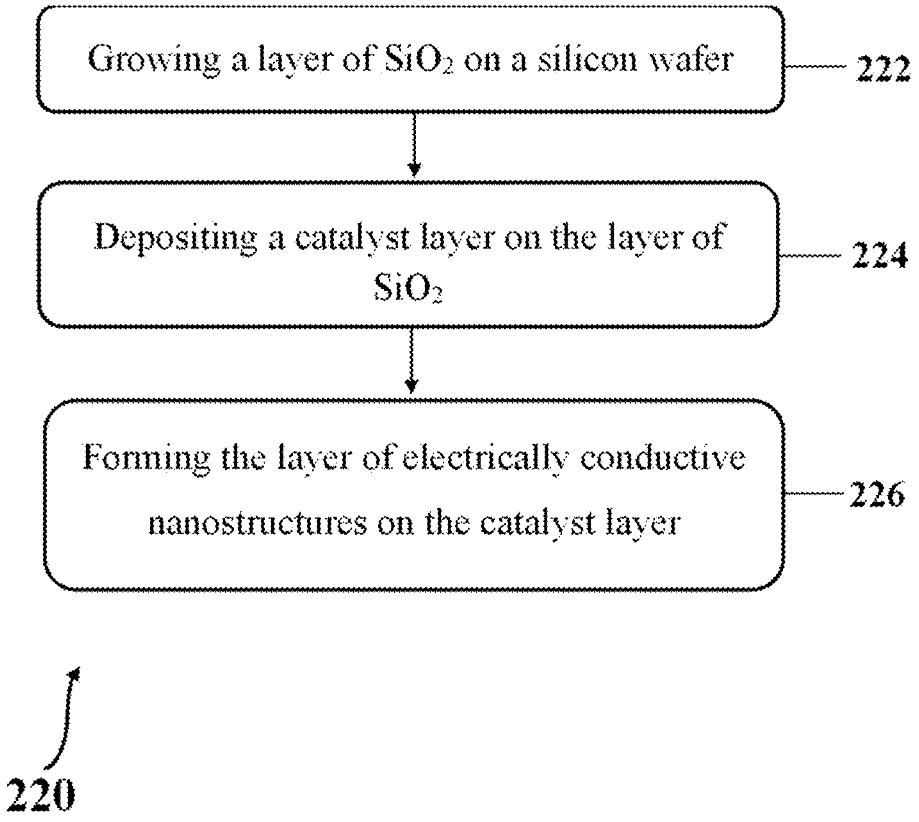
FIG. 2B illustrates an exemplary process for forming the layer of exemplary electrically conductive nanostructures on exemplary substrate, consistent with one or more exemplary embodiments of the present disclosure.

In an exemplary implementation, preparing exemplary chip 200 by forming the layer of the electrically conductive nanostructures, for example, the layer of electrically conductive nanotubes 202 on exemplary substrate 204 may include an exemplary process 220. FIG. 2B shows exemplary process 220 for forming the layer of exemplary electrically conductive nanostructures 202 on exemplary substrate 204, consistent with one or more exemplary embodiments of the present disclosure. Forming the layer of exemplary electrically conductive nanostructures 202 on exemplary substrate 204 (process 220) may include growing an exemplary layer of $SiO_2$ 208 on exemplary silicon wafer 206 (step 222), depositing exemplary catalyst layer on the layer of $SiO_2$ 208 (step 224), and forming the layer of exemplary electrically conductive nanostructures 202 on exemplary catalyst layer 210 (step 226). In an exemplary embodiment, forming the layer of exemplary electrically conductive nanostructures 202 on exemplary catalyst layer 210 may include growing a plurality of exemplary electrically conductive nanostructures 202 or an array of exemplary electrically conductive nanostructures 202 on exemplary catalyst layer 210.

In an exemplary embodiment, the layer of the electrically conductive nanostructures may include a layer of at least one of carbon nanotubes (CNTs), vertically aligned multi-walled carbon nanotube (VAMWCNTs), graphene, zinc dioxide (ZnO), Silicon nanowires (SiNWs), Silicon nanograss, $TiO_2$ nanotubes, $TiO_2$ nanowires, metallic layers, nanostructured metallic layers, and combinations thereof.

In an exemplary embodiment, layer of electrically conductive nanotubes 202 may include an array of CNTs, for example, an array of VAMWCNTs. VAMWCNT structures may be approved to be perfect charge accumulators, so an array of CNTs may be applied on exemplary chip 200 to produce a strong and dense electrostatic source on exemplary chip 200 via a direct current (DC) power generator, for example, using a battery.

Step 104 may include placing exemplary chip 200 adjacent to a cancerous tumor. In an exemplary implementation, placing exemplary chip 200 adjacent to the cancerous tumor may include placing exemplary chip 200 in a position located at a distance less than about 10 cm from the cancerous tumor. For example, exemplary chip 200 may be located on top of a part of a patient's skin, which may be close to the cancerous tumor which may be on the skin or inside the patient's body. In another example, exemplary chip 200 may be mounted on a bracelet or belt that may be placed or located around an area of the patient's body close to the location of the cancerous tumor.

In an exemplary embodiment, the cancerous tumor may include a tumor caused by a cancer, which may include a plurality of cancer cells. In an exemplary embodiment, the cancerous tumor may include a malignant metastatic tumor including a plurality of malignant cells, which may be a type of cancer cells. The cancerous tumor may include a tumor caused by breast cancer, skin cancer, bladder cancer, eye cancer, prostate cancer, etc. The cancerous tumor may be located at a location near a part of skin.

In an exemplary implementation, exemplary chip 200 may be adhered onto an external part of the skin near the location of the cancerous tumor. For example, exemplary chip 200 may be embedded within a patch that may be adhered onto the patient's skin while an electrical insulator layer may be placed between the patch and the patient's skin in order to prevent current flow between the patch and the body.

In an exemplary implementation, placing the chip adjacent to the cancerous tumor (step 104) may include forming an electrically conductive patch by attaching exemplary chip 200 onto an adhesive substrate, attaching the electrically conductive patch onto skin of a patient at a location adjacent, nearby or corresponding to the location of the cancerous tumor, and filling the interfacial area between the electrically conductive patch and the skin of the patient with a biocompatible electrical insulator layer. In an exemplary embodiment, the biocompatible electrical insulator layer may include Polydimethylsiloxane (PDMS).

In an exemplary implementation, electrically conductive patch including exemplary chip 200 may be covered by a biocompatible electrical insulator layer from the nanostructures side and may be located on top of a part of skin associated, corresponding, nearby or adjacent to the tumor region. The electrically conductive patch may be fixed on the skin by an anti-allergic tape.

Step 106 may include positively charging the layer of electrically conductive nanostructures by applying a positive electrostatic voltage on exemplary chip 200. Applying a positive electrostatic voltage on exemplary chip 200 may lead to accumulating positive charges on the layer of electrically conductive nanostructures. In an exemplary embodiment, positively charging the layer of electrically conductive nanostructures may include applying a positive electrostatic voltage on exemplary chip 200; thereby, resulting in accumulating positive charges on tips of exemplary electrically conductive nanotubes 202, for example, an exemplary array of CNTs.

In an exemplary implementation, positively charging the layer of electrically conductive nanostructures by applying the positive electrostatic voltage on exemplary chip 200 may include connecting exemplary chip 200 to a DC power generator or a vanograph generator, and applying a positive DC voltage in a range of about 10 V to about 70 V on the chip.

Figure 3:
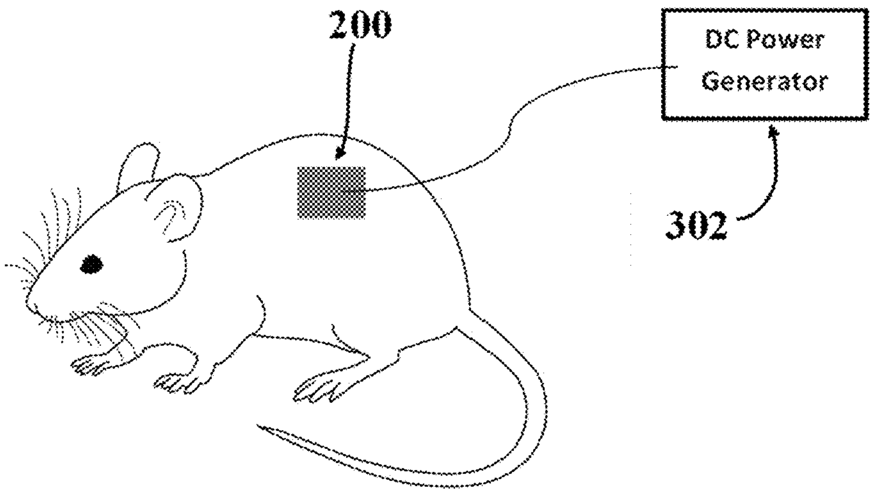
FIG. 3 illustrates a schematic implementation of connecting an exemplary chip, that may be fixed on a part of skin of a patient's body, to a DC power generator, consistent with one or more exemplary embodiments of the present disclosure.

FIG. 3 shows a schematic implementation of connecting an exemplary chip 200, that may be fixed on a part of skin of a patient's body, for example, a mouse, to a DC power generator 302 (or a vanograph generator), consistent with one or more exemplary embodiments of the present disclosure. A positive DC voltage of less than about 100 V may be applied onto exemplary chip 200 leading a dense amount of positive charges to be accumulated on the layer of electrically conductive nanostructures.

Step 108 may include reducing size of the cancerous tumor by electrostatically stimulating cancer cells of the cancerous tumor responsive to accumulating positive charges on the layer of electrically conductive nanostructures. The layer of electrically conductive nanostructures which may be placed adjacent to the cancerous tumor in step 104 and positively charged in step 106 may induce an electrostatic stimulation on the cancer cells which may have a strong negative charge. So, the electrostatically stimulating cancer cells of the cancerous tumor may include an internal apoptosis of the cancer cells in the cancerous tumor that may be induced by positive charges accumulated on the layer of electrically conductive nanostructures.

In an exemplary implementation, reducing size of the cancerous tumor may include a reduction in the size of the cancerous tumor by at least more than about 30%. In one example, reducing size of the cancerous tumor may include complete destruction and elimination of the cancerous tumor.

In an exemplary implementation, electrostatically stimulating cancer cells of the cancerous tumor may include internal apoptosis of the cancer cells in the cancerous tumor. The internal apoptosis of the cancer cells may be induced by positive charges accumulated on the layer of electrically conductive nanostructures due to a negative charge of the cancer cells. In an exemplary embodiment, electrostatically stimulating cancer cells of the cancerous tumor may include no stimulation of healthy (normal) cells due to a low negative charge of healthy (normal) cells. Moreover, electrostatically stimulating cancer cells of the cancerous tumor may include no stimulation of healthy (normal) cells placed either within the cancerous tumor or nearby areas of the cancerous tumor in a patient's body.

In an exemplary implementation, positively charging the layer of electrically conductive nanostructures by applying the positive electrostatic voltage on the chip (step 106), and reducing size of the cancerous tumor by electrostatically stimulating of cancer cells of the cancerous tumor responsive to accumulating positive charges on the layer of electrically conductive nanostructures (step 108) may be done in few days, for example, less than one week.

Various exemplary methods, systems, and devices are disclosed, and examples may include methods, systems, and devices for tumor suppression based on inducing internal apoptosis in cancer cells by positive electrostatic charges. Such tumor suppression caused by inducing internal apoptosis in cancer cells utilizing positive electrostatic charges may be referred to as an electrostatic therapy (ET) here. Exemplary methods may include accumulating positive electrostatic charges near cancer cells of a cancerous tumor; thereby, inducing apoptosis in cancer cells and complete destruction of the cancerous tumor. In one implementation, method 100 has been described above as an exemplary method for tumor suppression. In another general aspect, the present disclosure may be directed to an exemplary system for inducing apoptosis in cancer cells via electrostatically stimulating cancer cells by positive electrostatic charges. Exemplary systems consistent with the present disclosure may be utilized by exemplary methods described herein for electrostatically stimulating cancer cells; thereby, resulting in tumor suppression.

Figure 19A:
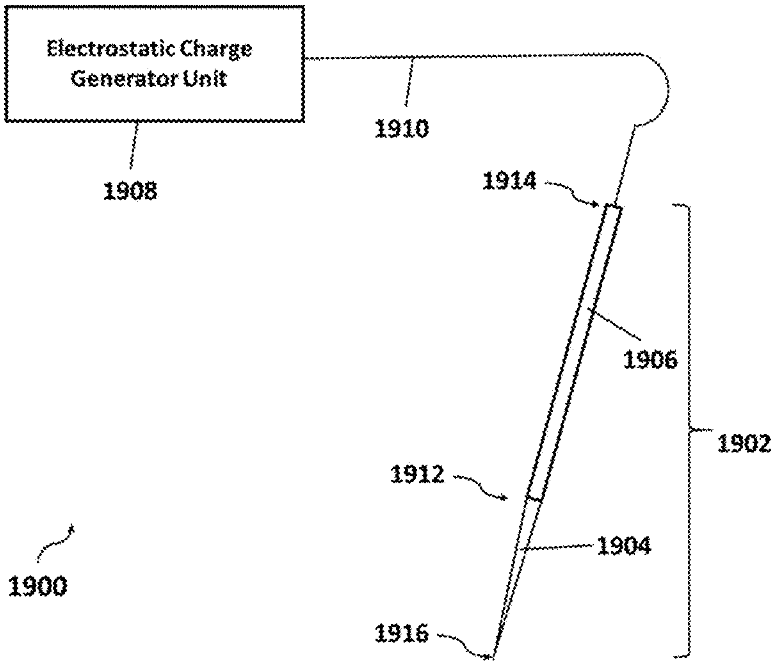
FIG. 19A illustrates a schematic view of an implementation of an exemplary system for tumor suppression, consistent with one or more exemplary embodiments of the present disclosure.

FIG. 19A shows a schematic view of an implementation of exemplary system 1900 for tumor suppression, consistent with one or more exemplary embodiments of the present disclosure. Exemplary system 1900 may include a wire 1902, an electrostatic charge generator 1908, and an electrical connector 1910. In an exemplary embodiment, wire 1902 may include an active part 1904 located at a first end 1912 of wire 1902 and an electrically passivated part 1906. In an exemplary embodiment, active part 1904 may be configured to be inserted into a cancerous tumor, accumulate positive electrostatic charges thereon, and inject accumulated positive electrostatic charges to cancer cells of the cancerous tumor. In an exemplary embodiment, electrically passivated part 1906 may include a remaining part of wire 1902 apart from active part 1904 of wire 1902. In an exemplary embodiment, electrically passivated part 1906 may include a second end 1914 of wire 1902. In an exemplary embodiment, electrostatic charge generator 1908 may be configured to accumulate positive electrostatic charges on active part 1904 by applying a positive electrostatic voltage in a range of about 1 kV to about 30 kV to wire 1902. In an exemplary embodiment, electrical connector 1910 may be configured to connect the second end 1914 of wire 1902 to electrostatic charge generator 1908. In an exemplary embodiment, electrostatic charge generator 1908 may include a Van de Graaff generator.

In an exemplary embodiment, wire 1902 may comprise a biocompatible electrically conductive wire. In an exemplary embodiment, wire 1902 may comprise a biocompatible electrically conductive wire that may be made of at least one of an alloy of titanium-nickel (Ti—Ni), an alloy of titanium-nickel-tantalum (Ti—Ni—Ta), stainless steel, platinum (Pt), an alloy of platinum-iridium (Pt—Ir), an alloy including gold (gold alloys), an alloy of cobalt-chromium (Co—Cr), an alloy of nickel-chromium (Ni—Cr), and combinations thereof.

In an exemplary embodiment, wire 1902 may include a wire with a thickness between about 1 mm and about 5 mm. In an exemplary embodiment, active part 1904 may include a tip of wire 1902 with a length between about 1 mm and about 20 cm of wire 1902 at the first end 1912 of wire 1902. The length of active part 1904 may depend on size of the cancerous tumor that may be in a range between about 1 mm and about 20 cm or more. In addition, length of wire 1902, The length of active part 1904 and length of electrically passivated part 1906 may depend on a depth of the cancerous tumor in a patient' body and the size of the cancerous tumor.

In detail, active part 1904 of wire 1902 may include various shapes and implementations that may depend on a location of a cancerous tumor and a procedure of inserting active part 1904 into the cancerous tumor. In an exemplary embodiment, active part 1904 of wire 1902 may be configured to be inserted into a cancerous tumor through skin. In an exemplary embodiment, the cancerous tumor may be located near skin. In an exemplary embodiment, active part 1904 of wire 1902 may include a sharp tip 1916 as shown in FIG. 19A. In an exemplary embodiment, active part 1904 of wire 1902 may include a needle-shaped tip of wire 1902 at the first end 1912 of wire 1902. In an exemplary embodiment, cancerous tumors located near skin may include superficial tumors, for example, intra-dermal tumors, gastrointestinal tumors, and breast tumors.

In a first scenario, entire outer surface of wire 1902 may be electrically insulated. Accordingly, electrically passivated part 1906 of wire 1902 and active part 1904 of wire 1902 may be covered with an electrical insulator layer. In an exemplary embodiment, sharp tip 1916 of active part 1904 may be remained open (or bare) in order to accumulate electrostatic charges thereon. In a second scenario, active part 1904 of wire 1902 may not be covered with the electrical insulator layer while electrically passivated part 1906 of wire 1902 may be covered with an electrical insulator layer. In an exemplary embodiment, parts of wire 1902, which may be in contact with surrounding tissues (peripheral tissues, i.e., non-cancerous peripheral tissues) of the cancerous tumor, may be covered with the electrical insulator layer. In a third scenario, parts of wire 1902, which may be in contact with the cancerous tumor, may be either covered with the electrical insulator layer or not. In an exemplary embodiment, the electrical insulator layer may include a biocompatible electrical insulator layer.

Figure 19B:
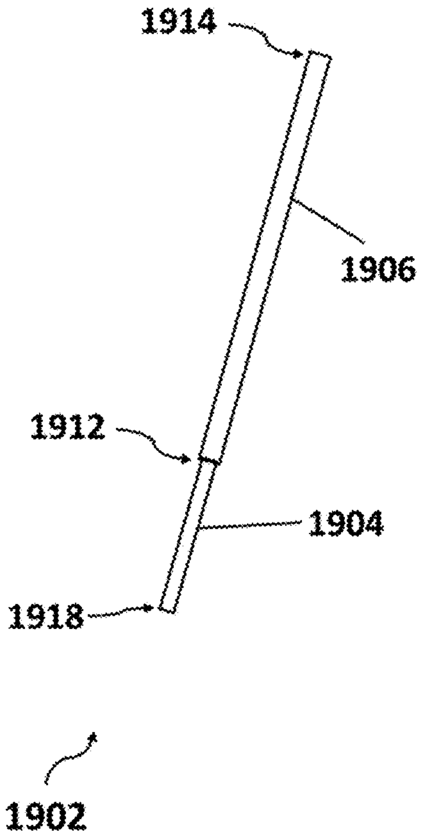
FIG. 19B illustrates a schematic view of an exemplary wire with a flat tip, consistent with one or more exemplary embodiments of the present disclosure.

In an exemplary embodiment, active part 1904 of wire 1902 may be configured to be inserted into the cancerous tumor during a low-invasive surgery. In such embodiments, active part 1904 of wire 1902 may include a flat tip at the first end 1912 of wire 1902. FIG. 19B shows a schematic view of exemplary wire 1902 with flat tip 1918, consistent with one or more exemplary embodiments of the present disclosure. Exemplary wire 1902 with flat tip 1918 may be configured to be inserted into a deep-seated cancerous tumor during a low-invasive surgery. In an exemplary embodiment, the low-invasive surgery may include at least one of a laparoscopy surgery, a robotic-based surgery, and combinations thereof. In an exemplary embodiment, the deep-seated cancerous tumor may include tumors of at least one of liver involved with a metastatic cancer, Hepatocellular carcinoma (HCC), Cholangiocarcinoma, cancers in deep-seated organs, and combinations thereof.

In an exemplary embodiment, wire 1902 may include a cancerous tumor localization guide wire. The cancerous tumor localization guide wire may include a wire that may be utilized in wire-guided localization technique for localizing cancerous tumors. In such embodiments, wire 1902 may include a wire with a thickness (or diameter) between about 1 mm and about 5 mm, which may include a commercial localization guide wire.

Figure 19C:
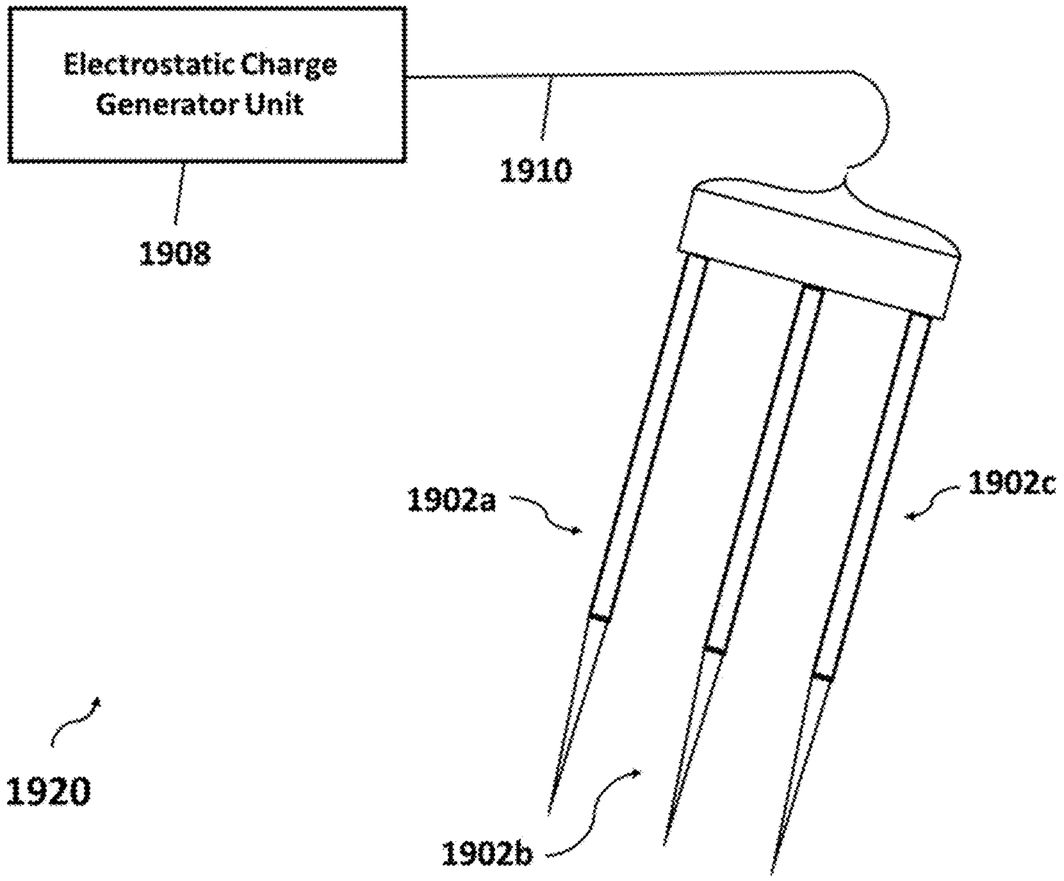
FIG. 19C illustrates a schematic view of another implementation of an exemplary system for tumor suppression, consistent with one or more exemplary embodiments of the present disclosure.

In an exemplary embodiment, more than one exemplary wire similar to wire 1902 may be utilized by an exemplary system similar to system 1900 for tumor suppression of large tumors. FIG. 19C shows a schematic view of another implementation of exemplary system 1920 for tumor suppression, consistent with one or more exemplary embodiments of the present disclosure. Exemplary system 1900 may include three exemplary wires 1902*a*-1902*c*, where each respective wire of wires 1902*a*-1902*c* may be similar to exemplary wire 1902 of FIG. 19A. Additionally, exemplary system 1920 may further include electrostatic charge generator 1908, and electrical connector 1910 similar to exemplary system 1900 of FIG. 19A. In an exemplary embodiment, a distance between each two exemplary wires of wires 1902*a*-1902*c* may depend on the positive electrostatic voltage that may be applied to wires 1902*a*-1902*c* by electrostatic charge generator 1908. In an exemplary embodiment, the distance between each two exemplary wires of wires 1902*a*-1902*c* may be about 3 cm if a positive electrostatic voltage of about 1 kV to be applied to wires 1902*a*-1902*c*. In another exemplary embodiment, the distance between each two exemplary wires of wires 1902*a*-1902*c* may be about 5 cm if a positive electrostatic voltage of about 30 kV to be applied to wires 1902*a*-1902*c*.

Figure 20:
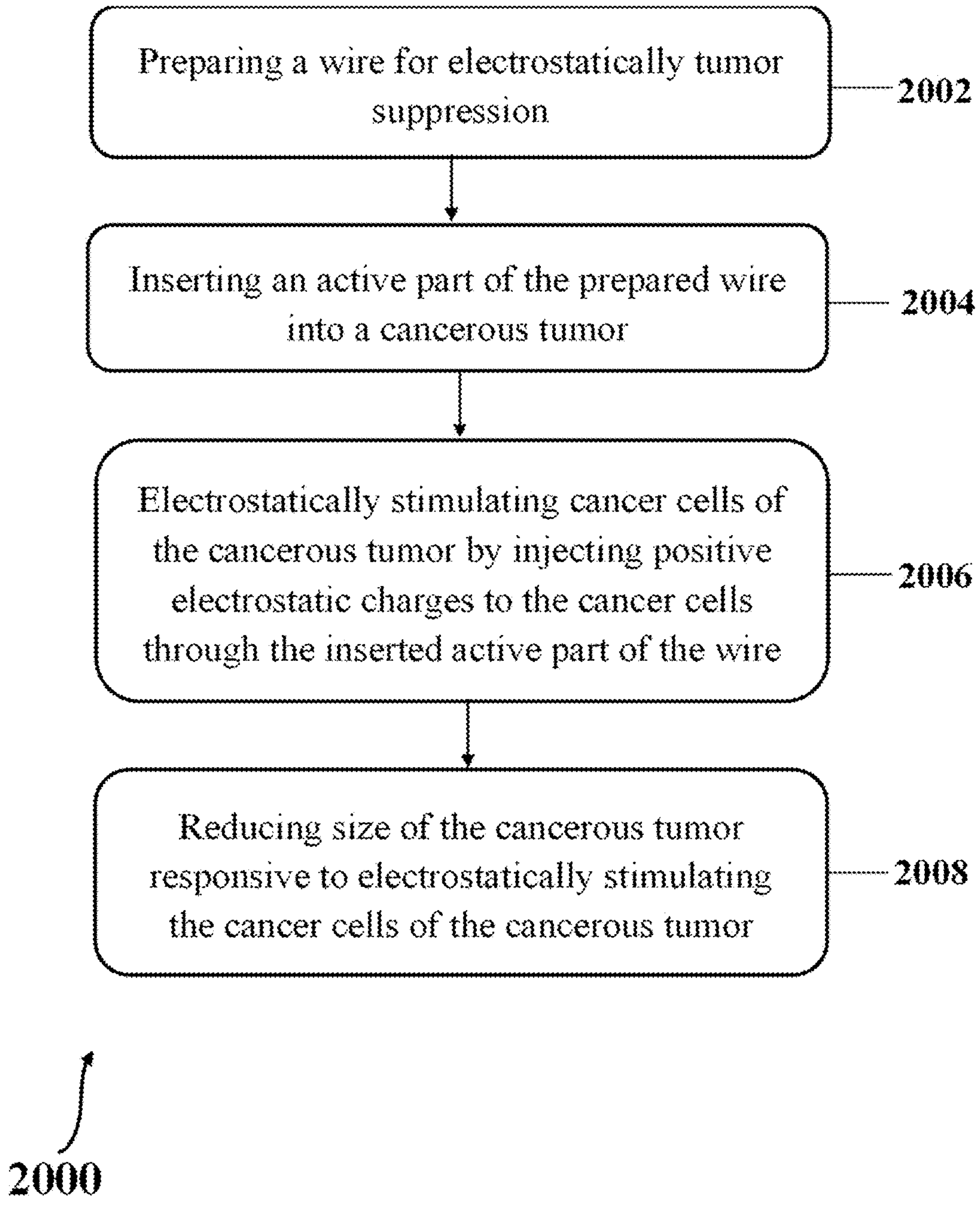
FIG. 20 illustrates an exemplary implementation of an exemplary method for tumor suppression, consistent with one or more exemplary embodiments of the present disclosure.

In another aspect of the present disclosure, an exemplary method for tumor suppression is disclosed. FIG. 20 shows an exemplary implementation of method 2000 for tumor suppression, consistent with one or more exemplary embodiments of the present disclosure. In an exemplary implementation, exemplary method 2000 may utilize exemplary systems 1900 or 1920 for tumor suppression. In an exemplary implementation, method 2000 may include inserting active part 1904 of wire 1902 (or at least one of wires 1902*a*, 1902*b*, and 1902*c*, and combinations thereof) into a cancerous tumor (step 2004), electrostatically stimulating cancer cells of the cancerous tumor by injecting positive electrostatic charges to the cancer cells through wire 1902 (or at least one of wires 1902*a*, 1902*b*, and 1902*c*, and combinations thereof) (step 2006), and reducing size of the cancerous tumor responsive to the electrostatically stimulating cancer cells of the cancerous tumor (step 2008). In an exemplary embodiment, active part 1904 of wire 1902 (or at least one of wires 1902*a*, 1902*b*, and 1902*c*, and combinations thereof) may be located at the first end 1912 of wire 1902. In an exemplary implementation, method 2000 may further include preparing wire 1902 (or any of wires 1902*a*,

1902*b*, and 1902*c*) for electrostatic tumor suppression (step 2002), which may be utilized for electrostatic tumor suppression.

Figure 21:
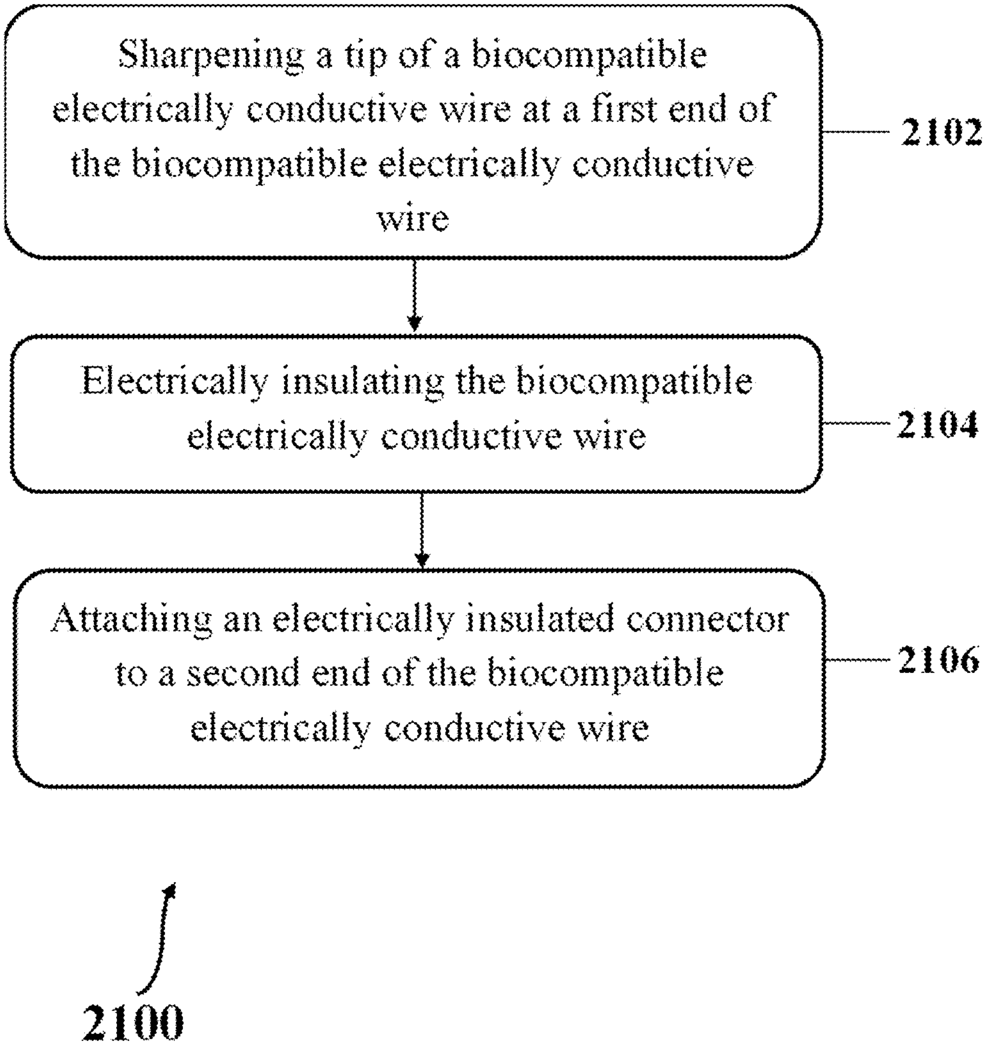
FIG. 21 illustrates an exemplary process for preparing an exemplary wire, consistent with one or more exemplary embodiments of the present disclosure.

In detail, step 2002 may include preparing wire 1902 (or any of wires 1902*a*, 1902*b*, and 1902*c*). FIG. 21 shows an exemplary process 2100 for preparing exemplary wire 1902 (or any of wires 1902*a*, 1902*b*, and 1902*c*) (step 2002), consistent with one or more exemplary embodiments of the present disclosure. Exemplary process 2100 may include electrically insulating a biocompatible electrically conductive wire by covering an electrical insulator layer around the biocompatible electrically conductive wire (step 2104), and attaching an electrically insulated connector to a second end of the biocompatible electrically conductive wire (step 2106).

In some implementations, exemplary process 2100 may further include forming a needle-shaped tip at a first end of the biocompatible electrically conductive wire by sharpening the tip of the biocompatible electrically conductive wire (step 2102); thereby, resulting in forming exemplary wire 1902 (or any of wires 1902*a*, 1902*b*, and 1902*c*) with exemplary sharp tip 1916 as shown in FIGS. 19A and 19C.

In an exemplary implementation, step 2104 may include covering an electrical insulator layer around the biocompatible electrically conductive wire except a tip of the biocompatible electrically conductive wire. In an exemplary implementation, step 2104 may include covering the electrical insulator layer around the biocompatible electrically conductive wire. In an exemplary implementation, covering the electrical insulator layer around the biocompatible electrically conductive wire may include covering a layer of a medical/biocompatible electrical insulator around the biocompatible electrically conductive wire. In an exemplary embodiment, the medical/biocompatible electrical insulator may include a non-conductive polymer, for example, polydimethylsiloxane (PDMS).

In an exemplary implementation, step 2104 may include covering the electrical insulator layer around a pre-defined length of the biocompatible electrically conductive wire. In an exemplary embodiment, the pre-defined length of the biocompatible electrically conductive wire may include a length of the biocompatible electrically conductive wire that may be configured to put in contact with a cancerous tumor. In an exemplary embodiment, the pre-defined length of the biocompatible electrically conductive wire may include length of active part 1904 of wire 1902 (or at least one of wires 1902*a*, 1902*b*, and 1902*c*, and combinations thereof). In an exemplary implementation, prior to preparing exemplary wire 1902 (or any of wires 1902*a*, 1902*b*, and 1902*c*), patients may be evaluated by any conventional imaging techniques to define tumor sizes and distance from the skin. So, exemplary wire 1902 (or any of wires 1902*a*, 1902*b*, and 1902*c*) may be prepared and customized based on the defined sizes. In an exemplary embodiment, the pre-defined length of the biocompatible electrically conductive wire may include a length of wire 1902 (or any of wires 1902*a*, 1902*b*, and 1902*c*) equal to a depth of a cancerous tumor from the skin to be covered with the electrical insulator layer in order to prevent charge leakage in other tissues rather than the cancerous tumor. The rest of wire 1902 (or any of wires 1902*a*, 1902*b*, and 1902*c*) may be retained uncovered in order to penetrate into the cancerous tumor and transfer electrostatic charge to the cancerous tumor. In an exemplary implementation, covering the electrical insulator layer around the biocompatible electrically conductive wire (step 2104) may include immersing the pre-defined length of the biocompatible electrically conductive wire into the electrical insulator material.

Figure 22:
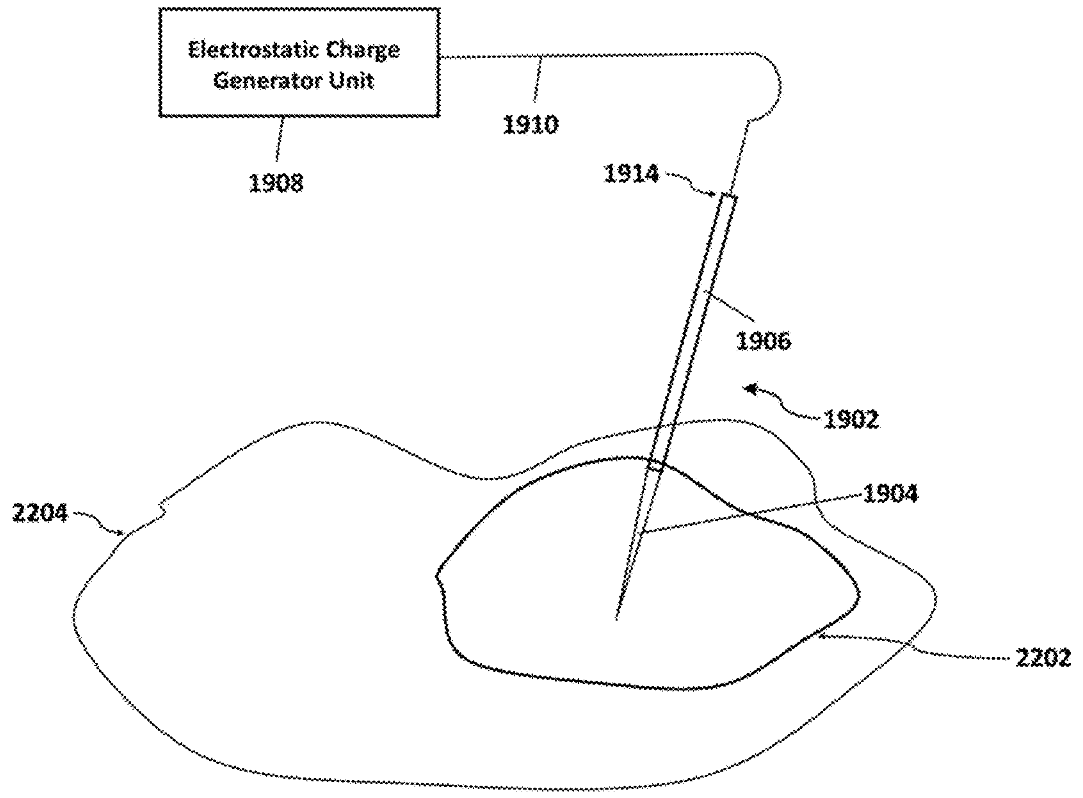
FIG. 22 illustrates an exemplary implementation of utilizing an exemplary system for tumor suppression via an exemplary method for tumor suppression, consistent with one or more exemplary embodiments of the present disclosure.

Referring to FIG. 20, step 2004 may include inserting active part 1904 of wire 1902 (or at least one of wires 1902*a*, 1902*b*, and 1902*c*, and combinations thereof) into a cancerous tumor. FIG. 22 shows an exemplary implementation of utilizing system 1900 (or similarly, system 1920) for tumor suppression via exemplary method 2000, consistent with one or more exemplary embodiments of the present disclosure. In an exemplary implementation, inserting active part 1904 of wire 1902 (or at least one of wires 1902*a*, 1902*b*, and 1902*c*, and combinations thereof) into the cancerous tumor may include inserting active part 1904 of wire 1902 (or at least one of wires 1902*a*, 1902*b*, and 1902*c*, and combinations thereof) into cancerous tumor 2202 located within normal (healthy) tissue 2204.

In an exemplary implementation, inserting active part 1904 of wire 1902 (or at least one of wires 1902*a*, 1902*b*, and 1902*c*, and combinations thereof) into cancerous tumor 2202 (step 2004) may include inserting active part 1904 of wire 1902 (or at least one of wires 1902*a*, 1902*b*, and 1902*c*, and combinations thereof) into cancerous tumor 2202 through skin of a patient involved with cancerous tumor 2202, and guiding active part 1904 of wire 1902 (or at least one of wires 1902*a*, 1902*b*, and 1902*c*, and combinations thereof) towards cancerous tumor 2202 by imaging cancerous tumor 2202 and peripheral tissues (normal (healthy/non-cancerous) tissue 2204) of cancerous tumor 2202. In an exemplary implementation, imaging cancerous tumor 2202 and peripheral tissues 2204 of cancerous tumor 2202 may include at least one of ultrasound imaging, sonography imaging, and mammography imaging cancerous tumor 2202 and peripheral tissues 2204 of cancerous tumor 2202. In such implementations, cancerous tumor 2202 may include cancerous tumors located near skin or superficial tumors. In such implementations, cancerous tumor 2202 may include at least one of an intra-dermal tumor, a gastrointestinal tumor, a breast tumor, and combinations thereof. In such implementations, active part 1904 of wire 1902 (or any of wires 1902*a*, 1902*b*, and 1902*c*) may include exemplary sharp tip 1916 as shown in FIG. 19A. In such exemplary embodiment, active part 1904 of wire 1902 (or any of wires 1902*a*, 1902*b*, and 1902*c*) may include a needle-shaped tip of wire 1902 at the first end 1912 of wire 1902.

In another exemplary implementation, inserting active part 1904 of wire 1902 (or at least one of wires 1902*a*, 1902*b*, and 1902*c*, and combinations thereof) into cancerous tumor 2202 (step 2004) may include locating (putting) active part 1904 of wire 1902 (or at least one of wires 1902*a*, 1902*b*, and 1902*c*, and combinations thereof) into cancerous tumor 2202 by a low-invasive surgery. In an exemplary embodiment, the low-invasive surgery may include at least one of a laparoscopy surgery, a robotic-based surgery, and combinations thereof. In such implementations, cancerous tumor 2202 may include a deep-seated cancerous tumor. In an exemplary embodiment, the deep-seated cancerous tumor may include a tumor of at least one of liver involved with a metastatic cancer, Hepatocellular carcinoma (HCC), Cholangiocarcinoma, cancers in deep-seated organs, and combinations thereof. In such implementations, active part 1904 of wire 1902 (or any of wires 1902*a*, 1902*b*, and 1902*c*) may include exemplary flat tip 1918 at first end 1912 of wire 1902 (or any of wires 1902*a*, 1902*b*, and 1902*c*) as shown in FIG. 19B.

In an exemplary implementation, inserting active part 1904 of wire 1902 (or at least one of wires 1902*a*, 1902*b*, and 1902*c*, and combinations thereof) into cancerous tumor 2202 (step 2004) may include locating a cancerous tumor localization guide wire into cancerous tumor 2202. In an exemplary implementation, inserting active part 1904 of wire 1902 (or at least one of wires 1902*a*, 1902*b*, and 1902*c*, and combinations thereof) into cancerous tumor 2202 (step 2004) may include locating the cancerous tumor localization guide wire into cancerous tumor 2202 utilizing a wire-guided localization technique, which may be utilized for localizing cancerous tumor 2202. In such implementations, the inserted active part 1904 of wire 1902 (or at least one of wires 1902*a*, 1902*b*, and 1902*c*, and combinations thereof) may include an implanted localization guide wire in cancerous tumor 2202 by a wire-guided localization technique.

In an exemplary implementation, step 2006 may include electrostatically stimulating cancer cells of exemplary cancerous tumor 2202 by injecting positive electrostatic charges to the cancer cells through the inserted active part 1904 of wire 1902 (or at least one of wires 1902*a*, 1902*b*, and 1902*c*, and combinations thereof). In an exemplary implementation, injecting the positive electrostatic charges to the cancer cells may include accumulating the positive electrostatic charges on the inserted active part 1904 of wire 1902 (or at least one of wires 1902*a*, 1902*b*, and 1902*c*, and combinations thereof), and generating a positive electrostatic charge flow through cancerous tumor 2202 responsive to accumulating the positive electrostatic charges on the inserted active part 1904 of wire 1902 (or at least one of wires 1902*a*, 1902*b*, and 1902*c*, and combinations thereof).

In an exemplary implementation, accumulating the positive electrostatic charges on the inserted active part 1904 of wire 1902 (or at least one of wires 1902*a*, 1902*b*, and 1902*c*, and combinations thereof) may include applying a positive electrostatic voltage to wire 1902 (or at least one of wires 1902*a*, 1902*b*, and 1902*c*, and combinations thereof). In an exemplary implementation, applying the positive electrostatic voltage to wire 1902 (or at least one of wires 1902*a*, 1902*b*, and 1902*c*, and combinations thereof) may include connecting the second end 1914 of wire 1902 (or at least one of wires 1902*a*, 1902*b*, and 1902*c*, and combinations thereof) to electrostatic charge generator 1908 using electrical connector 1910, and applying the positive electrostatic voltage with a voltage value between about 1 kV and about 30 kV to wire 1902 (or at least one of wires 1902*a*, 1902*b*, and 1902*c*, and combinations thereof) using electrostatic charge generator 1908.

In an exemplary implementation, electrostatically stimulating cancer cells of cancerous tumor 2202 may include internal apoptosis of the cancer cells in cancerous tumor 2202 that may be induced by positive charges accumulated on the inserted active part 1904 of wire 1902 (or any of wires 1902*a*, 1902*b*, and 1902*c*) due to a natural negative charge of the cancer cells. In an exemplary implementation, electrostatically stimulating cancer cells of cancerous tumor 2202 may include no stimulation of healthy (normal) cells of normal peripheral tissue (normal tissue 2204) due to a natural low negative charge of healthy (normal) cells. In an exemplary implementation, electrostatically stimulating cancer cells of cancerous tumor 2202 may include no stimulation of healthy (normal) cells placed either within cancerous tumor 2202 or nearby areas of cancerous tumor 2202.

In an exemplary implementation, step 2008 may include reducing size of cancerous tumor 2202 responsive to the electrostatically stimulating cancer cells of cancerous tumor 2202. In an exemplary implementation, positive electrostatic charges accumulated on the inserted active part 1904 of wire 1902 (or any of wires 1902*a*, 1902*b*, and 1902*c*) may induce internal apoptosis to naturally negative-charged cancerous cells without any effects on normal cells; thereby, reducing size of cancerous tumor 2202. In an exemplary implementation, reducing size of cancerous tumor 2202 may include a decrease in size of cancerous tumor 2202 by at least more than about 30%. In an exemplary implementation, reducing size of cancerous tumor 2202 may include completely elimination of cancerous tumor 2202.

In an exemplary implementation, electrostatically stimulating cancer cells of cancerous tumor 2202 and reducing size of cancerous tumor 2202 may be done concurrently in less than one week. In an exemplary implementation, electrostatically stimulating cancer cells of cancerous tumor 2202 and reducing size of cancerous tumor 2202 may be done in about three days to about five days.

In another aspect of the present disclosure, an exemplary method for deactivating and/or destroying circulating tumor cells (CTCs) is disclosed. Limitations and complications of common CTC capturing procedures have highly reduced the chance of selective destroying CTCs in bloodstream in therapeutic guidelines of cancer patients. Rare number of CTCs among plenty of blood cells (about 10 CTCs among billions of blood cells) makes their capturing very hard and almost impossible. Furthermore, their heterogeneity makes it hard to utilize biomarkers for their labeling. Herein, an exemplary method is disclosed for selectively deactivating invasive function of CTCs during their circulation in bloodstream by exposing whole bloodstream to pure positive electrostatic charge stimulation (PPECS). An exemplary method may be disclosed here without any need for capturing or targeting of CTCs from blood as the method may be based on intrinsic tendency of a malignant tumor to suppress its proliferation after being exposed to positive electrostatic charges. In an exemplary implementation, exemplary method may include continuous in-vivo deactivation of CTCs by PPECS with no requirement of complicated capturing protocols leading to improvement in survival of cancer patients. In some implementations of the present disclosure, an exemplary method may include deactivating/destroying CTCs by stimulating CTCs utilizing positive electrostatic charges. Exemplary method may include accumulating positive electrostatic charges near a portion of bloodstream by applying a positive electrostatic voltage to an electrical conductive element placed at a location near the portion of bloodstream. Exemplary method may be carried out through at least one scenario of in-vivo, in-vitro, and ex-vivo scenarios. In another general aspect, the present disclosure may be directed to an exemplary system for deactivating CTCs via electrostatically stimulating CTCs by positive electrostatic charges. Exemplary systems consistent with the present disclosure may be utilized by exemplary methods described herein for electrostatically stimulating CTCs; thereby, resulting in destroying and/or deactivating CTCs.

Figure 25A:
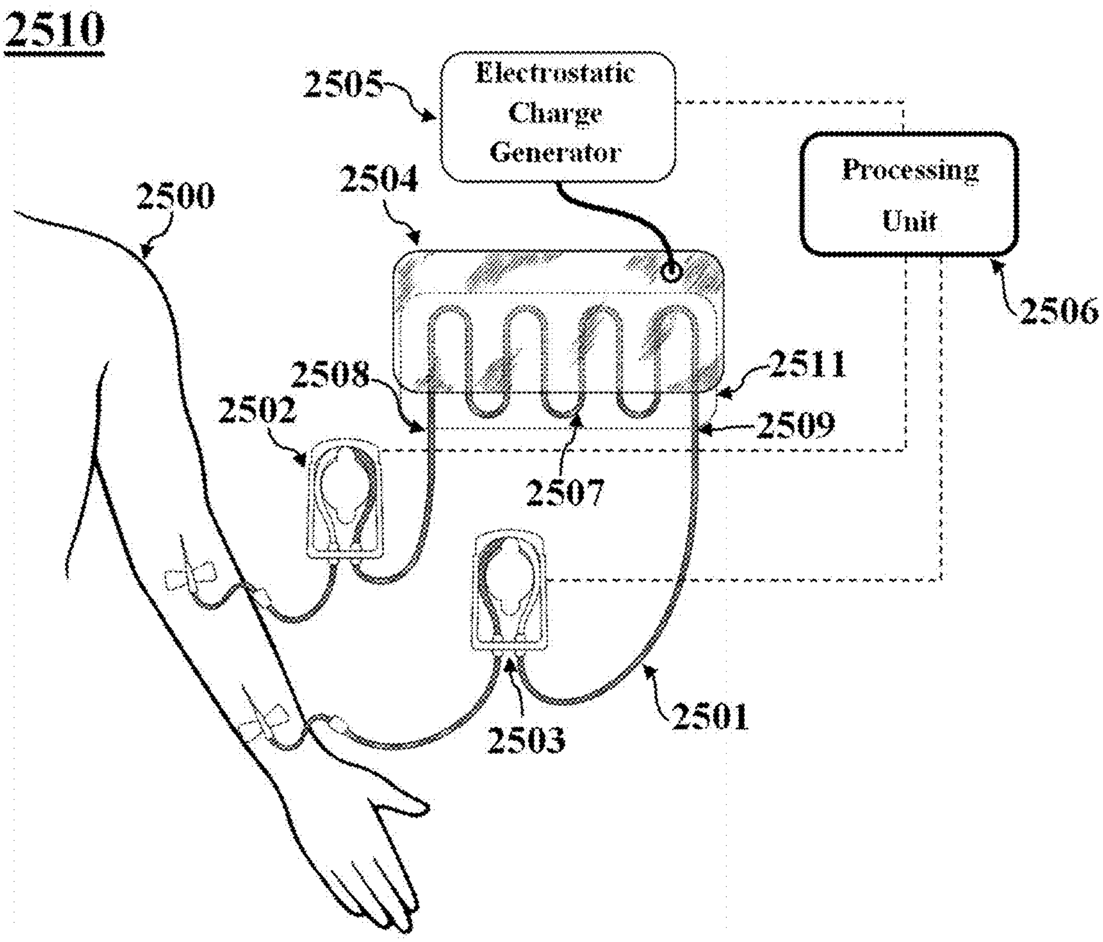
FIG. 25A shows a schematic view of a first exemplary implementation of a system for deactivating CTCs, consistent with one or more exemplary embodiments of the present disclosure.
Figure 25B:
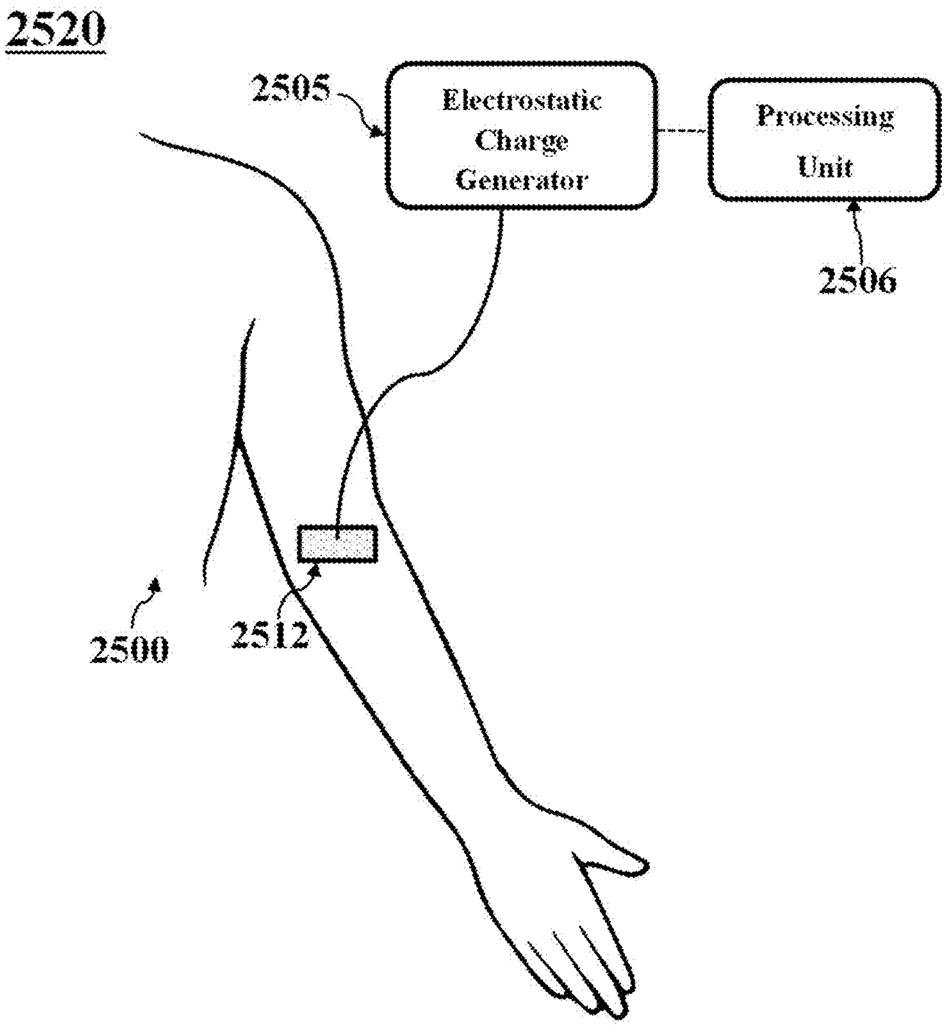
FIG. 25B shows a schematic view of a second exemplary implementation of a system for deactivating CTCs, consistent with one or more exemplary embodiments of the present disclosure.

FIGS. 25A and 25B show two schematic views respectively of two exemplary implementations of a system for deactivating CTCs, consistent with one or more exemplary embodiments of the present disclosure. Each of two exemplary systems 2510 and 2520 shown in FIGS. 25A and 25B, may be utilized for implementing exemplary methods for deactivating CTCs.

Referring to FIG. 25A, exemplary system 2510 may include tubing line 2501, at least two pumps 2502 and 2503, electrically conductive element 2504, and electrostatic charge generator 2505. In an exemplary embodiment, tubing line 2501 may include fluidic channel 2507. In an exemplary implementation, at least two pumps 2502 and 2503 may be configured to circulate a flow of bloodstream through tubing line 2501. In an exemplary embodiment, electrically conductive element 2504 may be placed on fluidic channel 2507, and electrically connected to electrostatic charge generator 2505. In an exemplary implementation, electrically conductive element 2504 may be configured to accumulate positive electrostatic charges thereon. In an exemplary implementation, electrostatic charge generator 2505 may be configured to apply a positive electrostatic voltage to electrically conductive element 2504 leading to accumulate positive electrostatic charges on electrically conductive element 2504.

In an exemplary embodiment, fluidic channel 2507 may include a portion of tubing line 2501 with a spiral u-shape with two ends. In an exemplary embodiment, the two ends of fluidic channel 2507 may include inlet 2508 and outlet 2509. In an exemplary embodiment, fluidic channel 2507 may include a portion of tubing line 2501 that may be formed in a spiral u-shape and fixed on base plate 2511. In an exemplary embodiment, tubing line 2501 may include a flexible tube made of a biocompatible flexible material. In an exemplary embodiment, tubing line 2501 may be made of silicon.

In an exemplary embodiment, fluidic channel 2507 and at least two pumps 2502 and 2503 may be replaced by a Hemodialysis device. The Hemodialysis device may include at least one tube and at least one pump. The at least one pump of the Hemodialysis device may be configured to circulate or pass bloodstream through the at least one tube of the Hemodialysis device. The Hemodialysis device may be configured to circulate bloodstream of cancer patient 2500 through the at least one tube utilizing the at least one pump. In an exemplary embodiment, electrically conductive element 2504 may be placed on the at least one tube of the Hemodialysis device. In an exemplary embodiment, electrically conductive element 2504 may be configured to be placed on a portion of the at least one tube of the Hemodialysis device through which the bloodstream may be circulated.

In an exemplary embodiment, the at least two pumps 2502 and 2503 may include a first peristaltic pump 2502 that may be configured to extract bloodstream of a cancer patient' body (e.g., cancer patient 2500) into inlet 2508 of fluidic channel 2507. The first peristaltic pump 2502 may be configured to extract a flow of bloodstream of cancer patient 2500 from a superficial vein of cancer patient 2500 and transmit the extracted flow of bloodstream into inlet 2508 of fluidic channel 2507. In an exemplary embodiment, the superficial vein may include a cephalic vein of an arm of cancer patient 2500. In an exemplary embodiment, the extracted flow of bloodstream may include a plurality of CTCs.

In an exemplary embodiment, the at least two pumps 2502 and 2503 may include a second peristaltic pump 2503 that may be configured to transmit the flow of bloodstream from outlet 2509 of fluidic channel 2507 into the cancer patient's body (e.g., cancer patient 2500). The transmitted flow of bloodstream by the second peristaltic pump 2503 may be re-injected into cancer patient's body via a superficial vein at wrist of cancer patient 2500. In an exemplary embodiment, the transmitted flow of bloodstream may include a plurality of destroyed or deactivated CTCs.

In an exemplary embodiment, electrically conductive element 2504 may include at least one of an electrical conductive plate and an electrical conductive tape. In another exemplary embodiment, electrically conductive element 2504 may include at least one of an electrical insulator plate and an electrical insulator tape and a layer of an electrically conductive material covered on the least one of an electrical insulator plate and an electrical insulator tape. In an exemplary embodiment, the layer of the electrically conductive material may include a sheet of aluminum (Al).

In an exemplary embodiment, electrostatic charge generator 2505 may be configured to apply positive electrostatic voltages in a range of about 50 V to about 50 kV to electrically conductive element 2504. In an exemplary embodiment, electrostatic charge generator 2505 may include a Van de Graaff generator.

In an exemplary embodiment, system 2510 may further include processing unit 2506. In an exemplary embodiment, processing unit 2506 may be electrically connected to electrostatic charge generator 2505 and the at least two pumps 2502 and 2503 via an electrical wire/cable or a wireless connection, for example, utilizing Bluetooth devices or Bluetooth modules. In an exemplary embodiment, processing unit 2506 may include a memory having processor-readable instructions stored therein and a processor configured to access the memory and execute the processor-readable instructions, which, when executed by the processor configures the processor to perform a method. In an exemplary embodiment, the method may include an exemplary method for deactivating CTCs described herein.

FIG. 25B shows a schematic view of a second exemplary implementation of a system for deactivating CTCs, consistent with one or more exemplary embodiments of the present disclosure. In an exemplary implementation, exemplary system 2520 may include electrically conductive element 2512 and electrostatic charge generator 2505. In an exemplary implementation, electrically conductive element 2512 may be configured to accumulate positive electrostatic charges thereon. In an exemplary implementation, electrostatic charge generator 2505 may be configured to apply a positive electrostatic voltage to electrically conductive element 2512 leading to accumulate positive electrostatic charges on electrically conductive element 2512. In an exemplary embodiment, electrically conductive element 2512 may be configured to be adhered or attached over skin of cancer patient 2500 at a location of a part of a superficial vein of cancer patient 2500.

In an exemplary embodiment, electrically conductive element 2512 may include a layer of an electrically conductive material. In an exemplary embodiment, electrically conductive element 2512 may further include a substrate, where the layer of the electrically conductive material may be attached on the substrate. In an exemplary embodiment, the substrate may include a layer of an electrical insulator material.

In an exemplary embodiment, the layer of the electrically conductive material may include a layer of electrically conductive nanostructures. In an exemplary embodiment, the layer of electrically conductive nanostructures may include a layer of at least one of carbon nanotubes (CNTs), vertically aligned multi-walled carbon nanotube (VAMWCNTs), graphene, zinc dioxide (ZnO), Silicon nanowires (SiNWs), Silicon nanograss, $TiO_2$ nanotubes, $TiO_2$ nanowires, metallic layers and combinations thereof. In an exemplary embodiment, the substrate may include a multi-layered structure. In an exemplary embodiment, the substrate may include a layer of silicon (Si), a layer of silicon dioxide ($SiO_2$) grown on the layer of silicon, and a catalyst layer deposited on the layer of $SiO_2$. In an exemplary embodiment, catalyst layer may be configured to grow the layer of electrically conductive nanostructures thereon.

In an exemplary embodiment, electrostatic charge generator 2505 may be configured to apply positive electrostatic voltages in a range of about 50 V to about 50 kV to electrically conductive element 2512. In an exemplary embodiment, electrostatic charge generator 2505 may include a Van de Graaff generator.

In an exemplary embodiment, system 2520 may further include processing unit 2506. In an exemplary embodiment, processing unit 2506 may be electrically connected to electrostatic charge generator 2505 via an electrical wire/cable or a wireless connection, for example, utilizing Bluetooth devices or Bluetooth modules. In an exemplary embodiment, processing unit 2506 may include a memory having processor-readable instructions stored therein and a processor configured to access the memory and execute the processor-readable instructions, which, when executed by the processor configures the processor to perform a method. In an exemplary embodiment, the method may include an exemplary method for deactivating CTCs described herein.

In another aspect of the present disclosure, an exemplary method for deactivating CTCs is disclosed. The method may include an in-vivo method for deactivating CTCs utilizing exemplary systems 2510 or 2520. In an exemplary implementation, the method may include deactivating CTCs by applying a positive electrostatic field to bloodstream of a cancer patient. In an exemplary implementation, deactivating CTCs may include at least one of reducing viability of CTCs and completely or partially destroying CTCs. In an exemplary implementation, utilizing exemplary method may lead to much less invasive function, low matrix metalloproteinases (MMP) expression, separated spheroid formation, low spheroid invasion, and low metastatic function for treated CTCs with exemplary method in comparison with high invasive function, high MMP expression, integrated spheroid formation, high spheroid invasion, and high metastatic function for non-treated CTCs.

In an exemplary implementation, applying the positive electrostatic field to the bloodstream of the cancer patient may include accumulating positive electrostatic charges on an electrically conductive element similar to electrically conductive element 2504 or electrically conductive element 2512 by applying a positive electrostatic voltage to either electrically conductive elements 2504 or 2512 utilizing exemplary electrostatic charge generator 2505 and exposing the bloodstream to the accumulated positive electrostatic charges by placing either electrically conductive elements 2504 or 2512 with the accumulated positive electrostatic charges thereon adjacent to a portion of the bloodstream. In an exemplary implementation, applying the positive electrostatic voltage to the electrically conductive element 2504 or 2512 may include applying the positive electrostatic voltage in a range of about 50 V to about 50 kV to either electrically conductive elements 2504 or 2512 utilizing electrostatic charge generator 2505. In an exemplary implementation, placing electrically conductive elements 2504 or 2512 with the accumulated positive electrostatic charges thereon adjacent to the portion of the bloodstream may include placing electrically conductive elements 2504 or 2512 with the accumulated positive electrostatic charges thereon at a distance of less than about 10 cm from the portion of the bloodstream. In an exemplary implementation, deactivating CTCs by applying the positive electrostatic field to the bloodstream of the cancer patient may be done daily for a range of about 1 hour to about 5 hours for at least three days.

Figure 26:
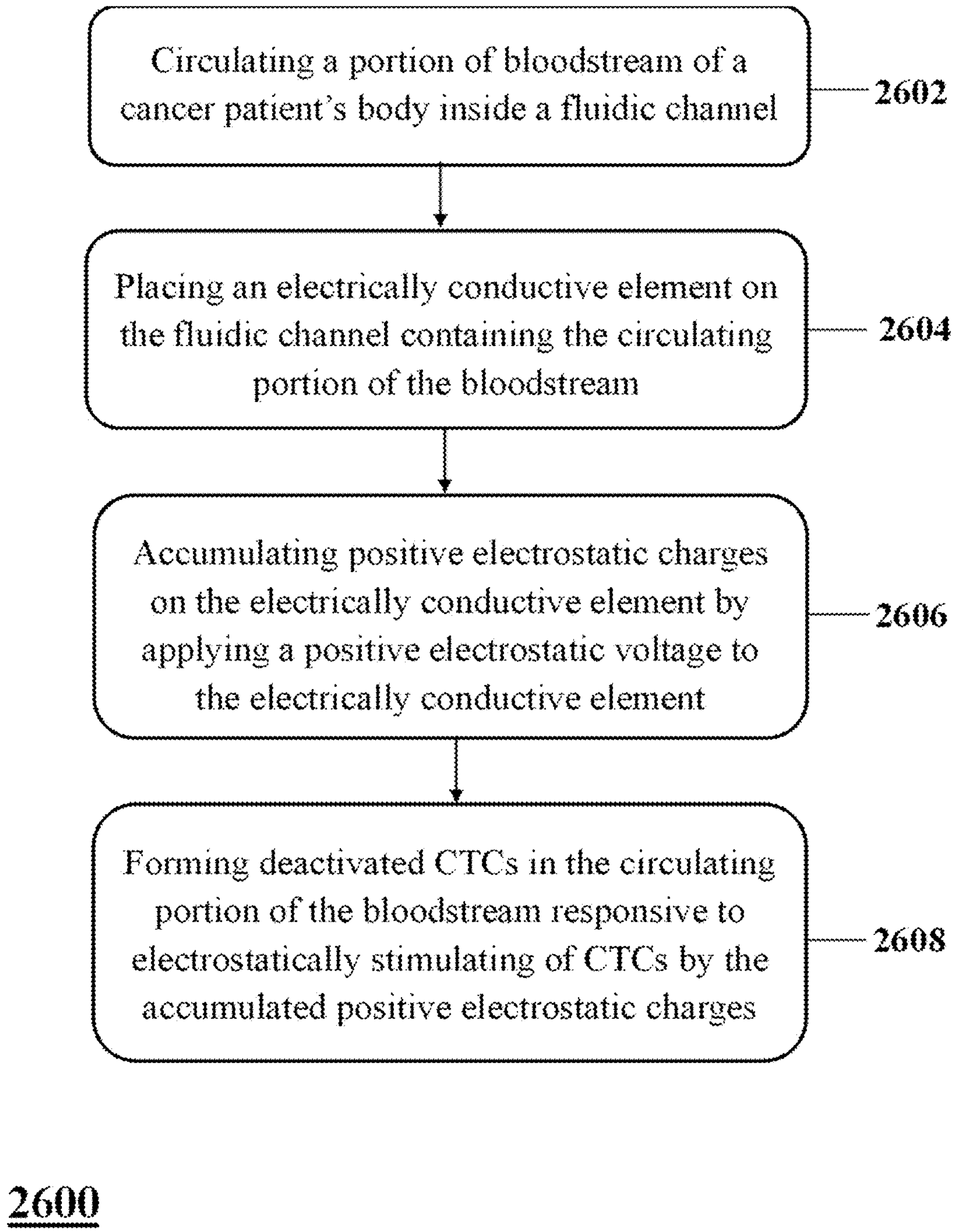
FIG. 26 shows an exemplary implementation of a method for deactivating CTCs, consistent with one or more exemplary embodiments of the present disclosure.

FIG. 26 shows an exemplary implementation of method 2600 for deactivating CTCs, consistent with one or more exemplary embodiments of the present disclosure. In an exemplary implementation, exemplary method 2600 may utilize exemplary system 2510 for deactivating CTCs. In an exemplary implementation, method 2600 may include circulating a portion of bloodstream of a cancer patient's body (e.g., cancer patient 2500) inside fluidic channel 2507 (step 2602), placing electrically conductive element 2504 on fluidic channel 2507 containing the circulating portion of the bloodstream (step 2604), accumulating positive electrostatic charges on electrically conductive element 2504 by applying a positive electrostatic voltage to electrically conductive element 2504 utilizing electrostatic charge generator 2505 (step 2606), and forming deactivated CTCs in the circulating portion of the bloodstream responsive to electrostatically stimulating of CTCs induced by the accumulated positive electrostatic charges (step 2608).

In detail, step 2602 may include circulating a portion of bloodstream of a cancer patient's body (e.g., cancer patient 2500) inside fluidic channel 2507. In an exemplary implementation, circulating the portion of bloodstream of cancer patient 2500 inside fluidic channel 2507 may include extracting the portion of the bloodstream of cancer patient's body into fluidic channel 2507 and re-injecting the portion of the bloodstream from fluidic channel 2507 to the cancer patient's body. Where, extracting the portion of the bloodstream and re-injecting the portion of the bloodstream are done continuously in a cycle.

In an exemplary implementation, circulating the portion of bloodstream of cancer patient 2500 inside fluidic channel 2507 may be done at a flow rate in a range of about 5 ml/min to about 500 ml/min. In an exemplary implementation, the flow rate of circulating the portion of bloodstream may be determined based on weight of cancer patient 2500. In an exemplary implementation, the flow rate of circulating the portion of bloodstream may be determined according to the following relation (Eq. 1):

$$\text{Flow rate of bloodstream circulation}\left(\frac{\text{ml}}{\text{min}}\right) = 4\times\text{Weight of cancer patient 2500 (Kg)} \quad \text{Eq. 1}$$

In an exemplary implementation, circulating the portion of bloodstream of cancer patient 2500 inside fluidic channel 2507 may be done utilizing at least two pumps 2502 and 2503. In an exemplary embodiment, the at least two pumps 2502 and 2503 may include two peristaltic pumps. In an exemplary embodiment, the at least two pumps 2502 and 2503 may include the first peristaltic pump 2502 that may be configured to extract the portion of the bloodstream of the cancer patient's body into fluidic channel 2507 and the second peristaltic pump 2503 that may be configured to transmit the portion of the bloodstream from fluidic channel 2507 to the cancer patient's body.

In an exemplary embodiment, the first peristaltic pump 2502 may be configured to extract the portion of the bloodstream of the cancer patient's body and pass the extracted bloodstream through fluidic channel 2507. In an exemplary embodiment, a flow rate of the bloodstream through the first peristaltic pump 2502 may be adjusted at a desired flow rate to be passed through fluidic channel 2507. In an exemplary embodiment, the flow rate of the bloodstream through the first peristaltic pump 2502 may be adjusted at a flow rate in a range of about 5 ml/min to about 500 ml/min. In an exemplary embodiment, the flow rate of the bloodstream through the first peristaltic pump 2502 may be adjusted according to Eq. 1 described hereinabove. In an exemplary embodiment, the flow rate of the bloodstream through the first peristaltic pump 2502 may be adjusted at about 7.4 ml/min; allowing for mimicking physiologically related flows and shear stresses in superficial veins such as cephalic vein of arm.

In an exemplary embodiment, the second peristaltic pump 2503 may be configured to transmit or enter the portion of the bloodstream from fluidic channel 2507 to the cancer patient's body. In an exemplary embodiment, a flow rate of the bloodstream through the second peristaltic pump 2503 may be adjusted at a safe and not damaging flow rate for a vein of the cancer patient's body that the portion of the bloodstream may be entered there. In an exemplary embodiment, the flow rate of the bloodstream through the second peristaltic pump 2503 may be adjusted at a flow rate in a range of about 5 ml/min to about 500 ml/min depending on the patient's conditions. In an exemplary embodiment, the flow rate of the bloodstream through the second peristaltic pump 2503 may be adjusted according to Eq. 1 described hereinabove. In an exemplary embodiment, the flow rate of the bloodstream through the second peristaltic pump 2503 may be adjusted at about 7.4 ml/min as a safe and not damaging flow rate for entering the bloodstream into a vein of the cancer patient's body.

In an exemplary implementation, step 2604 may include placing electrically conductive element 2504 on fluidic channel 2507 containing the circulating portion of the bloodstream. In an exemplary implementation, placing electrically conductive element 2504 on fluidic channel 2507 may include putting a surface of electrically conductive element 2504 on fluidic channel 2507 so that an outer surface of fluidic channel 2507 may be covered with electrically conductive element 2504. A complete covering of electrically conductive element 2504 on fluidic channel 2507 may allow for a uniform distribution of positive electrostatic charges on fluidic channel 2507.

In an exemplary implementation, circulating the portion of bloodstream of cancer patient 2500 (step 2602) may be done utilizing a Hemodialysis device. In such implementations, the Hemodialysis device may be utilized instead of bloodstream circulating loop of system 2510 which may include tubing line 2501 and pumps 2502 and 2503. In such implementation, step 2604 may include placing electrically conductive element 2504 on a portion of tube lines of the Hemodialysis device through which the bloodstream may be circulated.

Furthermore, step 2606 may include accumulating positive electrostatic charges on electrically conductive element 2504 by applying a positive electrostatic voltage to electrically conductive element 2504 utilizing electrostatic charge generator 2505. In an exemplary implementation, applying the positive electrostatic voltage to electrically conductive element 2504 may include applying a positive electrostatic voltage in a range of about 50 V to about 50 kV to electrically conductive element 2504 utilizing electrostatic charge generator 2505.

Moreover, step 2608 may include forming deactivated CTCs in the circulating portion of the bloodstream responsive to electrostatically stimulating of CTCs by the accumulated positive electrostatic charges on electrically conductive element 2504. In an exemplary implementation, the accumulated positive electrostatic charges on electrically conductive element 2504 may induce an electrostatically stimulation on cancer cells, i.e., CTCs. The electrostatically stimulation of CTCs by positive electrostatic charges may deactivate cancerous functions of CTCs. In an exemplary embodiment, electrostatically stimulation of CTCs may induce apoptosis in CTCs. Therefore, electrostatically stimulated CTCs may be deactivated, for example, may be less invasive or completely destroyed.

In an exemplary implementation, deactivating CTCs by applying the positive electrostatic field to the bloodstream of cancer patient 2500 via method 2600 may be done daily for a time period in a range of about 3 days to one month. In an exemplary implementation, applying the positive electrostatic field to the bloodstream of cancer patient 2500 may be done daily for a range of about 1 hour to about 5 hours for at least three days to about 1 month.

Figure 27:
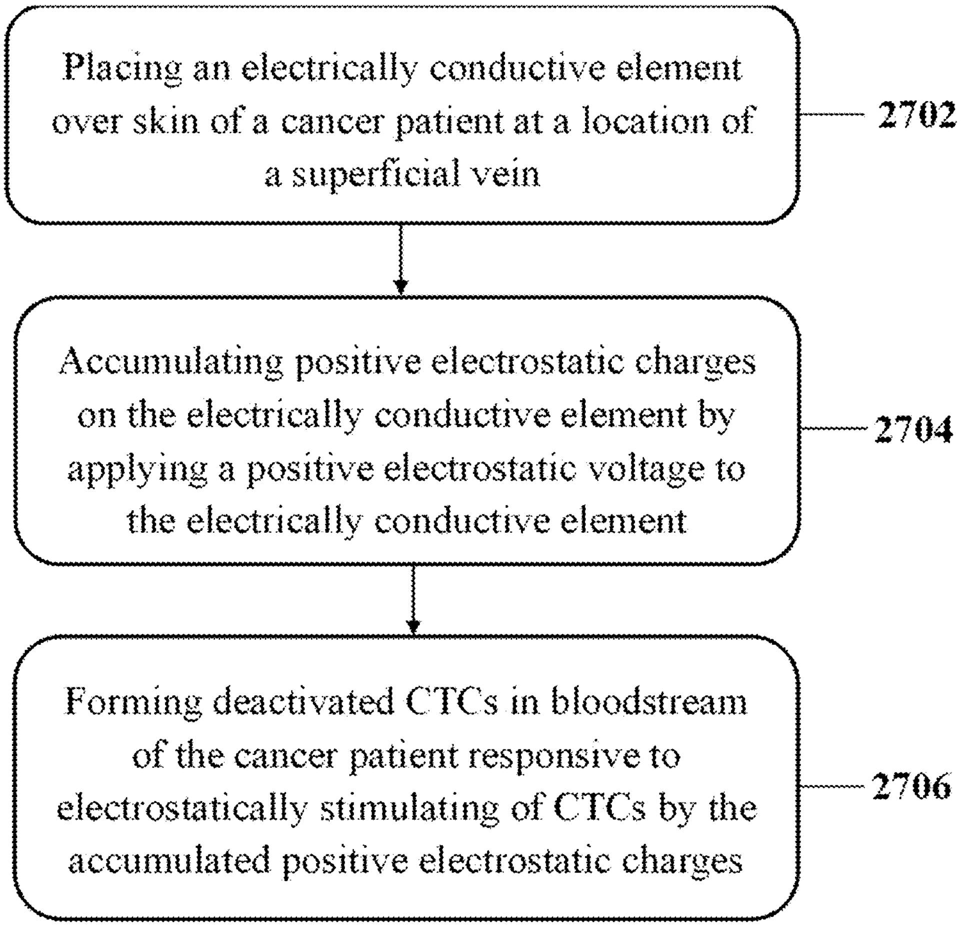
FIG. 27 shows another exemplary implementation of a method for deactivating CTCs, consistent with one or more exemplary embodiments of the present disclosure.

FIG. 27 shows another exemplary implementation of method 2700 for deactivating CTCs, consistent with one or more exemplary embodiments of the present disclosure. In an exemplary implementation, exemplary method 2700 may utilize exemplary system 2520 for deactivating CTCs. In an exemplary implementation, method 2700 may include placing electrically conductive element 2512 over skin of cancer patient 2500 at a location of a superficial vein of cancer patient 2500 (step 2702), accumulating positive electrostatic charges on electrically conductive element 2512 by applying a positive electrostatic voltage to electrically conductive element 2512 utilizing electrostatic charge generator 2505 (step 2704), and forming deactivated CTCs in the bloodstream of cancer patient 2500 responsive to electrostatically stimulating of CTCs induced by the accumulated positive electrostatic charges (step 2706).

In detail, step 2702 may include placing electrically conductive element 2512 over skin of cancer patient 2500 at a location of a superficial vein of cancer patient 2500. In an exemplary embodiment, the superficial vein may include a vein that may be close to a surface of body. The superficial vein may be located under skin. In an exemplary embodiment, the location of the superficial vein may include a portion of skin of cancer patient 2500 located above the superficial vein or a part of surface of cancer patient 2500 located above the superficial vein. In an exemplary implementation, step 2702 may include placing electrically conductive element 2512 on a part of skin of neck or arm of cancer patient 2500 at a location of a superficial vein of cancer patient 2500. In an exemplary implementation, placing electrically conductive element 2512 over skin of cancer patient 2500 may include adhering or attaching electrically conductive element 2512 over skin of cancer patient 2500.

Furthermore, step 2704 may include accumulating positive electrostatic charges on electrically conductive element 2512 by applying a positive electrostatic voltage to electrically conductive element 2512 utilizing electrostatic charge generator 2505. In an exemplary implementation, applying the positive electrostatic voltage to electrically conductive element 2512 may include applying a positive electrostatic voltage in a range of about 50 V to about 50 kV to electrically conductive element 2512 utilizing electrostatic charge generator 2505.

Moreover, step 2706 may include forming deactivated CTCs in the circulating portion of the bloodstream responsive to electrostatically stimulating of CTCs by the accumulated positive electrostatic charges on electrically conductive element 2512. In an exemplary implementation, the accumulated positive electrostatic charges on electrically conductive element 2512 may induce an electrostatically stimulation on cancer cells, i.e., CTCs. The electrostatically stimulation of CTCs by positive electrostatic charges may deactivate cancerous functions of CTCs. In an exemplary embodiment, electrostatically stimulation of CTCs may induce apoptosis in CTCs. Therefore, electrostatically stimulated CTCs may be deactivated, for example, may be less invasive or completely destroyed.

In an exemplary implementation, deactivating CTCs by applying the positive electrostatic field to the bloodstream of cancer patient 2500 via method 2700 may be done by conducting steps of method 2700 daily for a time period in a range of about 3 days to one month. In an exemplary implementation, applying the positive electrostatic field to the bloodstream of cancer patient 2500 may be done daily for a range of about 1 hour to about 5 hours for at least three days to about 1 month.

Referring to FIGS. 25A and 25B, an exemplary system for deactivation CTCs (similar to systems 2510 and 2520) may further include processing unit 2506. In an exemplary embodiment, processing unit 2506 may be electrically connected to electrostatic charge generator 2505 and also the at least two pumps 2502 and 2503 of system 2510 via an electrical wire/cable or a wireless connection, for example, utilizing Bluetooth devices or Bluetooth modules. In an exemplary embodiment, processing unit 2506 may include a memory having processor-readable instructions stored therein and a processor configured to access the memory and execute the processor-readable instructions, which, when executed by the processor configures the processor to perform a method. In an exemplary embodiment, the performed method may include an exemplary method for deactivating CTCs described hereinabove similar to methods 2600 and 2700 respective to systems 2510 and 2520.

Figure 25C:
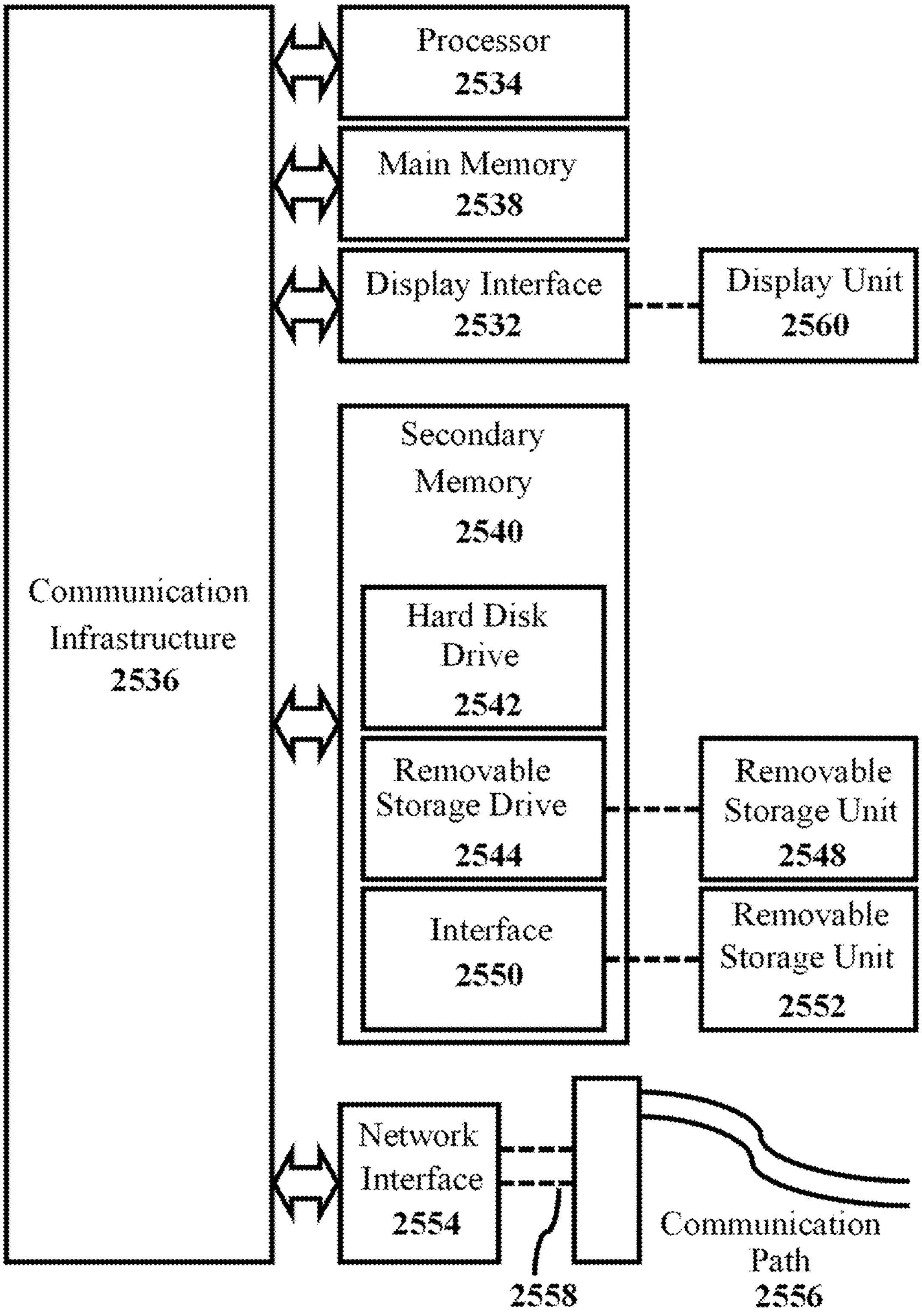
FIG. 25C shows an exemplary computer system in which an embodiment of the present disclosure or portions thereof, may be implemented as computer-readable code, consistent with one or more exemplary embodiments of the present disclosure.

FIG. 25C shows an example computer system 2530 in which an embodiment of the present disclosure, or portions thereof, may be implemented as computer-readable code, consistent with one or more exemplary embodiments of the present disclosure. For example, computer system 2530 may include an example of processing unit 2506, and steps 2602, 2606, and 2608, and steps 2704 and 2706 of flowcharts presented in FIGS. 25A-25B, may be implemented in computer system 2530 using hardware, software, firmware, tangible computer readable media having instructions stored thereon, or a combination thereof and may be implemented in one or more computer systems or other processing systems. Hardware, software, or any combination of such may embody any of the modules and components in FIGS. 25A-25B.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the present disclosure is described in terms of this example computer system 2530. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 2534 may be a special purpose or a general-purpose processor device. As will be appreciated by persons skilled in the relevant art, processor device 2534 may also be a single processor in a multi-core/multiprocessor system, such system operating alone, or in a cluster of computing devices operating in a cluster or server farm. Processor device 2534 may be connected to a communication infrastructure 2536, for example, a bus, message queue, network, or multi-core message-passing scheme.

In an exemplary embodiment, computer system 2530 may include a display interface 2532, for example a video connector, to transfer data to a display unit 2560, for example, a monitor. Computer system 2530 may also include a main memory 2538, for example, random access memory (RAM), and may also include a secondary memory 2540. Secondary memory 2540 may include, for example, a hard disk drive 2542, and a removable storage drive 2544. Removable storage drive 2544 may include a floppy disk drive, a magnetic tape drive, an optical disk drive, a flash memory, or the like. Removable storage drive 2544 may read from and/or write to a removable storage unit 2548 in a well-known manner. Removable storage unit 2548 may include a floppy disk, a magnetic tape, an optical disk, etc., which may be read by and written to by removable storage drive 2544. As will be appreciated by persons skilled in the relevant art, removable storage unit 2548 may include a computer usable storage medium having stored therein computer software and/or data.

In alternative implementations, secondary memory 2540 may include other similar means for allowing computer programs or other instructions to be loaded into computer system 2530. Such means may include, for example, a removable storage unit 2552 and an interface 2550. Examples of such means may include a program cartridge and cartridge interface (such as that found in video game devices), a removable memory chip (such as an EPROM, or PROM) and associated socket, and other removable storage units 2552 and interfaces 2550 which allow software and data to be transferred from removable storage unit 2552 to computer system 2530.

Computer system 2530 may also include a communications interface 2554 (network interface 2554). Communications interface 2554 allows software and data to be transferred between computer system 2530 and external devices. Communications interface 2554 may include a modem, a network interface (such as an Ethernet card), a communications port, a PCMCIA slot and card, or the like. Software and data transferred via communications interface 2554 may be in the form of signals, which may be electronic, electromagnetic, optical, or other signals capable of being received by communications interface 2554. These signals may be provided to communications interface 2554 via a communications path 2556. Communications path 2556 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 2548, removable storage unit 2552, and a hard disk installed in hard disk drive 2542. Computer program medium and computer usable medium may also refer to memories, such as main memory 2538 and secondary memory 2540, which may be memory semiconductors (e.g. DRAMs, etc.).

Computer programs (also called computer control logic) are stored in main memory 2538 and/or secondary memory 2540. Computer programs may also be received via communications interface 2554. Such computer programs, when executed, enable computer system 2530 to implement different embodiments of the present disclosure as discussed herein. In particular, the computer programs, when executed, enable processor device 2534 to implement the processes of the present disclosure, such as the operations in methods 2600 and 2700 illustrated by FIGS. 26 and 27, discussed above. Accordingly, such computer programs represent controllers of computer system 2530. Where an exemplary embodiment of each of methods 2600 and 2700 is implemented using software, the software may be stored in a computer program product and loaded into computer system 2530 using removable storage drive 2544, interface 2550, and hard disk drive 2542, or communications interface 2554.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

Example 1: Fabrication of Vertically Aligned Multi-Walled Carbon Nanotube (VAMWCNT) Arrays as Therapeutic Patch In this example, exemplary therapeutic chips similar to exemplary chip 200 were fabricated. First, silicon wafer substrates were cleaned through standard RCA #1 method ($NH_4OH$:$H_2O_2$:$H_2O$ solution and volume ratio of 1:1:5 respectively). Then, a thin layer of $SiO_2$ with a thickness of about 200 nm was grown by wet oxidation furnace on the surface of the silicon wafer. Afterwards, a layer of Nickel (Ni) with a thickness of about 9 nm was deposited on $SiO_2$ using an E-beam evaporation system. Using a direct current plasma enhanced chemical vapor deposition (DC-PECVD) system, the Ni-coated samples were annealed at about 650° C. in a dynamic $H_2$ environment with a flow rate of about 35 standard cubic centimeters per minute (SCCM) for about 15 minutes. Thermally treated Ni layer was hydrogenated by plasma with a power density of about 5.5 $Wcm^{-2}$ for about 5 minutes to obtain Ni nano-grains. The CNTs were grown on the Ni seeds in the same chamber containing a mixture of $H_2$ and $C_2H_2$ gases with flow rates of about 35 SCCM of $H_2$ and about 5 SCCM of $C_2H_2$ at a temperature of 650° C. and a pressure of about 0.28 kPa for about 15 minutes.

Figure 4:
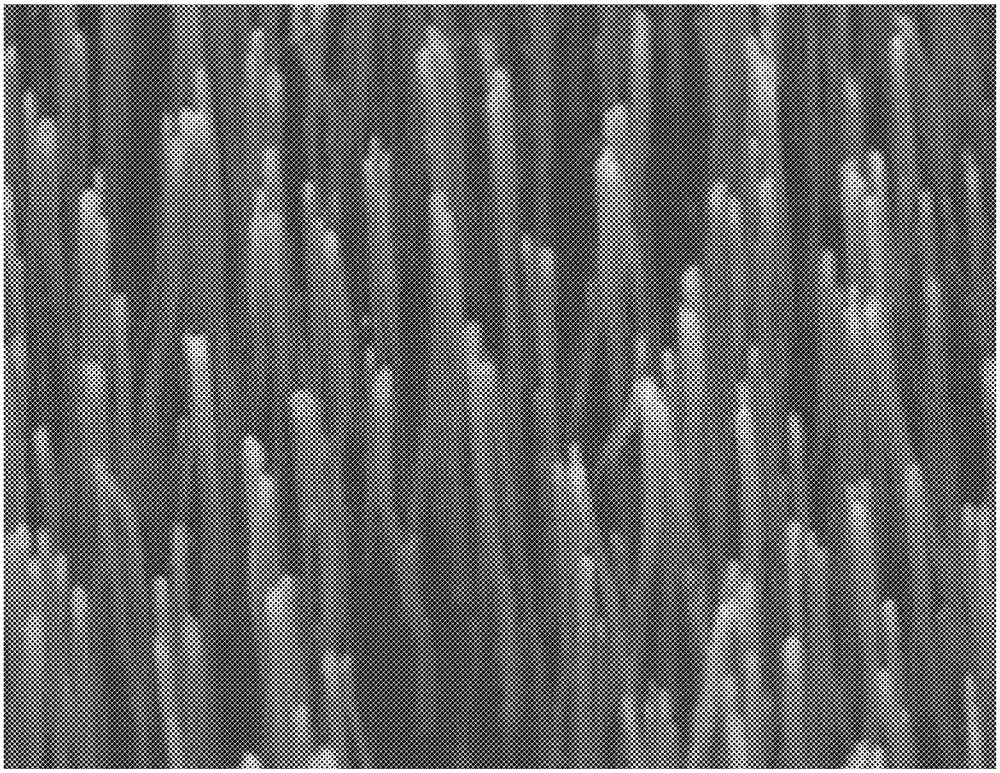
FIG. 4 illustrates a field emission scanning electron microscopy (FESEM) image of the VAMWCNTs array on a portion of an exemplary fabricated chip, consistent with one or more exemplary embodiments of the present disclosure.

CNT Effective Charged Surface Calculations:

FIG. 4 shows a field emission scanning electron microscopy (FESEM) image of the VAMWCNTs array on a portion of an exemplary fabricated chip, consistent with one or more exemplary embodiments of the present disclosure. The CNTs were multi-walled carbon nanotubes with high purity. The comparative effective charged surface in chips with and without CNTs was calculated to enlighten the role of the nanotubes to enlarge the amount of electrostatic charge. Analysis of the interactive surface enhancement by VAMWCNT array showed that the presence of CNTs increased the effective surface in each about 1 $\mu m^2$ to about 24.6 $\mu m^2$.

Figure 5A:
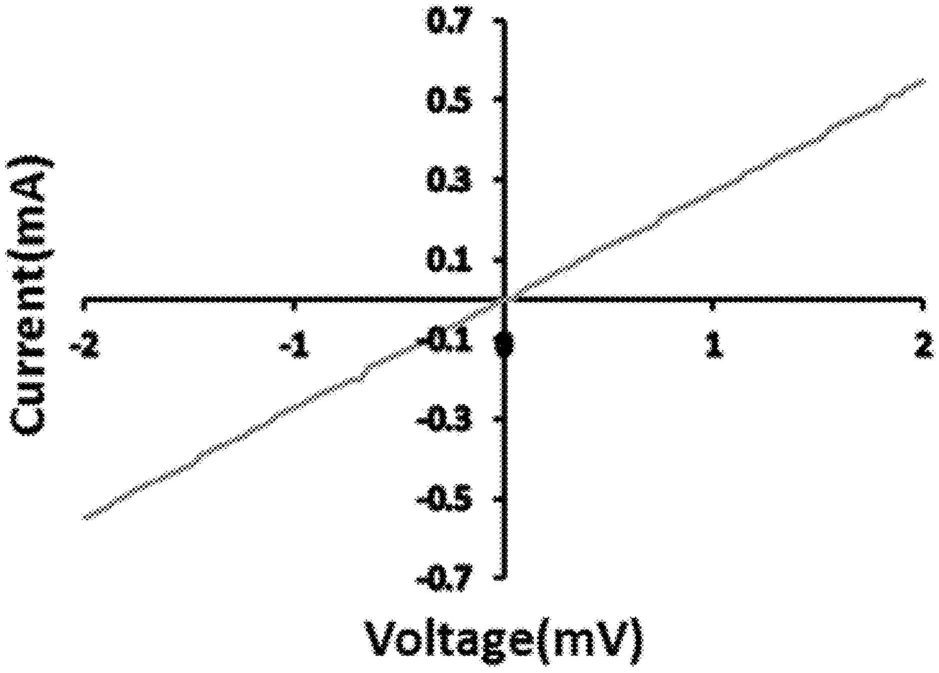
FIG. 5A illustrates current versus voltage (I-V) diagram for exemplary CNTs array of exemplary fabricated chip, consistent with one or more exemplary embodiments of the present disclosure.
Figure 5B:
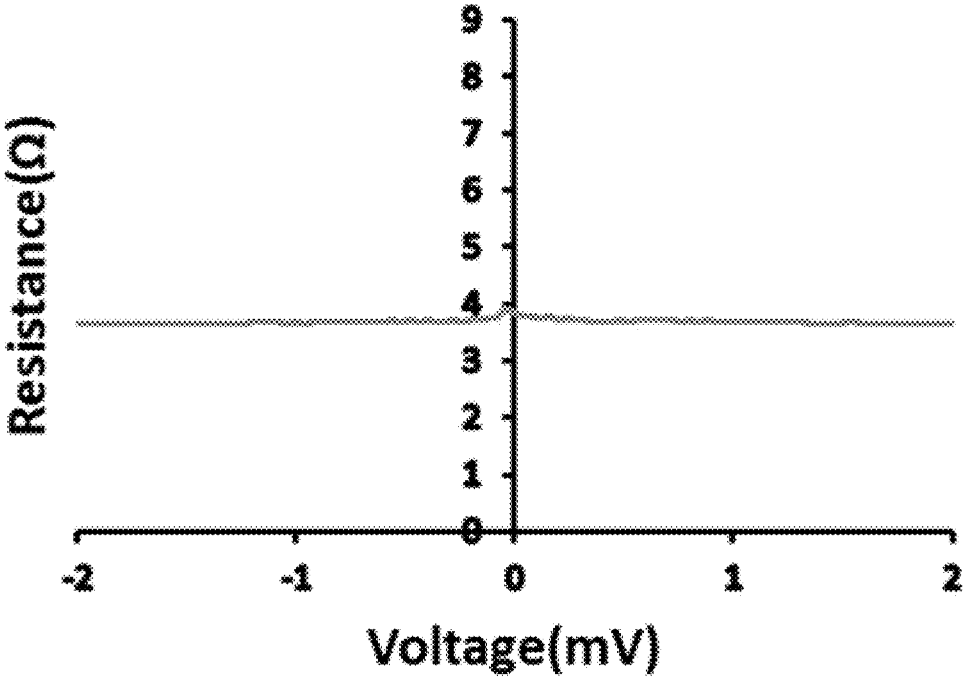
FIG. 5B illustrates a resistance versus voltage (R-V) spectrum for exemplary CNTs array of exemplary fabricated chip, consistent with one or more exemplary embodiments of the present disclosure.
Figure 5C:
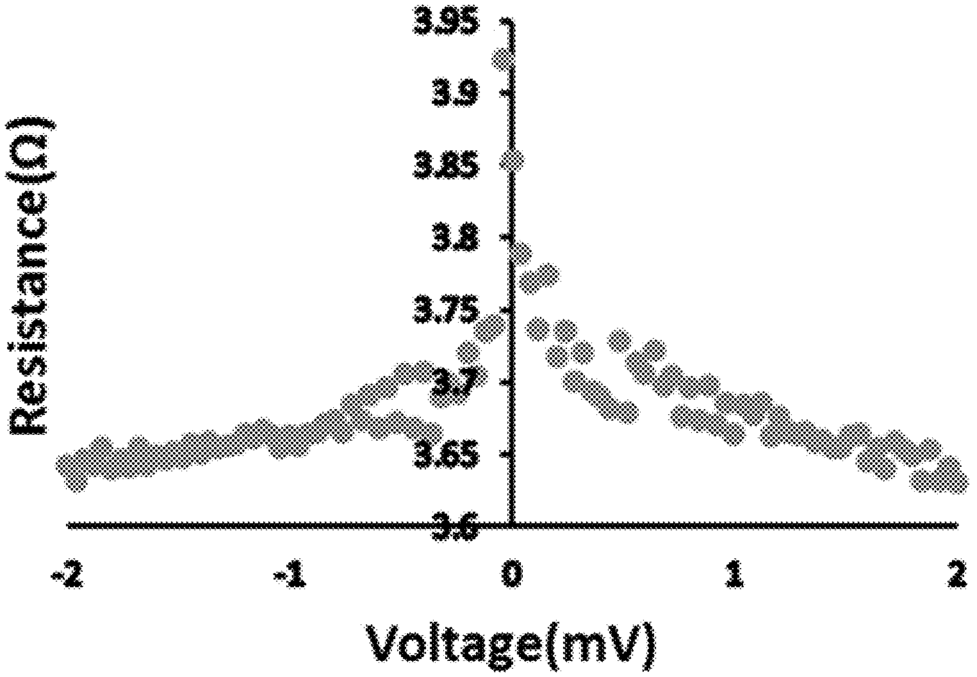
FIG. 5C illustrates resistance dots versus bias voltage for exemplary CNTs array of exemplary fabricated chip, consistent with one or more exemplary embodiments of the present disclosure.

Electrostatic Chargeability of VAMWCNT Arrays:

FIGS. 5A-5C show IV characterization of exemplary CNTs array at a width of sensor electrodes, consistent with one or more exemplary embodiments of the present disclosure. I-V plots (measured by Kithely 2361) extracted from the VAMWCNT arrays at the width of a CNT (70 μm), indicated the great conductivity of the nanotube arrays. FIG. 5A shows current versus voltage (I-V) diagram for exemplary CNTs array of exemplary fabricated chip, consistent with one or more exemplary embodiments of the present disclosure. A linear ohmic behavior may be observed for the CNTs array. FIG. 5B shows a resistance versus voltage (R-V) spectrum for exemplary CNTs array of exemplary fabricated chip, consistent with one or more exemplary embodiments of the present disclosure. The R-V spectrum shows an approximately constant value near 4Ω resistance in accordance with the I-V variations shown in FIG. 5A. FIG. 5C shows resistance dots versus bias voltage for exemplary CNTs array of exemplary fabricated chip, consistent with one or more exemplary embodiments of the present disclosure. The average resistance is about 3.68Ω. Linear current-voltage plot was observed for nanotube arrays (FIGS. 5A and 5B). The plots indicated that the resistance along the surface covered by nanotubes is around 3.6Ω (FIGS. 5B and 5C).

Investigating the Life Time of Charge Carries in CNT Structures:

The life time of electron in CNT covered $SiO_2$ surface was compared with bare $SiO_2$ layer. The results showed nearly three times greater life time as a result of the chargeable structures of nanotubes on the $SiO_2$ surface covered by CNTs in comparison with the bare $SiO_2$ layer.

The above electrical characteristics of CNTs may facilitate an achievement to induce perfect destruction on malignant cells due to the presence of further concentration of accumulated electrostatic charges.

Example 2: Effects of Electrostatic Stimulation Produced by Positive Charges on Normal, Primary Cancerous, and Metastatic Cells (In Vitro)

In this example, the effect of electrostatic stimulation produced by positive charges on normal, primary cancerous, and metastatic cells through exemplary method 100 by using exemplary chip 200 including an array of CNTs covered onto the substrate of exemplary chip 200 was investigated.

Three types of cell lines, including normal cell line (MCF-10A non-cancerous breast epithelial cell line), primary cancerous cell line (MCF-7 human breast cancer cell line), and metastatic cell line (MDA-MB-468 human breast cancer cell line) were obtained and cultured. The MDA-MB-468 and MCF-7 cells were cultured in Dulbecco's Modified Eagle Medium (DMEM) supplemented with about 10% Fetal Bovine Serum (FBS), about 1% antibiotic/antimitotic solution and about 0.2% $NaHCO_3$. The MCF-10A cell line was cultured in DMEM/F12 supplemented with about 10% horse serum, about 1% antibiotic/antimitotic solution, about 0.2% $NaHCO_3$, insulin (about 5 μg/ml), EGF (about 10 ng/ml) and Hydrocortisone (about 1 μg/ml). All cells were cultured in a humidified incubator at about 37° C. containing about 5% $CO_2$.

Figure 6:
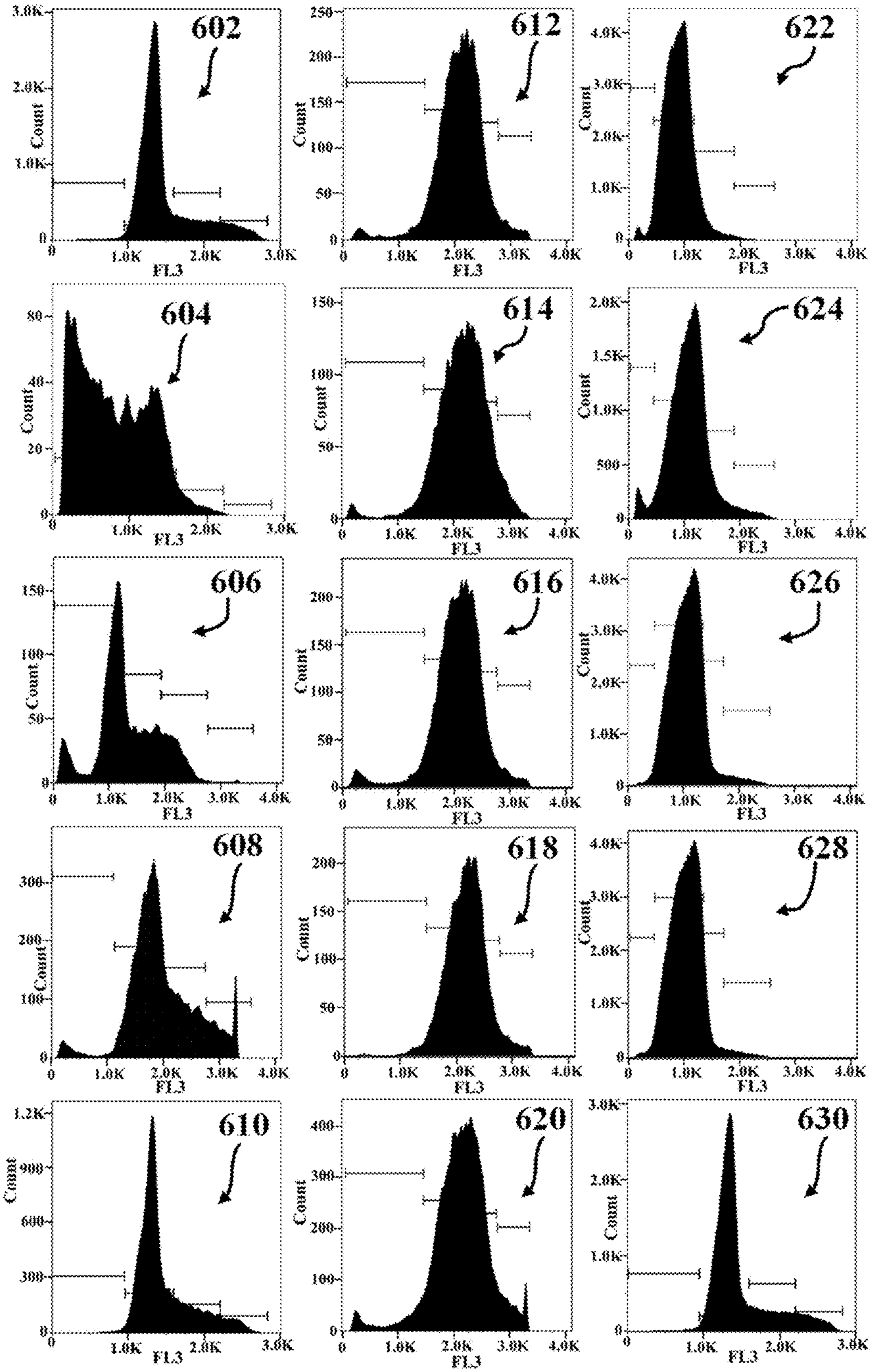
FIG. 6 illustrates cell cycle analysis of stimulated MCF7, MCF10, and MDAMB468 cell lines at different amounts of electrostatic field in comparison with non-stimulated control group for all three cell lines, consistent with one or more exemplary embodiments of the present disclosure.

Flow Cytometry Analysis:

First, the influence of continuous electrostatic stimulation (for about 24 hours) on the cell cycle was analyzed by flow cytometry. FIG. 6 shows cell cycle analysis of stimulated MCF7, MCF10, and MDAMB468 cell lines at different amounts of electrostatic field in comparison with non-stimulated control group for all three cell lines, consistent with one or more exemplary embodiments of the present disclosure. Shown results for MDAMB468 cell line include curve 602 for non-stimulated MDAMB468 cell line, curve 604 for stimulated MDAMB468 cell line with +6 V, curve 606 for stimulated MDAMB468 cell line with +3 V, curve 608 for stimulated MDAMB468 cell line with +1 V, and curve 610 for stimulated MDAMB468 cell line with −6 V. Results for MCF7 cell line include curve 612 for non-stimulated MCF7 cell line, curve 614 for stimulated MCF7 cell line with +6 V, curve 616 for stimulated MCF7 cell line with +3 V, curve 618 for stimulated MCF7 cell line with +1 V, and curve 620 for stimulated MCF7 cell line with −6 V. Results for MCF10 cell line include curve 622 for non-stimulated MCF10 cell line, curve 624 for stimulated MCF10 cell line with +6 V, curve 626 for stimulated MCF10 cell line with +3 V, curve 628 for stimulated MCF10 cell line with +1 V, and curve 630 for stimulated MCF10 cell line with −6 V. In addition, flowcytometric cell cycle analysis presented in FIG. 6 are summarized in TABLE 1.

Observable on data represented in FIG. 6 and TABLE 1, a great increase has been selectively seen on the apoptotic rates of metastatic cells compared to more normal ones. The results reveal no destructive effects of neither positive nor negative electrostatic stimulations on non-cancerous breast cell line (MCF10) (curves 624, 626, 628, and 630). Moreover, no temperature increment in the cell media was observed in stimulated cell lines. The rate of apoptotic cells (sub-G1 phase) was not significant in non-malignant cancerous breast cell lines (MCF7) exposed to positive electrostatic charges (curves 614, 616, and 618), while no changes were recorded in these cells stimulated by negative electrostatic charges (curve 620). However, it was observed that the apoptotic rate of metastatic cancer cells (MDA-MB-468) sharply increased (about 60%) after being exposed to positive charges with the potential of +6 V (curve 604). Slight but meaningful increase (about 25%) in apoptosis was measured by stimulating voltage of +3 V (curve 606). Electrostatic stimulation by negative charges did not induce any apoptotic effects on the metastatic cells (curve 610).

TABLE 1

Summary of the flowcytometric cell cycle analysis.

| | Control | +6 V | +3 V | +1 V | −6 V |
|---|---|---|---|---|---|
| MDA-MB-468 | | | | | |
| SubG1 % | 1.6 ± 0.4 | 62.2 ± 3.5 | 38 ± 3 | 4 ± 0.2 | 1.2 ± 0.2 |
| G1 % | 74.2 ± 2.5 | 35.5 ± 2.4 | 48 ± 2 | 52 ± 3.5 | 72.3 ± 3.2 |
| S % | 15.6 ± 1.5 | 4.04 ± 1.2 | 17 ± 3 | 30 ± 4 | 19.6 ± 2.8 |
| G2 % | 8.9 ± 1.4 | 0.04 ± 0.01 | 1 ± 0.2 | 12 ± 2.5 | 6.9 ± 1.4 |
| MCF7 | | | | | |
| SubG1 % | 5.7 ± 1.2 | 5.4 ± 1.2 | 7 ± 1.8 | 3 ± 0.6 | 7.1 ± 2.4 |
| G1 % | 48.2 ± 3.1 | 42.1 ± 3.4 | 49 ± 2 | 44 ± 2.5 | 42.6 ± 3.2 |
| S % | 41.8 ± 1.7 | 45.9 ± 2.3 | 40 ± 1.5 | 48 ± 2.1 | 43.1 ± 2.4 |
| G2 % | 4.2 ± 1.1 | 6.68 ± 1.3 | 4 ± 0.8 | 6 ± 0.8 | 7.6 ± 1.5 |
| MCF10A | | | | | |
| SubG1 % | 3.2 ± 1.6 | 4.15 ± 1.4 | 1.5 ± 0.2 | 2 ± 0.5 | 1.5 ± 0.3 |
| G1 % | 83.9 ± 2.6 | 55 ± 2.9 | 87 ± 4 | 88.1 ± 3.5 | 75.1 ± 4.7 |
| S % | 12.3 ± 1.7 | 36.7 ± 4.2 | 10 ± 1.5 | 9 ± 3.5 | 4.1 ± 0.7 |
| G2 % | 0.7 ± 0.1 | 3.4 ± 0.8 | 4 ± 1 | 2.5 ± 3.5 | 9.4 ± 1.5 |

Nitrite ($NO_2^-$) Detection:

Additionally, the effect of electrostatic stimulation on $NO^-_2$ production in normal and cancer cells was investigated. For assessment of the amount of $NO_2^-$ production, the Griess assay sulfanilamide and NED was employed under acidic conditions to record the accumulated nitrite ($NO_2^-$), which is a stable breakdown product of NO. During the assay, medium aliquots were mixed with equal volumes of the Griess reagent, and incubated at room temperature for about 15 minutes. To analyze the azo dye production, a spectrophotometer with absorbance set at 490 nm was used. Sodium nitrite was used as a standard.

Figure 7:
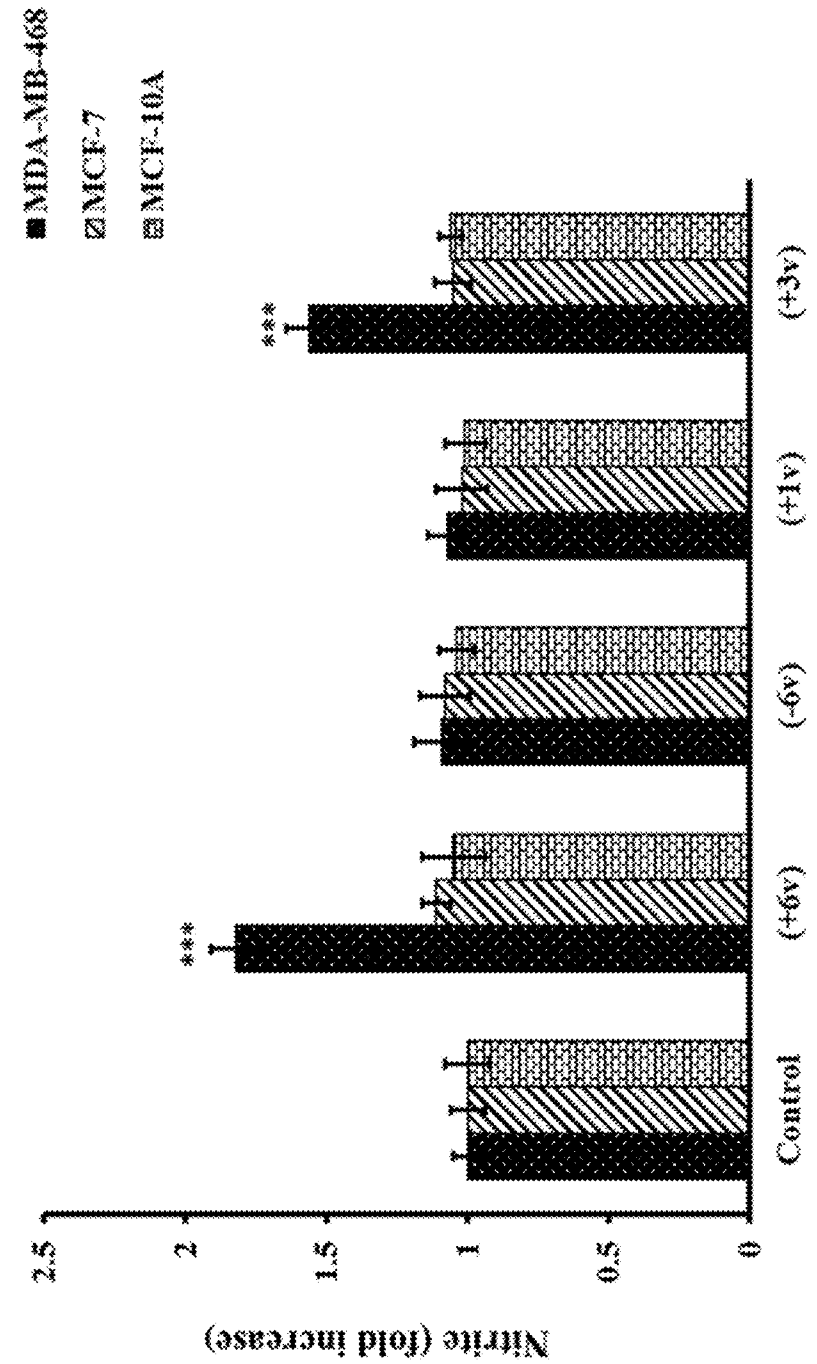
FIG. 7 illustrates Nitrite ion ($NO_2^-$) analysis results for stimulated MCF7, MCF10, and MDAMB468 cell lines, consistent with one or more exemplary embodiments of the present disclosure.

FIG. 7 shows Nitrite ion ($NO_2^-$) analysis results for stimulated MCF7, MCF10, and MDAMB468 cell lines, consistent with one or more exemplary embodiments of the present disclosure. An increase in $NO_2^-$ levels in cellular media can be a signal of increase on apoptotic levels. As observed in FIG. 7, greater $NO_2^-$ levels has been seen mostly on metastatic cells. It may be observed that in the presence of −6 V (high negative stimulation) and +1 V (low positive stimulation), the fold change in $NO_2^-$ production was not significant compared to the control group in all cell lines. However, in the presence of +6 V (high positive stimulation), the production of $NO_2^-$ significantly increased in MDA-MB-468 cells (1.8±0.3 fold compared to the control, 1.68±0.2 fold compared to −6V, and 1.73±0.25 fold compared to +1 V). The +6 V and +3 V stimulations had no considerable effects on $NO_2^-$ production in MCF-7 and MCF-10A cell lines.

Cell Vitality Assay:

Moreover, 3-(4,5-dimethylthiazol-2-yl)-2,5-diphenyltetrazolium bromide (MTT) assay was employed to declare the effect of electrostatic stimulation on cell growth in both breast non-malignant and malignant cells. The MCF-10A non-cancerous breast epithelial cell line, MCF-7 human breast cancer cell line, and MDA-MB-468 human breast cancer cell line were seeded in 12-well plates at a density of about $10^5$ cell/well in a final volume of about 500 μl. Cells were stimulated with different amounts of electrostatic field of 0 V (control cell lines), +6 V, −6 V, +1 V, and +3 V. After about 72 hours incubation, about 50 μl of the MTT solution (about 5 mg/ml) was added to each well. The cells were incubated at about 37° C. for about 3 hours. Then the medium was removed, and the insoluble formazan crystals were dissolved in about 500 μl of Dimethyl sulfoxide (DMSO). The absorbance was measured at 570 nm by Microplate Reader. The results were expressed as the percentage of cell growth relative to the control.

Figure 8:
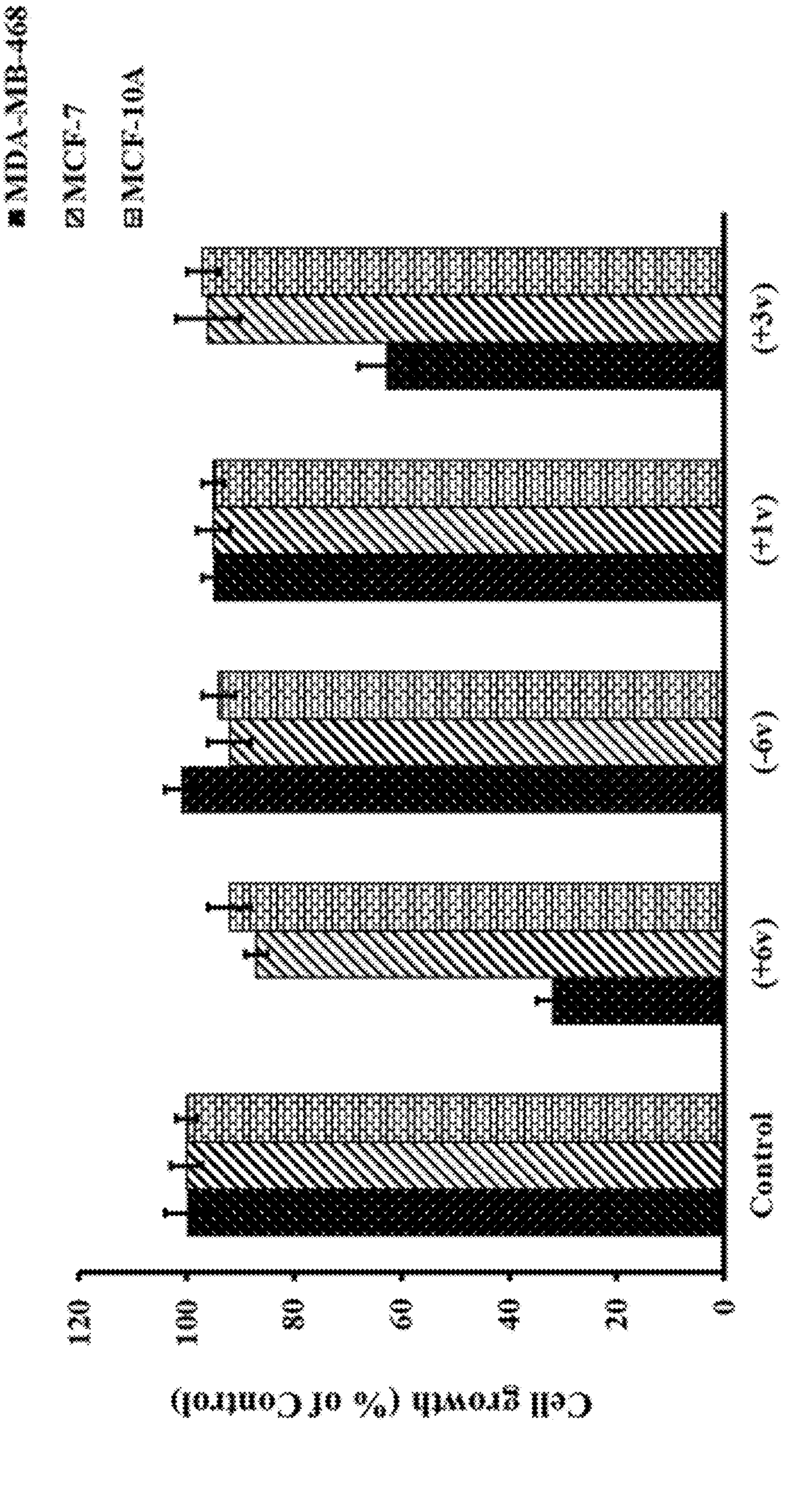
FIG. 8 illustrates MTT assay results for stimulated MCF7, MCF10, and MDAMB468 cell lines, consistent with one or more exemplary embodiments of the present disclosure.

FIG. 8 shows MTT assay results for stimulated MCF7, MCF10, and MDAMB468 cell lines, consistent with one or more exemplary embodiments of the present disclosure. It may be observed that MTT as a widespread viability assessment method has exhibited significant decrease on viability of stimulated metastatic cells, while for the other two groups of cells, such destructive effect was not observed.

Referring to FIG. 8, +3 V and +6 V stimulations significantly decreased cell growth in MDA-MB-468 cells with respect to control sample. In +6 V group, MDA-MB-468 cell growth decreased about 68%±3 compared to the control group, about 70%±2 compared to −6 V group, about 63%±2 compared to +1 V group, and about 30%±4 compared to +3 V group. It also may be observed that the +6 V stimulation had no meaningful effect on the growth of MCF-7 and MCF-10A cell lines.

Annexin/PI Analysis:

The rate of apoptosis in the post exposed cell lines were quantified via Annexin/PI assay. A meaningful shift of population into right of the obtained Annexin/PI analysis diagrams were observed in the stimulated metastatic cells, which has not occurred for the other stimulated groups of cells. This shift would be a signal of increase in early apoptotic rates meaning that a great destructive effect selectively on metastatic cells has been achieved.

Results of the Annexin/PI assay for control and positively stimulated cell lines are summarized in TABLE 2. The percent of cells at the different procedures of early and late apoptosis is exhibited. The overall increment of apoptotic levels on metastatic cells selectively, is observable with more reliance on early apoptosis increment. The results revealed negligible apoptotic induction of positive electrostatic charges on MCF10A (about 3% increase in apoptosis: 2% early and 1% late apoptosis) and MCF-7 (about 5% increase in apoptosis: 2.5% early and 2.5% late apoptosis) cells, while a strong apoptosis induction on metastatic MDA-MB-468 cells (about 47% increase in apoptosis: 29% early and 18% late apoptosis) was observed.

TABLE 2

Annexin/Pi analysis results done for control and positively stimulated samples.

| | Control | +6 V |
|---|---|---|
| MDA-MB-468 | | |
| Viable cells % | 86 ± 2 | 52 ± 2 |
| Early Apoptosis % | 4 ± 1 | 29 ± 1 |
| Late Apoptosis % | 9 ± 2 | 18 ± 3 |
| Necrosis % | 1 ± 0.4 | 1 ± 0.3 |
| MCF7 | | |
| Viable cells % | 97 ± 1 | 87 ± 2 |
| Early Apoptosis % | 1 ± 0.4 | 2.5 ± 0.5 |
| Late Apoptosis % | 1 ± 0.2 | 2.5 ± 0.3 |
| Necrosis % | 1 ± 0.4 | 8 ± 0.3 |
| MCF10A | | |
| Viable cells % | 98 ± 2 | 96 ± 1 |
| Early Apoptosis % | 0.5 ± 0.1 | 2 ± 0.3 |
| Late Apoptosis % | 0.5 ± 0.2 | 1 ± 0.4 |
| Necrosis % | 1 ± 0.3 | 1 ± 0.2 |

Western Blot Assay:

To clarify the mechanism of selective cell-death induction in malignant cells by positive electrostatic stimulation, the expression changes of the apoptotic proteins (Bax, caspase3, caspase9, and anti-apoptotic ones (Bcl2)) in the post stimulated cells were assayed by western blot. The densities of Bax/Bcl2, Pro-caspase3 and Pro-caspase9 expressions were measured, and the ratio to β-actin was calculated. The results are summarized in TABLE 3.

Referring to TABLE 3, it may be observed that under +6 V electrostatic stimulation, the MDA-MB-468 cells induced a significant increase (about 2.4 fold) of Bax/Bcl2 ratio compared to MCF7 cell line. Moreover, it was found that the expression of the pro-caspase9 protein in post stimulated MDA-MB468 cells was decreased about 1.4 fold compared to MCF7 cells. Although, the post stimulation dependent expression of pro-caspase3 showed a significant increase in the MDA-MB-468 cells, and no expression change was observed in post stimulated MCF7 cells. Expression results on apoptotic proteins delineated that positive electrostatic stimulation resulted in the augmentation of the Bax/Bcl2 ratio and significant decrease of pro-caspase3 and 9 in the MDA-MB-468 cells which all indicated the occurrence of internal apoptosis in post stimulated malignant breast cells. On the other hand, it seems that the early apoptosis had begun in the MCF-7 cells, due to the increase of Bax/Bcl2 ratio and decrease of pro-caspase9, but it hadn't induce complete apoptosis as no expressing changes in the level of pro-caspase3 proteins was occurred.

TABLE 3

Annexin/Pi analysis results done for control and positively stimulated samples.

| | Control | ±6 V |
|---|---|---|
| MCF-7 | | |
| Bax/Bcl-2 Ratio (Arbitrary Unit) | 0 ± 0.002 | 0.21 ± 0.2** |
| Pro-caspase3/β-actin (Arbitrary Unit) | 1.01 ± 0.03 | 0.98 ± 0.03 |
| Pro-caspase9/β-actin (Arbitrary Unit) | 0.8 ± 0.03 | 0.21 ± 0.06*** |
| MDA-MB-468 | | |
| Bax/Bcl-2 Ratio (Arbitrary Unit) | 0 ± 0.001 | 0.51 ± 0.02*** |
| Pro-caspase3/β-actin (Arbitrary Unit) | 1.4 ± 0.05 | 0.96 ± 0.02*** |
| Pro-caspase9/β-actin (Arbitrary Unit) | 0.92 ± 0.04 | 0.14 ± 0.02*** |

Figure 9A:
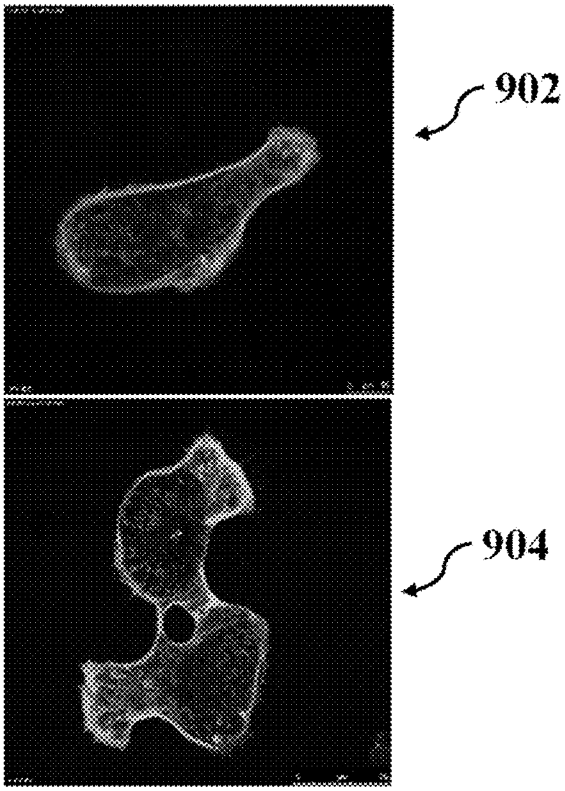
FIG. 9A illustrates confocal microscopy images of MCF10 cell lines in control (top side) and positively stimulated by +6 V for about 24 hours (bottom side), consistent with one or more exemplary embodiments of the present disclosure.
Figure 9B:
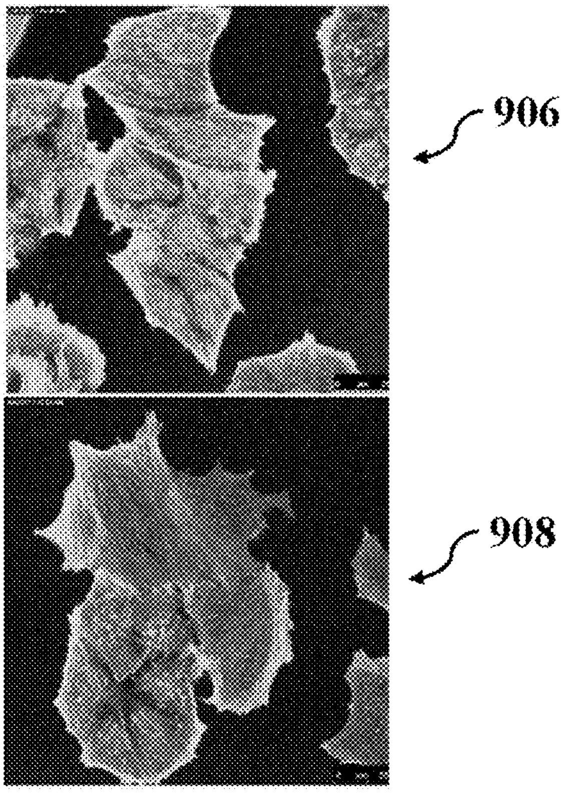
FIG. 9B illustrates confocal microscopy images of MCF7 cell lines in control (top side) and positively stimulated by +6 V for about 24 hours (bottom side), consistent with one or more exemplary embodiments of the present disclosure.
Figure 9C:
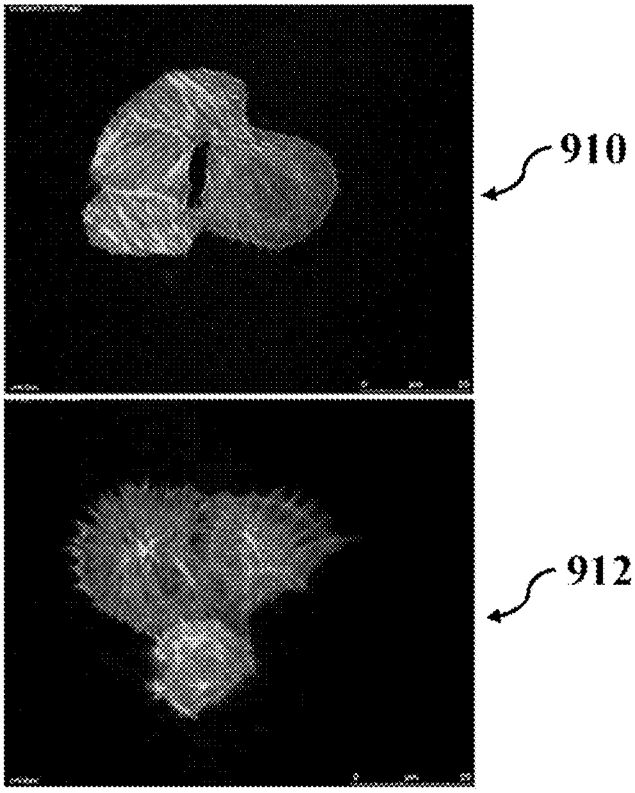
FIG. 9C illustrates confocal microscopy images of MDA-MB-468 cell lines in control (top side) and positively stimulated by +6 V for about 24 hours (bottom side), consistent with one or more exemplary embodiments of the present disclosure.

Confocal Imaging:

Furthermore, actin assembly in the normal and malignant cells which had been exposed to positive electrostatic charges (+6 V) was investigated. FIGS. 9A-9C show confocal microscopy images of MCF10, MCF7, and MDA-MB-468 cell lines in control (top side) and positively stimulated by +6 V for about 24 hours (bottom side), consistent with one or more exemplary embodiments of the present disclosure. A significant change of course in direction of tension in Actin filaments is observable in exposed metastatic cells compared to their control.

Referring to FIGS. 9A-9C, confocal images taken from the cells before and after the stimulation showed that the post exposed MCF10 cells (image 904 of FIG. 9A) and MCF-7 cells (image 908 of FIG. 9B) exhibited no noticeable changes in their actin modeling and distribution in comparison with their control group of images 902 (FIG. 9A), and 906 (FIG. 9B), respectively. Hence, their adhesion and accordingly proliferation on the substrate were maintained. In contrast, malignant cells MDA-MB-468 exhibited remodeled actins with an extreme tendency to retract the cell (image 912 of FIG. 9C) through the source of positive electrostatic charges against cell proliferation on the substrate compared with the control non-stimulated cell line (image 910 of FIG. 9C). The assembly of actin-filopodia through the CNT-covered chip induced detachment from the surface, activation of internal apoptotic pathways and cell death in malignant cells.

Example 3: In-Vivo Inhibition of Mammary Tumor Growth

In this example, the effect of electrostatic stimulation produced by positive charges on normal, primary cancerous, and metastatic cells through exemplary method 100 by using exemplary chip 200 including an array of CNTs covered onto the substrate of exemplary chip 200 was investigated.

To determine if external application of positive electrostatic stimulation would suppress tumor growth in-vivo, $2.3\times10^6$ 4T1-derived cancer cells were implanted into the back of female BALB/C mice, and the mice were maintained in individual groups with similar size of formed tumors. Exemplary chip 200 including CNT covered silicon substrates was externally attached as an exemplary electrically conductive patch on top of mice's skin over the location of tumors by biological tapes (anti allergic surgical tape). The interface between the patch and the skin was filled by a thin layer of Polydimethylsiloxane (PDMS) as biocompatible electrical insulator layer to prevent current flow between the patch and the body of the mice. The patches were biased to +12 V and +32 V DC positive electrical potentials (chosen as low and high voltages applied to the selected groups of individual mice) generated by a DC electrical power generator. Under body of the mice was connected to ground potential. The positive charges accumulated on the CNTs, approximately at/close to their interface with skin, applied attractive electrostatic stimulation to the tumor. Significantly suppressed tumor growth was found in mice who were connected to positively charged patches on their tumor region compared with non-charged controls as could be observed in their sonography images.

Figure 10A:
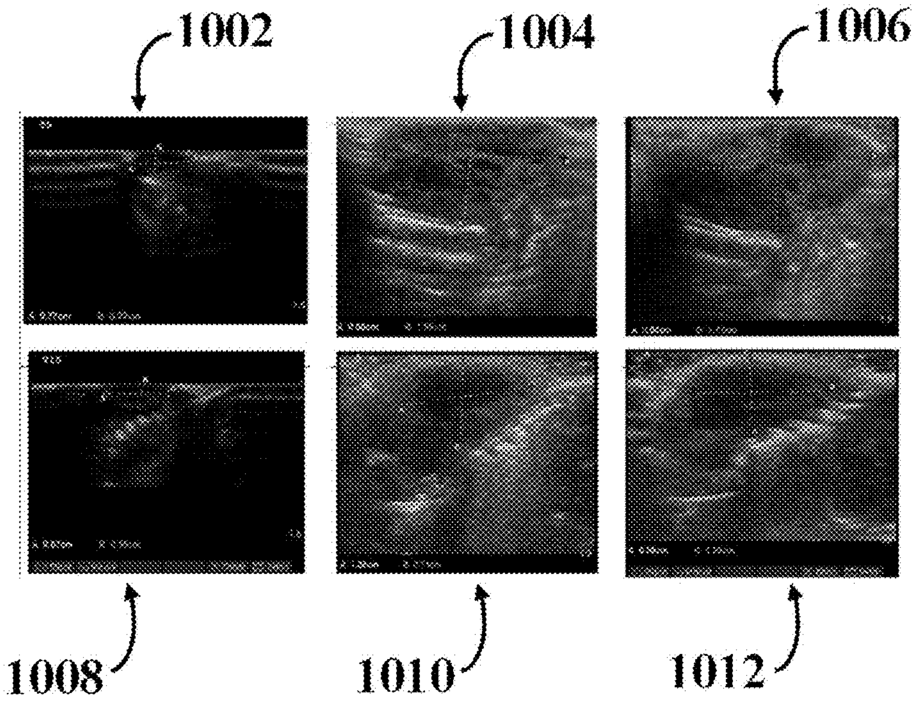
FIG. 10A illustrates sonography images of tumors of control and exposed mice to positively charged patches with 12 V intensity after a $1^{st}$ day, s $10^{th}$ day, and a $25^{th}$ day, consistent with one or more exemplary embodiments of the present disclosure.
Figure 10B:
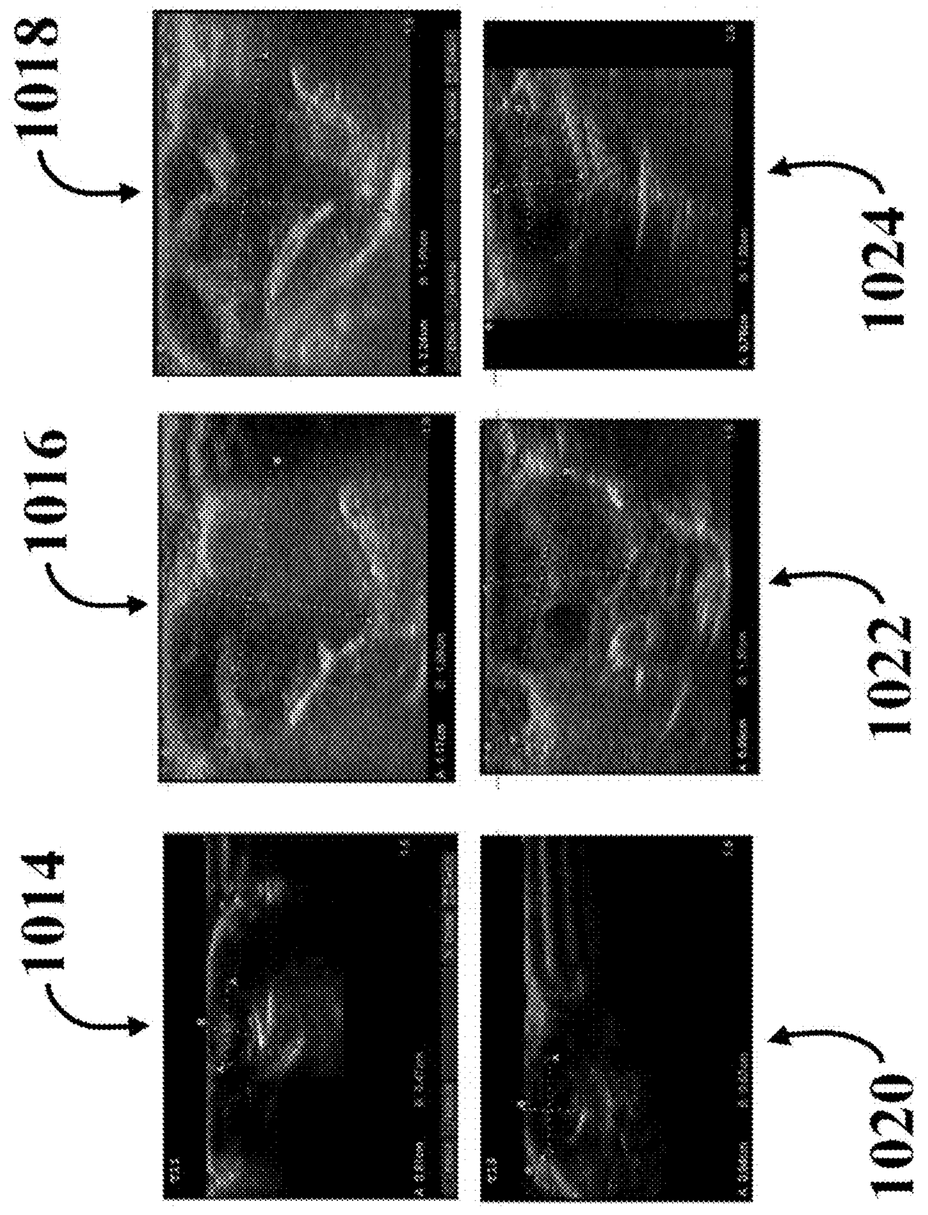
FIG. 10B illustrates sonography images of tumors of control mice and exposed mice to positively charged patches with 32 V intensity after a $1^{st}$ day, a $10^{th}$ day, and a $25^{th}$ day, consistent with one or more exemplary embodiments of the present disclosure.

FIG. 10A shows sonography images of tumors of control mice (images 1002, 1004, and 1006) and exposed mice to positively charged patches with 12 V intensity (images 1008, 1010, and 1012) after a $1^{st}$ day (images 1002 and 1008), a $10^{th}$ day (images 1004 and 1010), and a $25^{th}$ day (images 1006 and 1012), consistent with one or more exemplary embodiments of the present disclosure. FIG. 10B shows sonography images of the tumors of control mice (images 1014, 1016, and 1018) and exposed mice to positively charged patches with 32 V intensity (images 1020, 1022, and 1024) after a $1^{st}$ day (images 1014 and 1020), a $10^{th}$ day (images 1016 and 1022), and a $25^{th}$ day (images 1018 and 1024), consistent with one or more exemplary embodiments of the present disclosure.

Referring to FIGS. 10A and 10B, significant tumor growth inhibition in size is observable for exposed mice compared to control ones. Higher levels of inhibition have been observed for more intense exposures. The tumor sizes were about 48.2% smaller at $25^{th}$ day of exposing to charged CNT Patch (+12 V) (image 1012) in comparison to the control samples (image 1006) (p=0.038) meanwhile they had similar size before start of electrostatic therapy (ET). Tumor growth inhibition observed after 25 days of ET was about 79.5% among mice connected to the patches stimulated by about three times higher (+32 V) voltage (image 1024) in comparison to the control samples (image 1018) (P=0.017).

Additional mice were connected to non-charged VACNT (electrically neutral CNTs) array for a longer duration of time (35 days). Results showed no effect of charged-free CNTs on tumor growth inhibition similar to control samples (P>0.05). Moreover, no tumor suppression was observed in mice connected to negatively charged VACNT patch (−32 V DC), similar to the results observed for breast cell lines in EXAMPLE 2 hereinabove. All obtained results are summarized in TABLE 4.

TABLE 4

Tumor size measurements in exposed and control mice.

| Mice ID. | Treating procedure | Tumor size before treat ($mm^2$) | Tumor size $10^{th}$ days of treat ($mm^2$) | Tumor size $25^{th}$ days of treat ($mm^2$) |
|---|---|---|---|---|
| T8 | Control for T9 | 45 | 76 | 129 |
| T9 | −32 V (continues) | 51 | 80 | 134 |
| T10 | Control for T11-T17 | 53 | 82 | 138 |
| T11 | +12 (continues) | 48 | 55 | 69 |
| T12 | +32 (continues) | 42 | 40 | 31 |
| T13 | +12 (10 hr per day) | 47 | 60 | 88 |
| T14 | +32 (10 hr per day) | 52 | 68 | 74 |
| T15 | +12 (5 hr per day) | 44 | 65 | 90 |
| T16 | +32 (5 hr per day) | 40 | 63 | 77 |
| T17 | −32 (5 hr per day) | 51 | 80 | 122 |

To further clarify the impact of charges density accumulated on CNTs in tumor growth suppression, tumor growth inhibition effects of non-CNT grown conductive silicon patch covered only by a Ni catalyst layer and stimulated by positive potential (+12 V) was compared with conductive silicon patch coated by a CNT layer. Tumor growth inhibition factor of the Ni patch was about 55% less than that of CNT-coated patch after 25 days. This was in direct correlation with further orders of accumulated charges on CNT surface with respect to Ni surface under similar electrostatic stimulation.

To ensure from the effect of electrostatic stimulation, charge free patches including Ni-covered Si Wafer (CNT-free) and CNT-grown Si wafer were applied on mice to compare the effect of charge free patches. TABLE 5 represents the effect of non-charged patches, which didn't induce any destruction on the tumor.

TABLE 5

Monitoring the tumor size in the mice received Ni and CNT patches non-connected to stimulating voltage (charge free).

| Mice No. | Status | Tumor surface size in $1^{st}$ Day of monitoring ($cm^2$) | Tumor surface size $25^{th}$ Day of monitoring ($cm^2$) |
|---|---|---|---|
| T20 | CONTROL | 0.74 × 0.56 | 1.81 × 1.11 |
| T21 | connected to Ni Wafer (CNT-free) without voltage | 0.63 × 0.44 | 1.15 × 1.17 |
| T22 | CONTROL | 0.91 × 0.66 | 1.85 × 1.91 |
| T23 | connected to CNT without Voltage | 0.83 × 0.4 | 1.43 × 1.32 |
| T24 | connected to Ni Wafer (CNT-free) without voltage | 0.61 × 0.47 | 1.36 × 1.13 |
| T25 | CONTROL | 0.47 × 0.51 | 1.13 × 1.38 |
| T26 | connected to CNT without Voltage | 0.82 × 0.31 | 1.14 × 1.23 |

Cytopathological and Immunohistochemical Analyses:

To deeply evaluate any probable induction of positive electrostatic charges on malignant and normal tissues of the mice, hematoxylin & eosin (H&E) and immunohistochemistry (IHC) assays were conducted on exposed and non-exposed regions of cancerous and normal tissues of the mice.

Figure 11A:
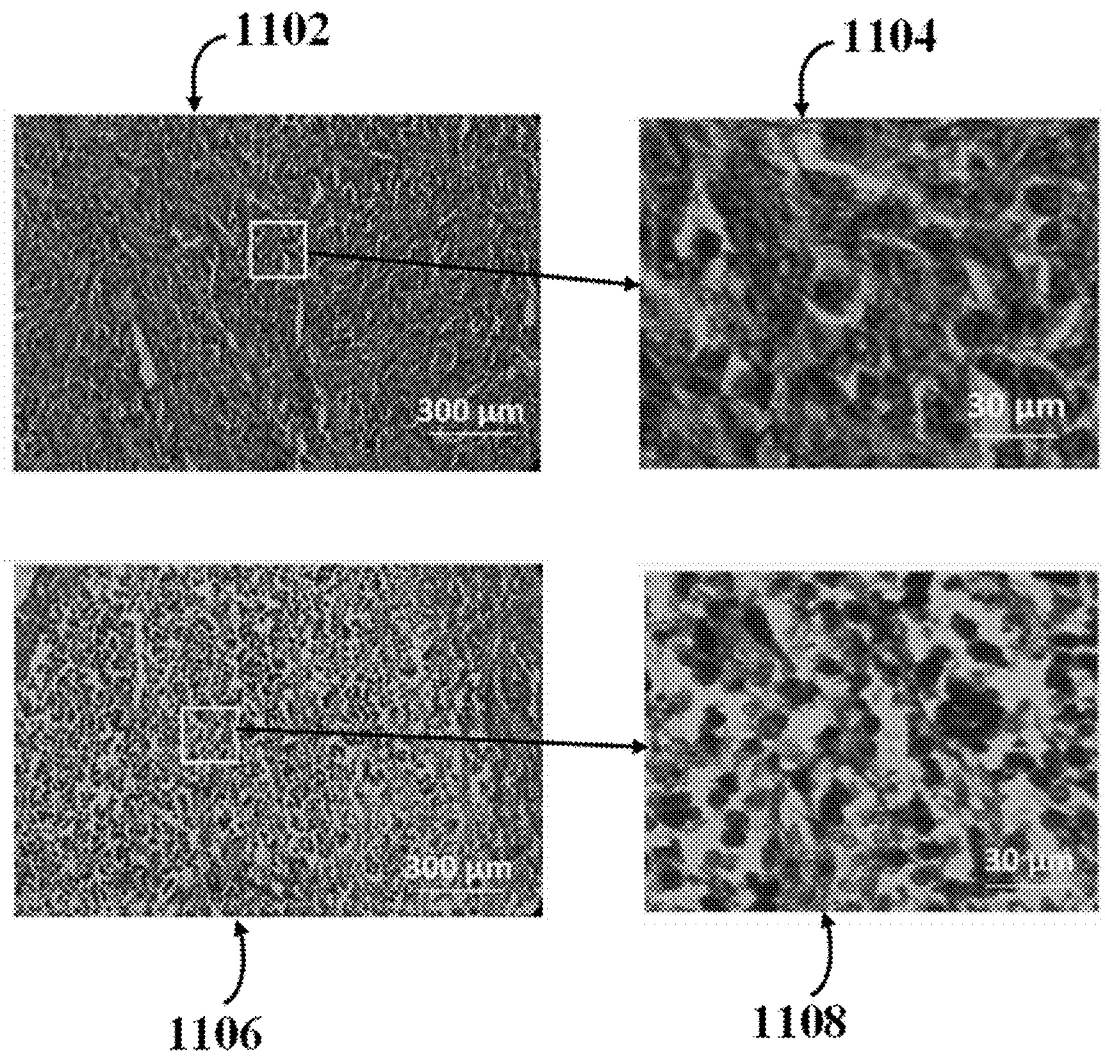
FIG. 11A illustrates H&E images for control (top side images) and exposed tumors to +32 V electrostatic stimulation (bottom side images), consistent with one or more exemplary embodiments of the present disclosure.
Figure 11B:
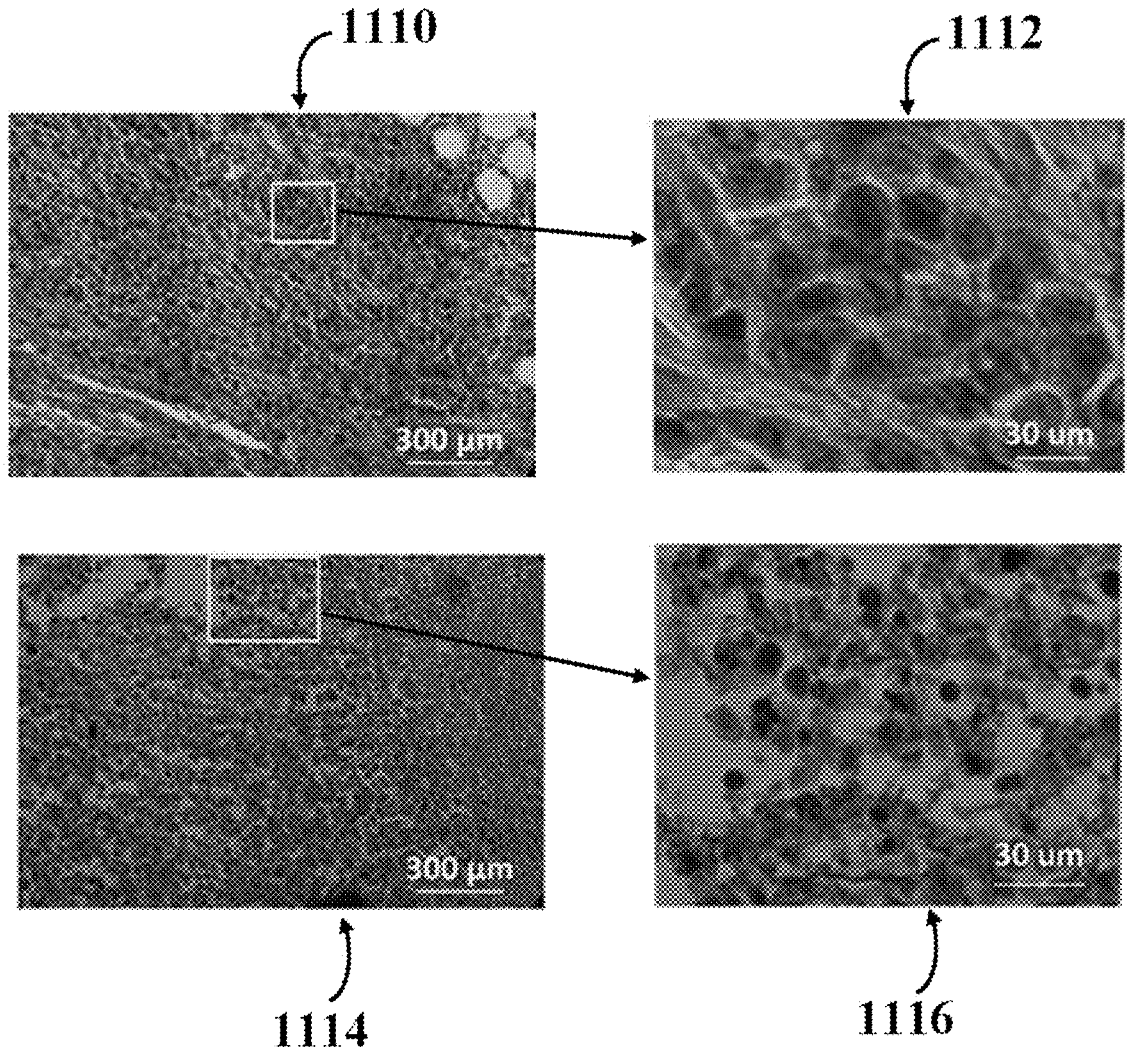
FIG. 11B illustrates H&E images for control (top side images) and exposed tumors to +12 V electrostatic stimulation (bottom side images), consistent with one or more exemplary embodiments of the present disclosure.

FIG. 11A shows H&E images for control (top side images 1102 and 1104) and exposed tumors to +32 V electrostatic stimulation (bottom side images 1106 and 1108), consistent with one or more exemplary embodiments of the present disclosure. FIG. 11B shows H&E images for control (top side images 1110 and 1112) and exposed tumors to +12 V electrostatic stimulation (bottom side images 1114 and 1116), consistent with one or more exemplary embodiments of the present disclosure. Apoptotic cells due to treatment by electrostatic stimulation could be distinguished due to their pykontic nuclei. Tumor destruction may be sharply observed in the in the regions exposed by +12 V and +32 V. In tumors treated by +12 V and +32 V for 25 days, the malignant cells were destructed and apoptotic cells could be observed in all-over the stained tissue. Moreover, some highly condensed nuclei, so-called pyknotic nuclei, are regarded as apoptotic cells in which the voltage dependent electrostatic stimulation activated the internal apoptotic pathways. Degraded cytoplasmic regions are so sharper in malignant tissues exposed by higher voltage (+32 V) of electrostatic exposure. As the tissue matrix was maintained in treated regions of the tumors, any probability about necrosis was excluded. On the other hand, non-treated tumor tissues could be distinguished by their hyper chromatic and irregular nucleus as well as increased nucleus/cytoplasm (N/C) ratio. Hence, the characteristic H&E staining pattern of nuclei gave indications of apoptosis in tumors treated by positive electrostatic charges.

Figure 11C:
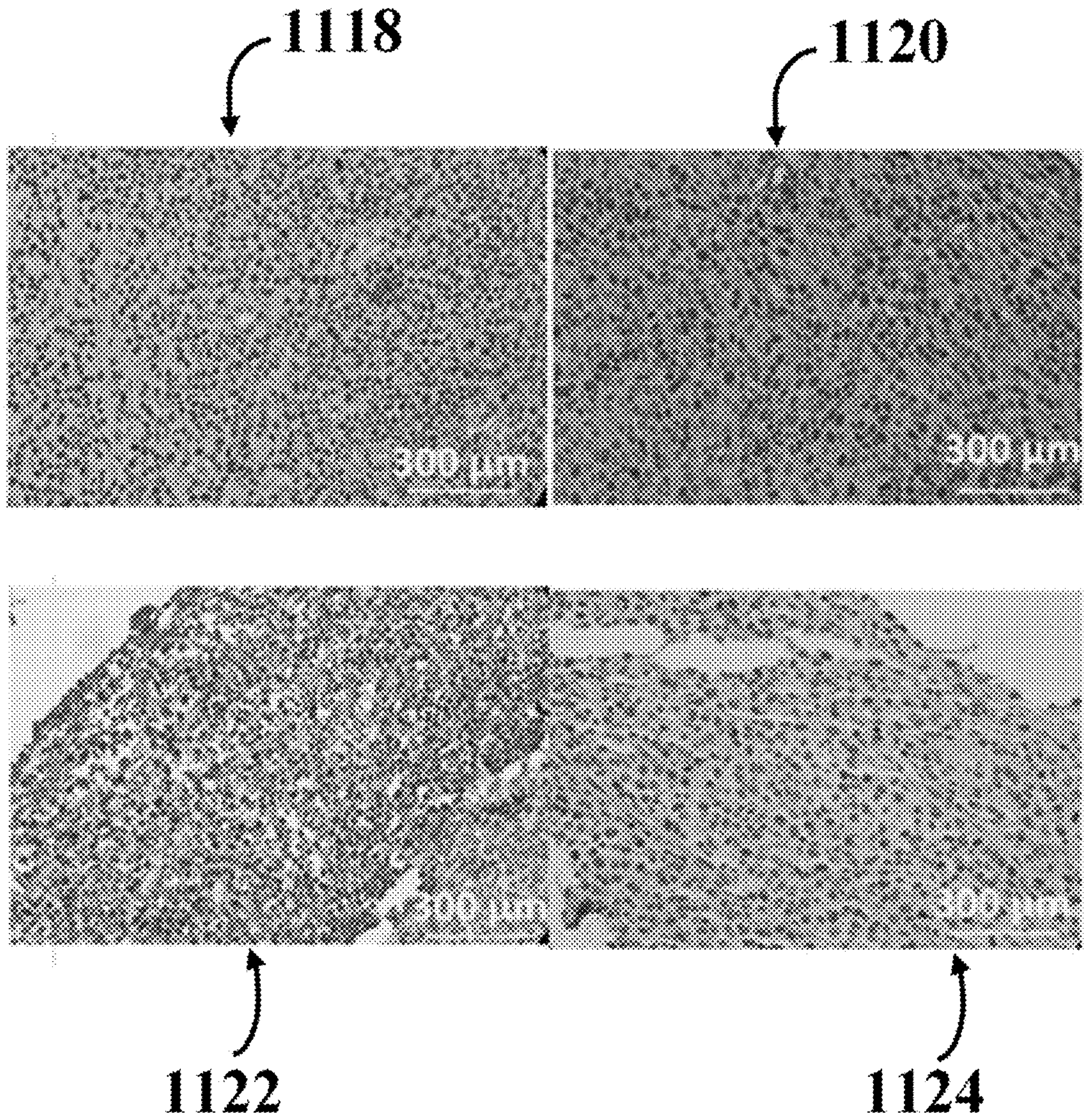
FIG. 11C illustrates IHC resulted images for control (top side images) and exposed tumors to +32 V electrostatic stimulation (bottom side images), consistent with one or more exemplary embodiments of the present disclosure.
Figure 11D:
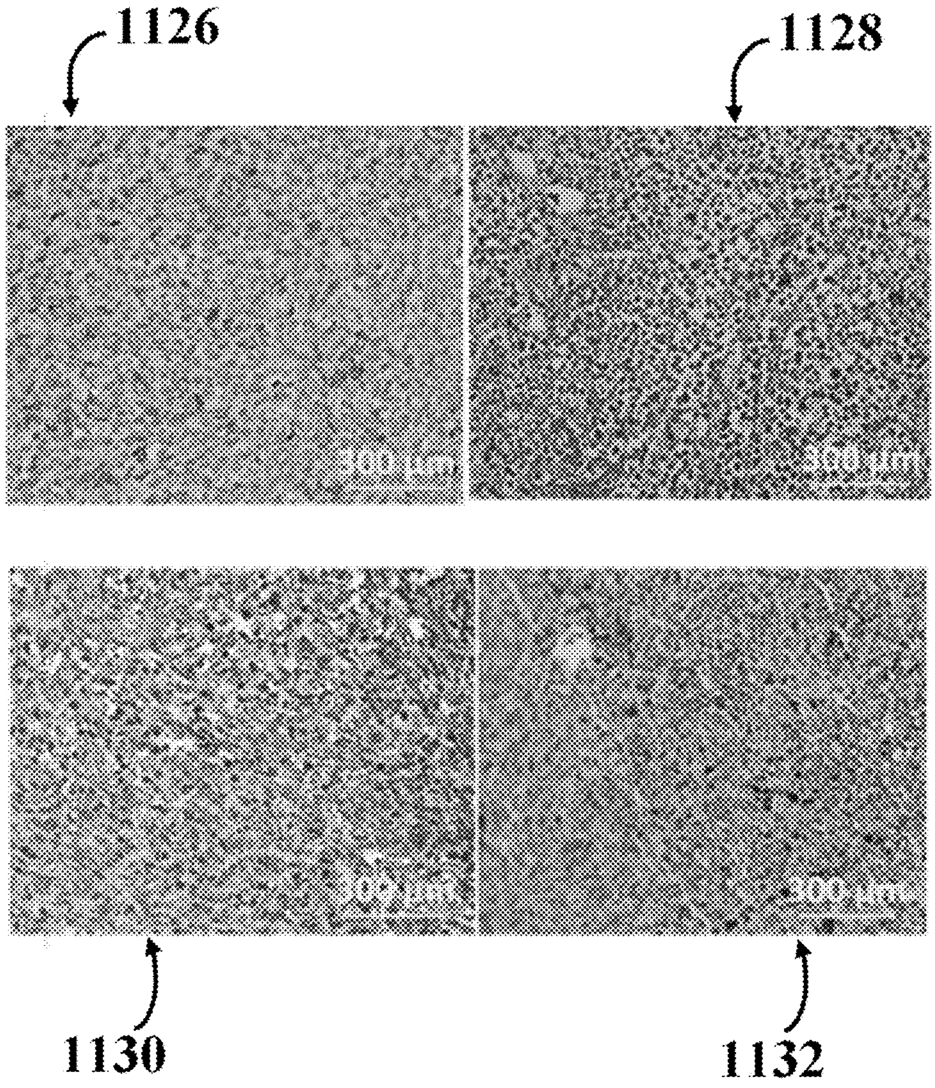
FIG. 11D illustrates IHC resulted images for control (top side images) and exposed tumors to +12 V electrostatic stimulation (bottom side images), consistent with one or more exemplary embodiments of the present disclosure.

To confirm suppressed proliferation and apoptotic induction in treated tumor cells, assays P53 as apoptotic immunomarker and KI67 as proliferative immunomarker were done using IHC. FIG. 11C shows IHC resulted images for control (top side images 1118 and 1120) and exposed tumors to +32 V electrostatic stimulation (bottom side images 1122 and 1124), consistent with one or more exemplary embodiments of the present disclosure. Left side images include P53 apoptotic immunomarker assay results (images 1118 and 1122) and right side images include KI67 proliferative immunomarker assay results (images 1120 and 1124). In addition, FIG. 11D shows IHC resulted images for control (top side images 1126 and 1128) and exposed tumors to +12 V electrostatic stimulation (bottom side images 1130 and 1132), consistent with one or more exemplary embodiments of the present disclosure. Left side images include P53 apoptotic immunomarker assay results (images 1126 and 1130) and right side images include KI67 proliferative immunomarker assay results (images 1128 and 1132). IHC staining of control and treated regions revealed the overexpression of P53 and Ki67 in treated and control regions, respectively. Post stimulated tumoral regions, greatly expressed the P53 meanwhile KI67 was just sharply expressed among non-exposed tumoral regions.

Figure 12A:
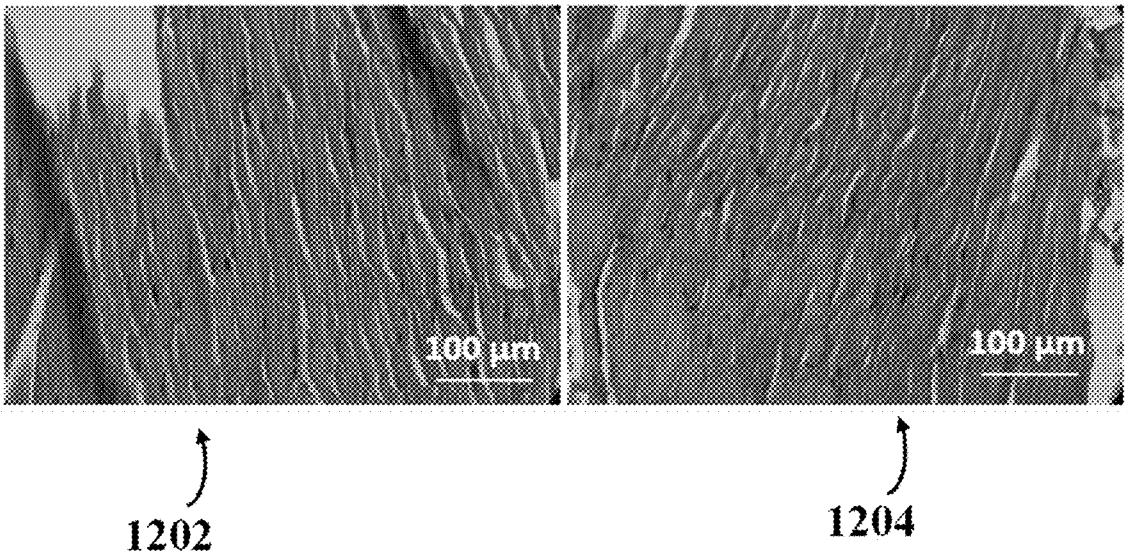
FIG. 12A illustrates H&E images of cytopathological analysis for an exposed region to +32 V electrostatic stimulation in comparison with a corresponding control region of a muscle in normal body tissues, consistent with one or more exemplary embodiments of the present disclosure.
Figure 12B:
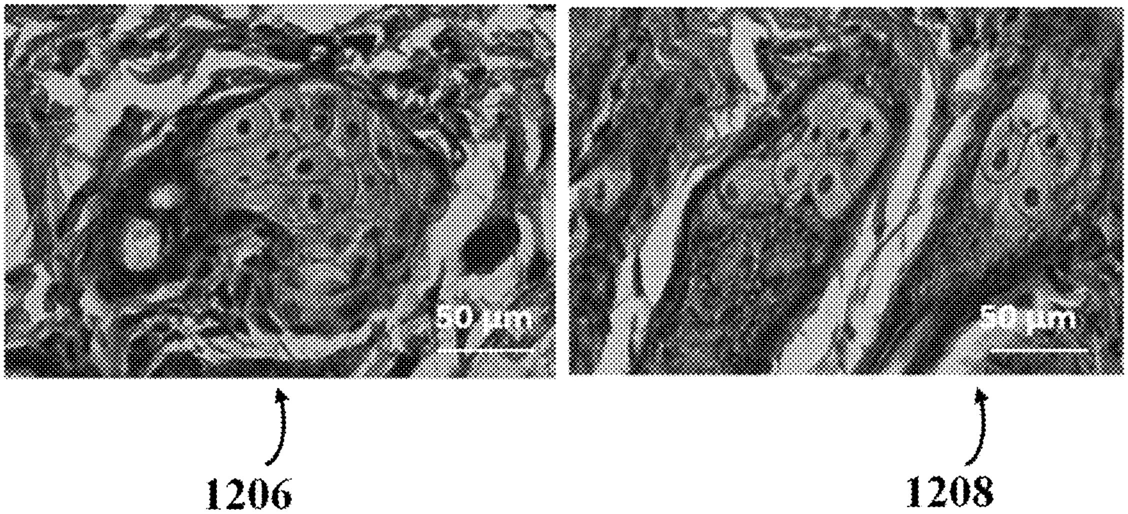
FIG. 12B illustrates H&E images of cytopathological analysis for an exposed region to +32 V electrostatic stimulation in comparison with a corresponding control region of skin in normal body tissues, consistent with one or more exemplary embodiments of the present disclosure.

FIG. 12A shows H&E images of cytopathological analysis for an exposed region 1202 of the muscle to +32 V electrostatic stimulation in comparison with a corresponding control region 1204 of the muscle in normal body tissues, consistent with one or more exemplary embodiments of the present disclosure. Moreover, FIG. 12B shows H&E images of cytopathological analysis for an exposed region 1206 of the skin to +32 V electrostatic stimulation in comparison with a corresponding control region 1208 of the skin in normal body tissues, consistent with one or more exemplary embodiments of the present disclosure. It may be observed that no trace of apoptosis or necrosis were observed in exposed regions by positive electrostatic induction. Cells maintained at their natural morphology and assemblies. Neither destruction nor any pathological signs were observed in H&E of skin and muscle tissues in all of the treated mice. This revealed the safety of electrostatic stimulation for normal cells without any induction on their morphology, natural proliferation and vitality pathways same as had been observed in MCF-10 cell lines in EXAMPLE 2 hereinabove. Therefore, the possibility of any cross-talk between tumor destruction and normal metabolism of healthy tissues neighbored by tumor cells were excluded.

Figure 13:
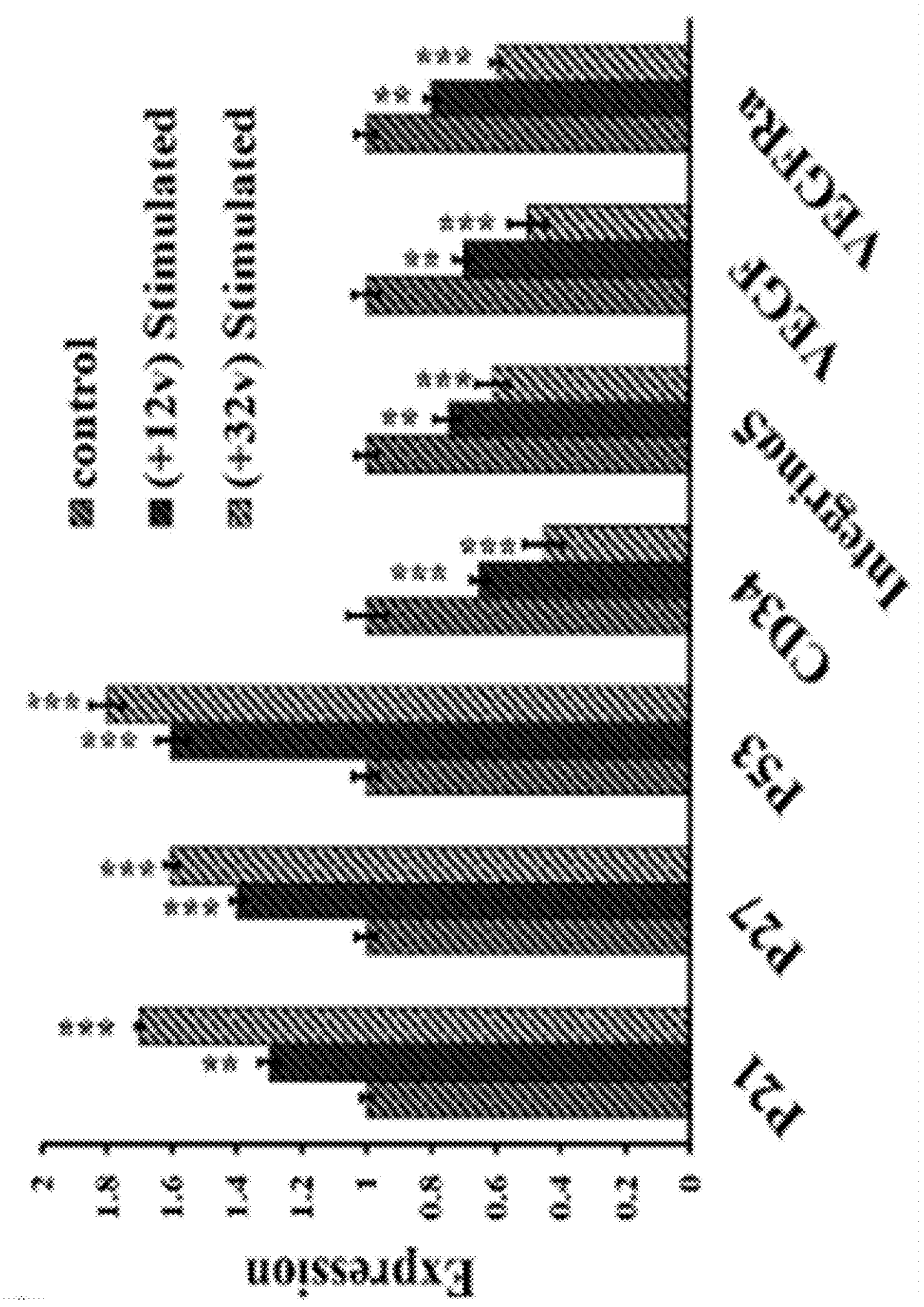
FIG. 13 illustrates RT-PCR results for 21 malignant mice categorized in three groups of control, treated by +12 V, and treated by +32 V, consistent with one or more exemplary embodiments of the present disclosure.

RT-PCR Analysis:

Furthermore, expression of adhesion, angiogenesis and cell cycle arrest related genes via quantitative real-time polymerase chain reaction (RT-PCR) were determined in 20 post exposed and control mice categorized in three groups, including control, treated by +12 V, and treated by +32 V. FIG. 13 shows RT-PCR results for 20 malignant mice categorized in three groups of control, treated by +12 V and treated by +32 V, consistent with one or more exemplary embodiments of the present disclosure. Overexpression of P21, P27 and P53 near downregulation of CD33, Integrin5, VEGF and VEGFRa in treated groups indicated that the electrostatic stimulation induced detachment followed by apoptosis in malignant tumor. This analysis revealed that P21, P16 and P53 genes (as apoptosis related transcriptomes) were up-regulated just in post exposed tumor with direct correlation with the intensity of positive charges. Moreover, integrin5α, VEGF, VEGFR, CD34 genes (as adhesion and spreading associated transcriptomes) were down-regulated in that tumors.

Example 4: Investigation of Apoptotic Induction of Positive Electrostatic Charges on a Twin Shaped Tumor In this example, to better evaluate the apoptotic induction of positive electrostatic charges on malignant cells, a twin shaped tumor in one mouse was tested. One hump was exposed to the positively charged CNT patch (+32 V) while other hump maintained free from any electrostatic stimulation.

Figure 14:
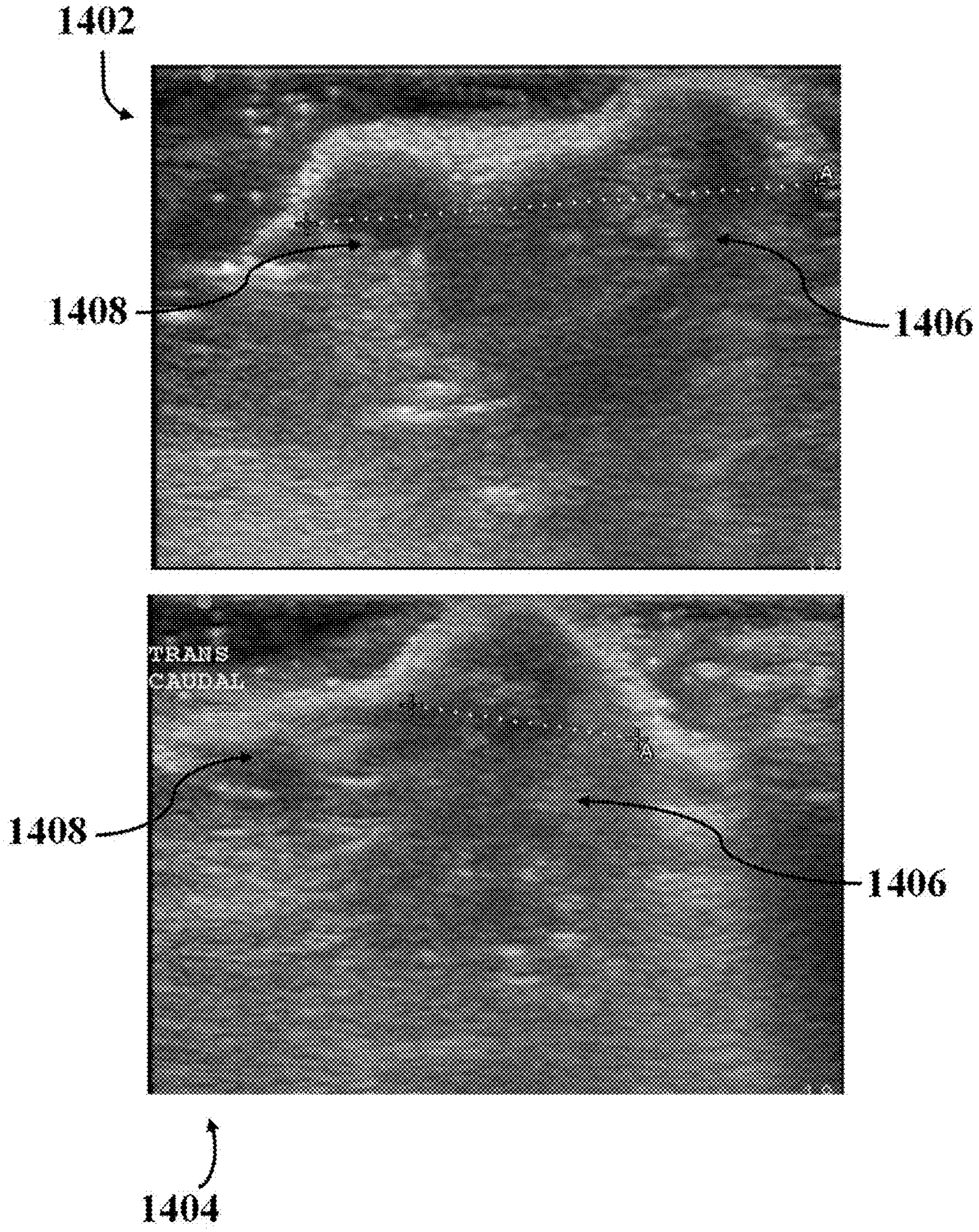
FIG. 14 illustrates sonography images of twin shaped tumor half of which was exposed to positive electrostatic stimulation (+32 V) at start of exposure (top side image) and after 20 days of exposure (bottom side image), consistent with one or more exemplary embodiments of the present disclosure.

FIG. 14 shows sonography images of twin shaped tumor half of which was exposed to positive electrostatic stimulation (+32 V) at start of exposure (top side image 1402) and after 25 days of exposure (bottom side image 1404), consistent with one or more exemplary embodiments of the present disclosure. Observably, the non-exposed part 1406 continued tumor growth while it was suppressed in exposed part 1408. Sonography results greatly presented more than 70% reduction in the size of treated hump 1408 compared to control hump 1406 in 25 days.

Figure 15A:
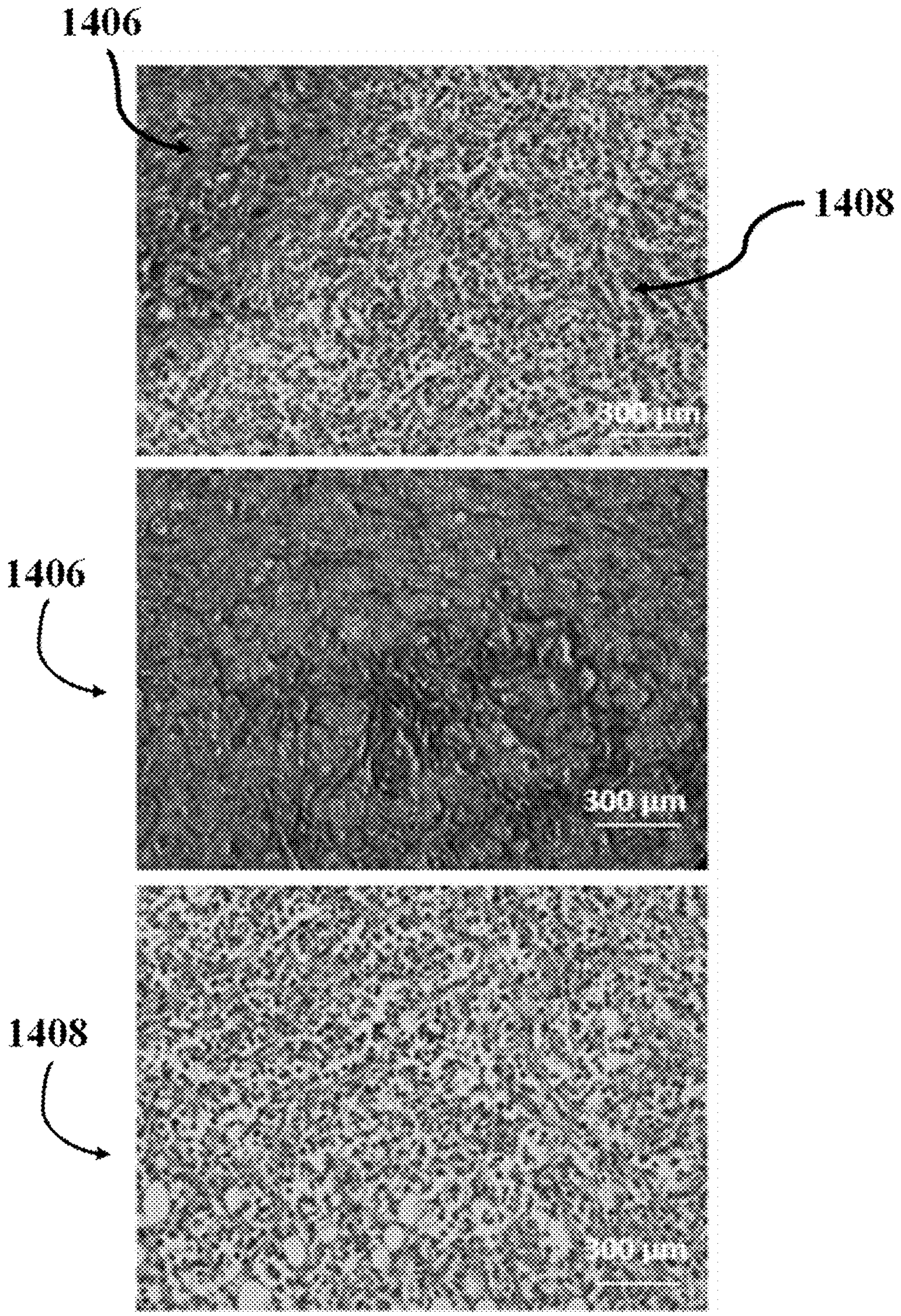
FIG. 15A illustrates H&E images taken from both treated and non-treated regions (top side) of twin tumor, the half non-exposed (middle side), and the half exposed (bottom side), consistent with one or more exemplary embodiments of the present disclosure.

FIG. 15A shows H&E images taken from both treated region 1408 and non-treated region 1406 (top side) of twin tumor, the half non-exposed 1406 (middle side), and the half exposed 1408 (bottom side), consistent with one or more exemplary embodiments of the present disclosure. H&E images taken from the half exposed twin tumor presented the trace of apoptotic cells in exposed region 1408 and non-perturbed cancer cells in non-exposed region 1406.

Figure 15B:
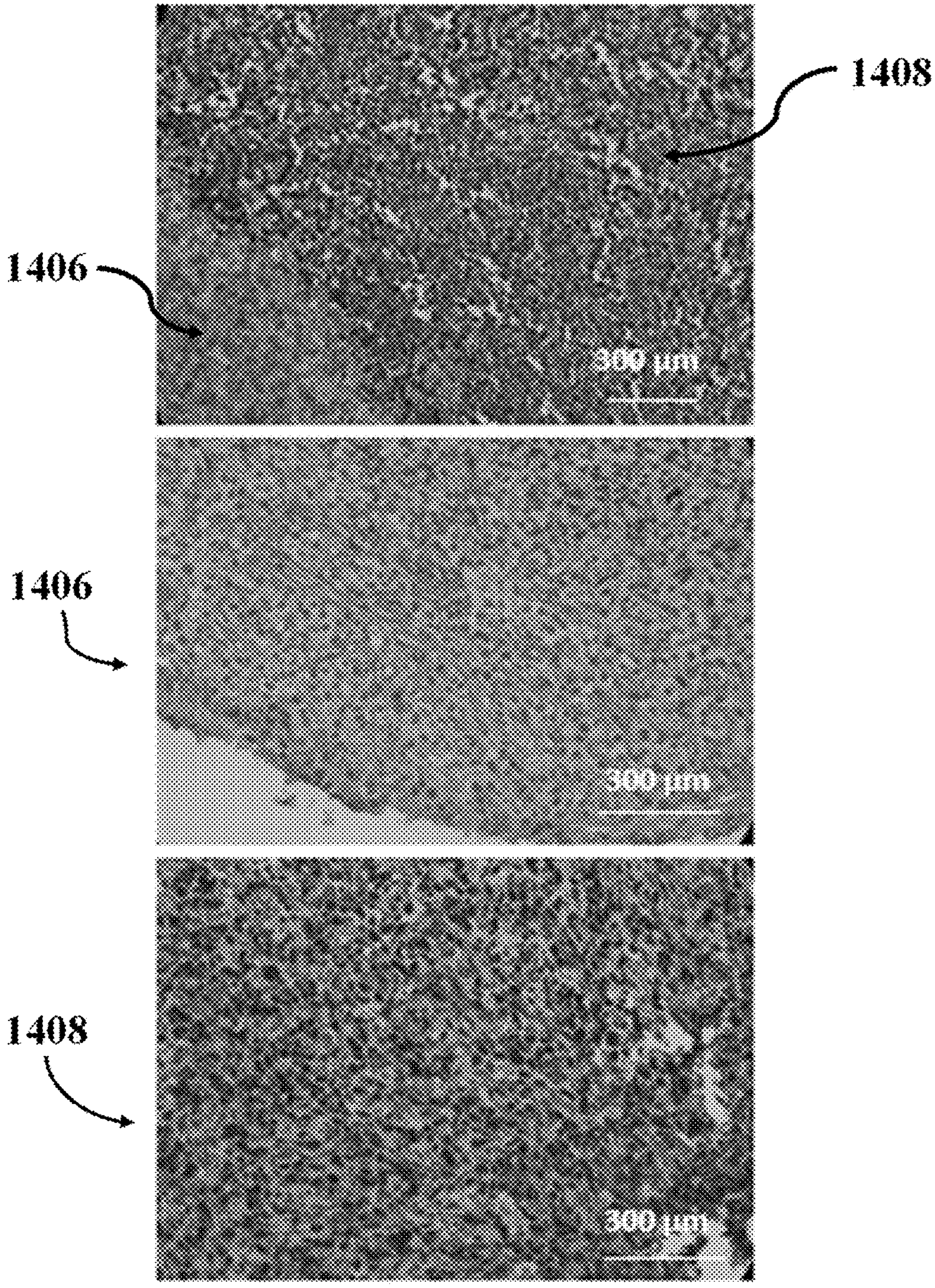
FIG. 15B illustrates P53 based IHC images taken from both treated and non-treated regions (top side) of twin tumor, the half non-exposed (middle side), and the half exposed (bottom side), consistent with one or more exemplary embodiments of the present disclosure.
Figure 15C:
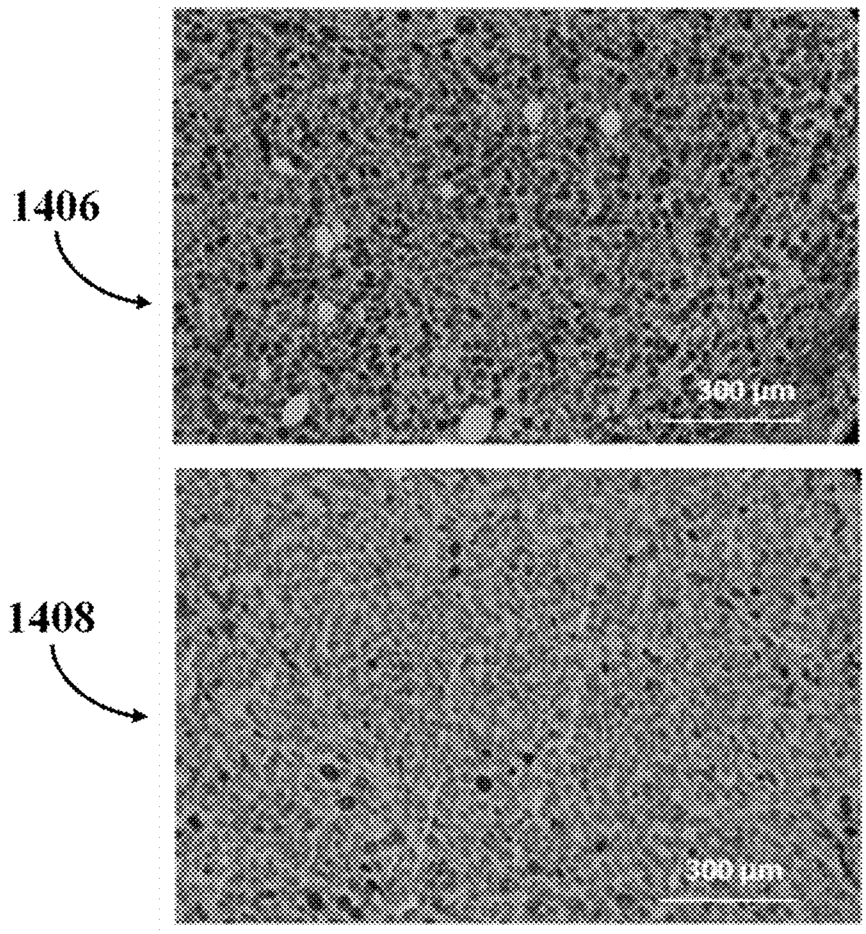
FIG. 15C illustrates Ki67 based IHC images taken from the half non-exposed (top side), and the half exposed (bottom side), consistent with one or more exemplary embodiments of the present disclosure.

FIG. 15B shows P53 based IHC images taken from both treated region 1408 and non-treated region 1406 of twin tumor (top side), the half non-exposed 1406 (middle side), and the half exposed 1408 (bottom side), consistent with one or more exemplary embodiments of the present disclosure. Moreover, FIG. 15C shows Ki67 based IHC images taken from the half non-exposed 1406 (top side), and the half exposed 1408 (bottom side), consistent with one or more exemplary embodiments of the present disclosure. P53 based IHC images indicated the apoptosis in exposed region 1408 and Ki67 based IHC images revealed the presence of proliferative cancer cells' just in non-exposed region 1406. Trace of apoptosis in H&E and IHC images of post exposed hump and tumor heterogenic distribution (with conventional proliferation) in non-exposed hump with a distinguished boundary indicated the selective tumor apoptosis in just electrostatically stimulated region. This rejected any probability that positive electrostatic stimulation may have had non-localized or blood-based effects like electrolysis, since the adjacent non-stimulated tumor part showed no apoptotic or necrotic changes to be attributed to poor blood supply.

Example 5: Complete Destruction of the Tumor

In this example, to evaluate if positive electrostatic stimulation could completely suppress the growth of a metastatic tumor, lower counts of 4T1-derived cancer cells ($0.1\times10^6$ and $0.01\times10^6$) into 20 additional mice were implanted. Tumor formation was investigated and confirmed in 6 of the 20 mice by sonography 5 days after injection. The exposing process was started when the primary size of the tumors reached to 0.4-0.5 $cm^3$. In this step, two strategies were applied to completely degrade the formed tumor: first, increasing the stimulating electrostatic potential to +60 V, and second, fabricating the treating patch by flexible VAMWCNT coated Al/Cu foil shielded by PDMS to form complete shielding of the tumor by the exemplary fabricated flexible patch. To confirm the non-destructive effect of such voltage on normal tissue, the same test was conducted on 3 normal mice.

Figure 16A:
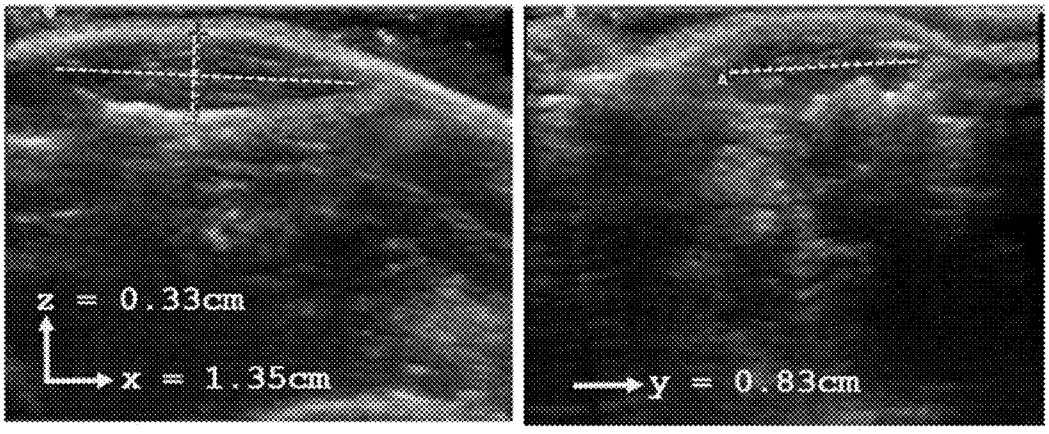
FIG. 16A illustrates sonography images of the formed tumor in X, Z direction (left side) and in Y direction (right side) 3 days after injection, consistent with one or more exemplary embodiments of the present disclosure.
Figure 16B:
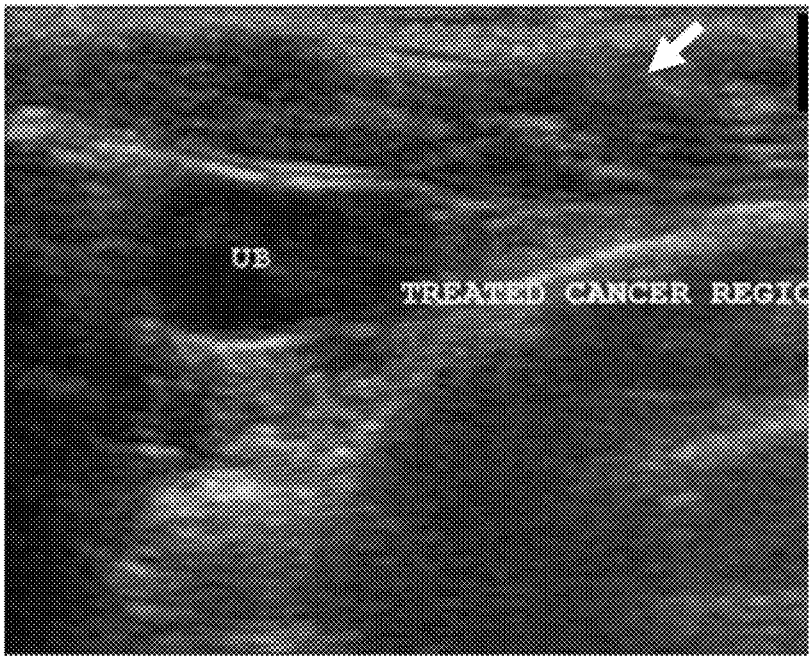
FIG. 16B illustrates sonography image of the completely degraded tumor, consistent with one or more exemplary embodiments of the present disclosure.
Figure 16C:
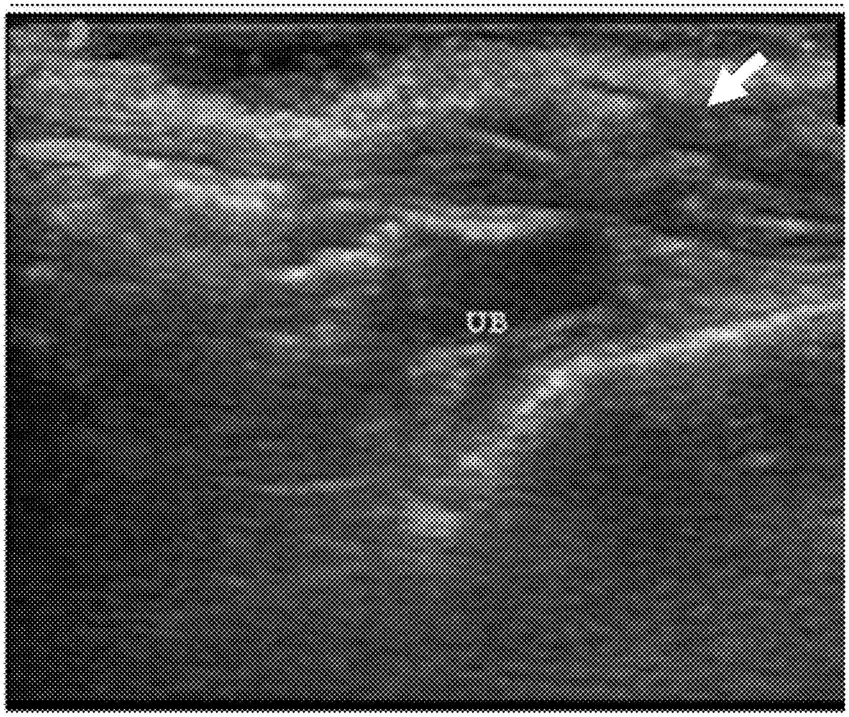
FIG. 16C illustrates sonography image of the cured tumor location 50 days after electrostatic therapy, consistent with one or more exemplary embodiments of the present disclosure.

FIG. 16A shows sonography images of the formed tumor in X, Z direction (left side) and in Y direction (right side) 3 days after injection, consistent with one or more exemplary embodiments of the present disclosure. FIG. 16B shows sonography image of the completely degraded tumor, consistent with one or more exemplary embodiments of the present disclosure. White arrow shows the location of the tumor before treatment. FIG. 16C shows sonography image of the cured tumor location 50 days after electrostatic therapy, consistent with one or more exemplary embodiments of the present disclosure. No recurrence of the tumor could be observed.

Figure 17:
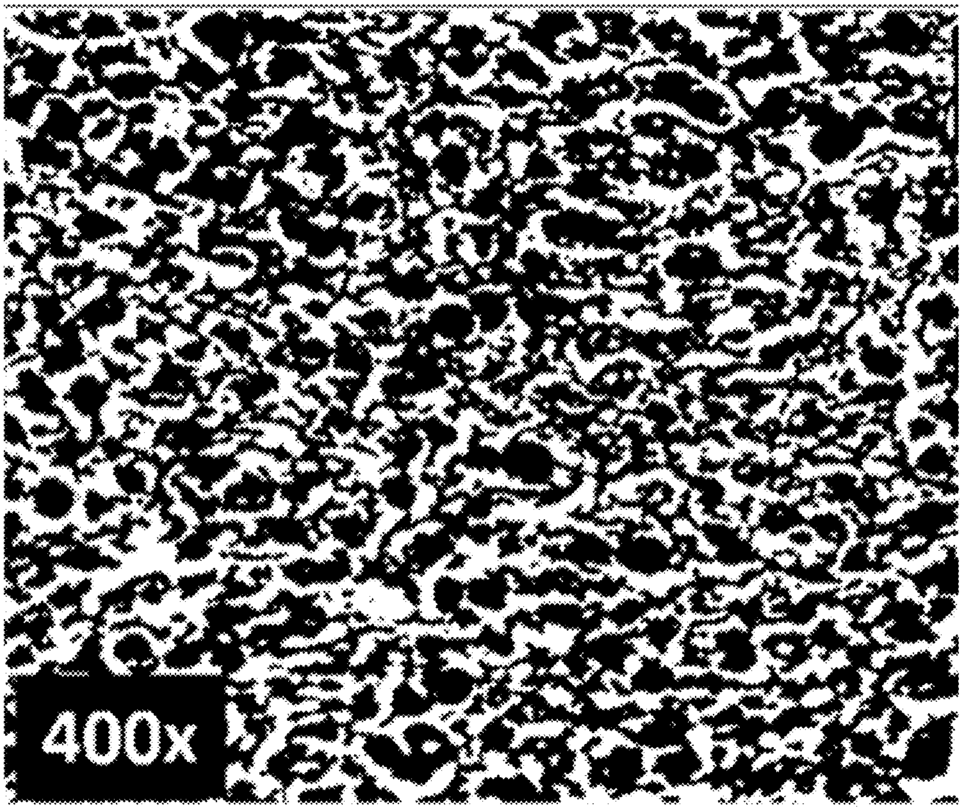
FIG. 17 illustrates H&E image taken from the biopsied sample of the individual mice treated under similar condition in 3rd day of treatment, consistent with one or more exemplary embodiments of the present disclosure.

Moreover, H&E image taken from a biopsied sample of an individual mice treated under same procedure in $3^{rd}$ day of treatment showed that the nest of the tumor contain apoptotic cells and no proliferative tumor cells could be found. FIG. 17 shows H&E image taken from the biopsied sample of the individual mice treated under similar condition in $3^{rd}$ day of treatment, consistent with one or more exemplary embodiments of the present disclosure. Apoptotic cells with hyperchromic nucleus are observable and no viable cancer cells with conventional morphology could be found.

Sonography images presented in FIGS. 16A-16C followed by histopathological evaluation presented in FIG. 17, show the complete degradation of a tumor with primary size of $1.3\times0.8\times0.3$ $cm^3$ in 5 days under continuous stimulation with neither side effect to non-cancerous tissue nor pathological induction on stimulated normal mice. White arrow in the sonography image of figure FIG. 16B, presented the location of the completely degraded tumor. Repeating the sonography 50 days after treatment, revealed no recurrence of the tumor (FIG. 16C).

Figure 18:
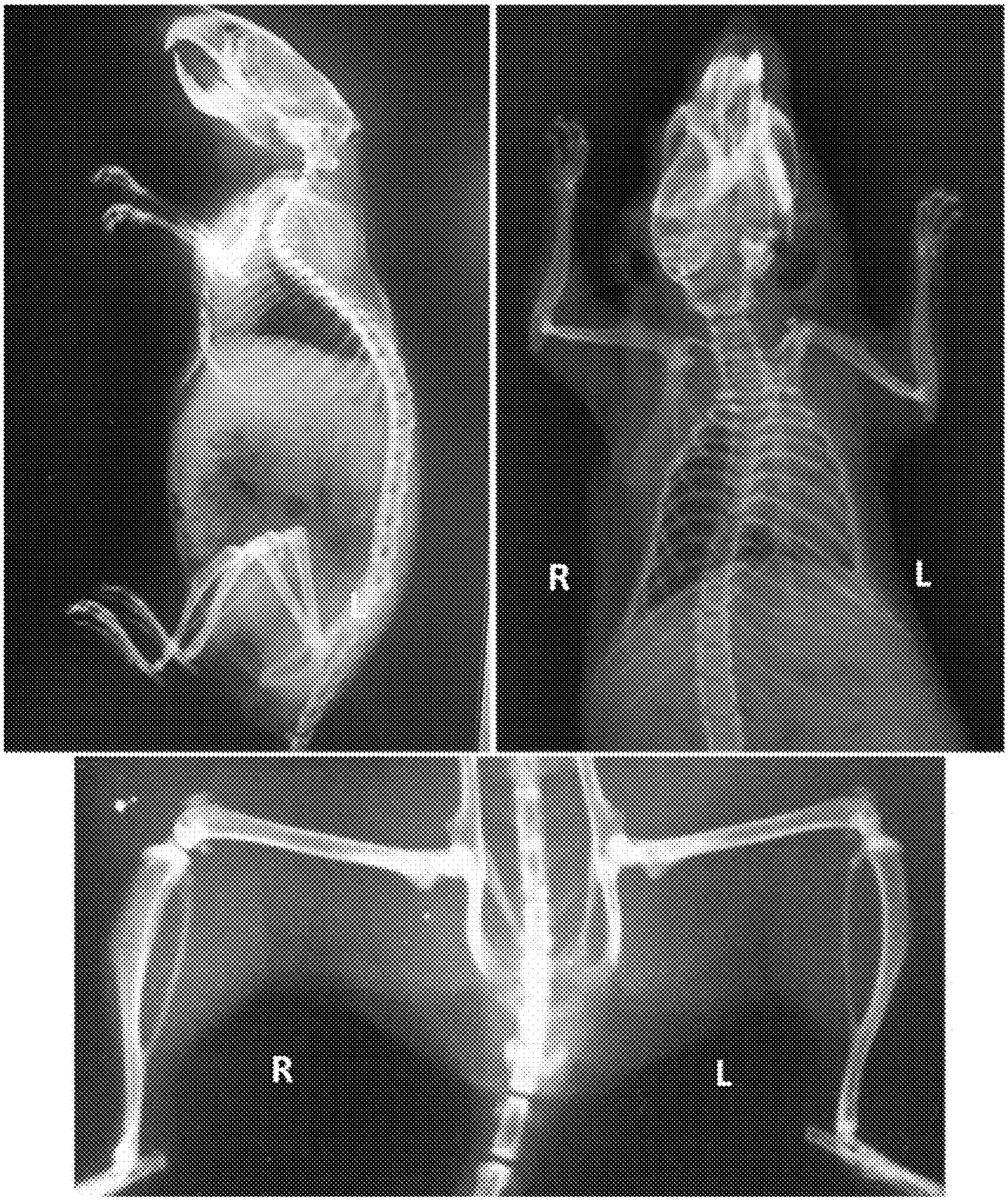
FIG. 18 illustrates X-Ray radiography image from the lung and bone structures of the mice treated by electrostatic therapy with complete destruction of the tumor 100 days after electrostatic treatment, consistent with one or more exemplary embodiments of the present disclosure.

In addition, x-ray radiography images taken 100 days after the tumor destruction showed no abnormal signs in the bones and lung of the treated mice. FIG. 18 shows X-Ray radiography images from the lung and bone structures of the mice treated by electrostatic therapy with complete destruction of the tumor 100 days after electrostatic treatment, consistent with one or more exemplary embodiments of the present disclosure. No signs of abnormality or any irregular mass could be observed both lung and bone structures. The bone of the left leg (nearest bone to the primary tumor) presented a completely normal shape and density. This excludes any probable metastasis of the destructed tumor to the bone tissue as one of the most prevalent metastasis targets in 4T1 derived breast cancer.

Example 6: Tumor Suppression Utilizing an Electrostatic Positive-Charged Wire

In this example, exemplary system 1900 was utilized for tumor suppression in rats tumorized with 4T1 tumor in hip tissue through applying exemplary method 2000. Tumor localization guide wires were utilized as examples of wire 1902. Utilized tumor localization guide wires were analyzed for determining their characterizations, and it was obtained that the utilized tumor localization guide wires had an electrical conductivity of about $8.9\times10^4$ $ohm^{-1}$ $cm^{-1}$. The utilized tumor localization guide wires were made of metallic/electrically conductive alloys including titanium-nickel-tantalum (Ti—Ni—Ta). Rats tumorized with 4T1 tumor were divided in four groups, including control (non-treated), neutral-wire (neutral tumor localization guide wire was implanted in tumoral tissue), negative-wire (negatively-charged tumor localization guide wire was implanted in tumoral tissue), and positive-wire (positively-charged tumor localization guide wire was implanted in tumoral tissue). Electrostatic field was applied to the negatively-charged tumor localization guide wires with intensity of about −1 kV, and an intensity of electrostatic field applied to the positively-charged tumor localization guide wires was about +1 kV. Electrostatic field was applied to the rats over a time period of about 6 hours.

Figure 23:
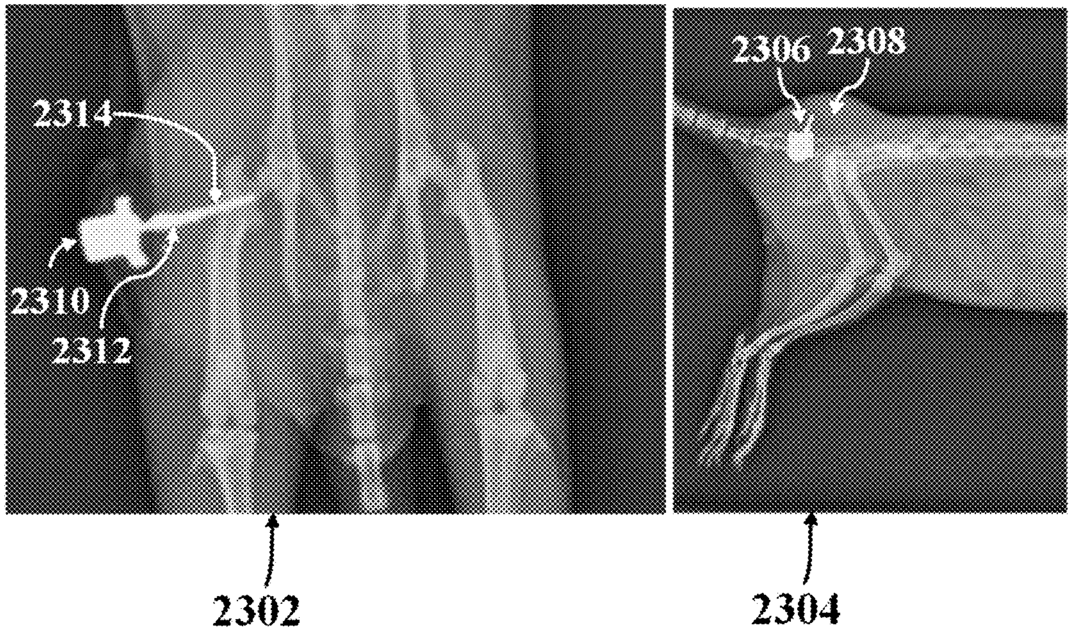
FIG. 23 shows two exemplary X-ray images (top-view) and (side-view) of an exemplary tested rat with an exemplary implanted wire in its 4T1 tumor site, consistent with one or more exemplary embodiments of the present disclosure.

FIG. 23 shows two exemplary X-ray images 2302 (top-view) and 2304 (side-view) of an exemplary tested rat herein with implanted wire 2306 (similar to wire 1902) in its 4T1 tumor site 2308, consistent with one or more exemplary embodiments of the present disclosure. Exemplary wire 2306 included internal connector 2310, electrically isolated part 2312, and needle-shaped non-isolated part 2314. Electrically isolated part 2312 was isolated with a layer of PDMS by immersing wire 2306 in PDMS material. Non-isolated part 2314 (similar to active part 1904) was not electrically isolated because it was located within the 4T1 tumor site, and isolated part 2312 was configured to accumulate electrostatic charges thereon. Internal connector 2310 was connected to an electrostatic charge generator similar to electrostatic charge generator 1908.

Figure 24:
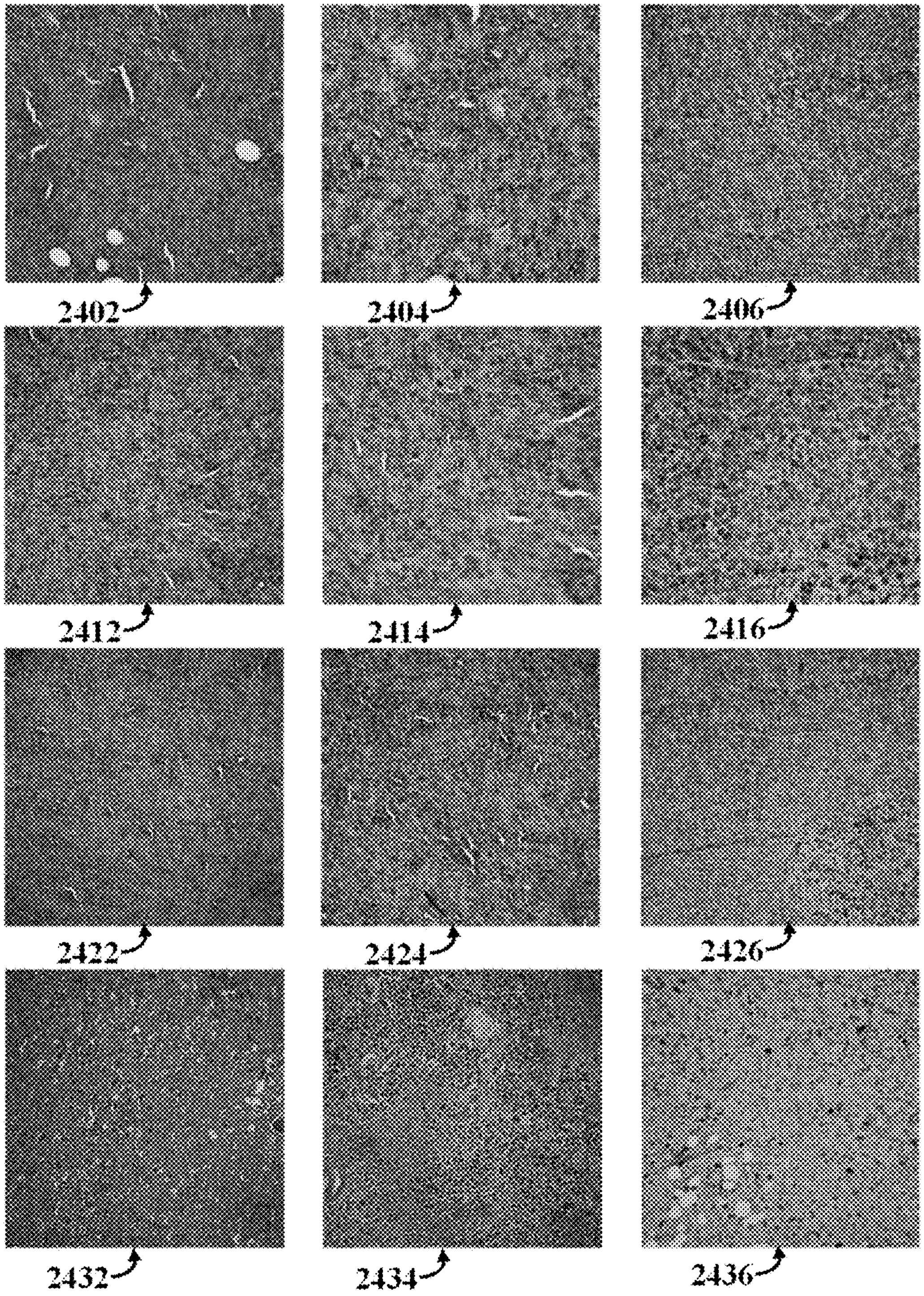
FIG. 24 shows H&E images with two magnification levels and KI67 proliferative immunomarker assay results for control, neutral-wire, negative-wire, and positive-wire, consistent with one or more exemplary embodiments of the present disclosure.

Hematoxylin & cosin (H&E) and immunohistochemistry (IHC) assays were conducted on exposed and non-exposed rats to electrostatic stimulation after about 5 days. To confirm suppressed proliferation and apoptotic induction in treated tumor cells, assay KI67 as proliferative immunomarker was done using IHC. FIG. 24 shows H&E images with two magnification levels for control (images 2402 and 2404), neutral-wire (images 2412 and 2414), negative-wire (images 2422 and 2424), and positive-wire (images 2432 and 2434), consistent with one or more exemplary embodiments of the present disclosure. FIG. 24 also shows KI67 proliferative immunomarker assay results for control (image 2406), neutral-wire (image 2416), negative-wire (image 2426), and positive-wire (image 2436), and consistent with one or more exemplary embodiments of the present disclosure. A presence of more than about 90% of high malignant cancer cells may be observed for control and neutral-wire wires. Moreover, high malignant cancer cells were remained non-treated (more than about 80%-90%) in negative-wire group. Whereas, in group positive-wire, treated site is clearly observable where only nuclei dusts were remained due to necrosis of cancer cells after positively electrostatic stimulation of cancer cells induced by positive charges accumulated on exemplary implanted wire 1902 in 4T1 tumor site.

Example 7: Electrostatically Deactivating Suspended Circulating Cancer Cells

Figure 28:
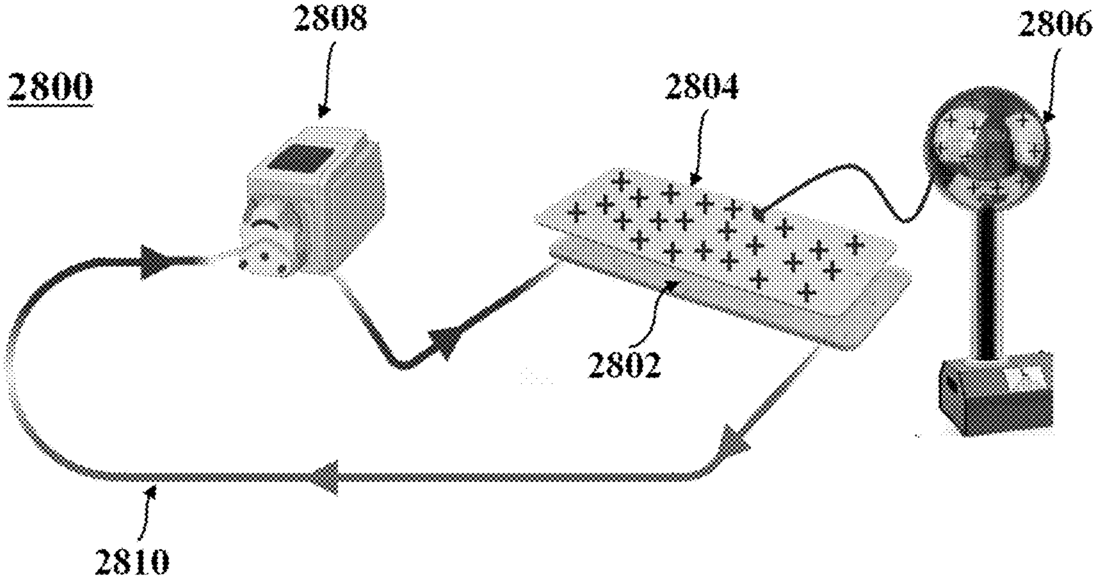
FIG. 28 shows a schematic view of an exemplary system for deactivating CTCs, consistent with one or more exemplary embodiments of the present disclosure.

In this example, a system similar to exemplary system 2510 was utilized for deactivating CTCs by applying a method similar to exemplary method 2600. FIG. 28 shows a schematic view of exemplary system 2800 utilized in this example for deactivating CTCs, consistent with one or more exemplary embodiments of the present disclosure. System 2800 may is a closed-loop implementation of exemplary system 2510, and was utilized for electrostatic stimulation of suspended cytological samples including CTCs and blood. The cells were passed through fluidic channel 2802 with a spiral shape and were exposed to positive electrostatic charges by an embedded charged plate 2804 on top of channel 2802. Plate 2804 included an aluminum foil tape covered on an insulator. In order to mimic physiologically related flows and shear stresses in superficial veins like the cephalic vein of the arm, tube line 2810 with an inner diameter of about 2.8 mm and a length of about 50 cm was chosen for and flow rate was set to be about 2 cm/s (7.4 ml/min). Depending on the test, CTCs and WBCs were mixed or individually circulated for about 4 hours utilizing peristaltic pump 2808 through channel 2802.

To evaluate selective destructive effect of pure positive electrostatic charge stimulation (PPECS) on CTCs, suspended MDA-MB-231 cell line (metastatic grade of human breast cancer cell line) in DMEM carrier solution as a model of highly metastatic breast cancer was selected for the tests. Three major assays including proliferation of treated cells, invasion of treated cells to endothelial layer, and relative MMP expression (as an invasion marker) in treated cells with PPECS were compared with non-treated cells. In addition, the effect of the PPECS on the viability of the circulating MDA-MB-231 cells was analyzed using MTT analysis and apoptosis assay.

To minimize nonspecific adhesion of cells to the tubing, a 1% BSA/PBS was circulated for about 10 min and all the tubing walls were blocked. For maintaining pH value of cell culture media in extended period of the tests, cell culture medium contained about 20 mM of 4-(2-hydroxyethyl)-1-piperazineethanesulfonic acid (HEPES) buffer solution. Buffer containing cells was circulated at a flow rate of about 7.4 ml/min (2 cm/s) for 4 hours in standard cell living environment (temperature of 37° C. and 5% $CO_2$). After treatment, the cells were collected and resuspended in ultralow-attachment tissue culture plates and the process was repeated for two more consecutive days.

In this regard, MDA-MB-231 cells were divided into three individual groups of CTRL, −PPECS, and +PPECS. In the case of the control group (CTRL), no circulation was performed and just analysis was done for the cells cultured in the flask. But the other two groups of −PPECS and +PPECS were suspended in DMEM solution ($10^7$ cells/10 ml) and circulated by peristaltic pump 2808 (flow rate about 7.4 ml/min) for 3 subsequent days and 4 hours per day. The first group of cells was just circulated without any electrostatic stimulation (−PPECS) and the second group was exposed to positive electrostatic charge (+PPECS) during the circulation. In +PPECS tests, four different intensities of electrostatic field including about 0.1 kV, 1 kV, 5 kV, and 10 kV were induced by exemplary Van de Graaff generator 2806 that resulted in accumulating positive electrostatic charges on plate 2804; and then, channel 2802 containing circulating cells was in direct contact with the PPECS. For-PPECS cohort, the same procedure was done while Van de Graaff generator 2806 was disconnected. After termination of circulation in each day, suspended cells were cultured on microwells and resuspended in the next day for the next round of circulation up to three days. After 3 steps of circulation, the effect of PPECS on proliferative properties of suspended MDA-MB-231 cells was evaluated.

Figure 29A:
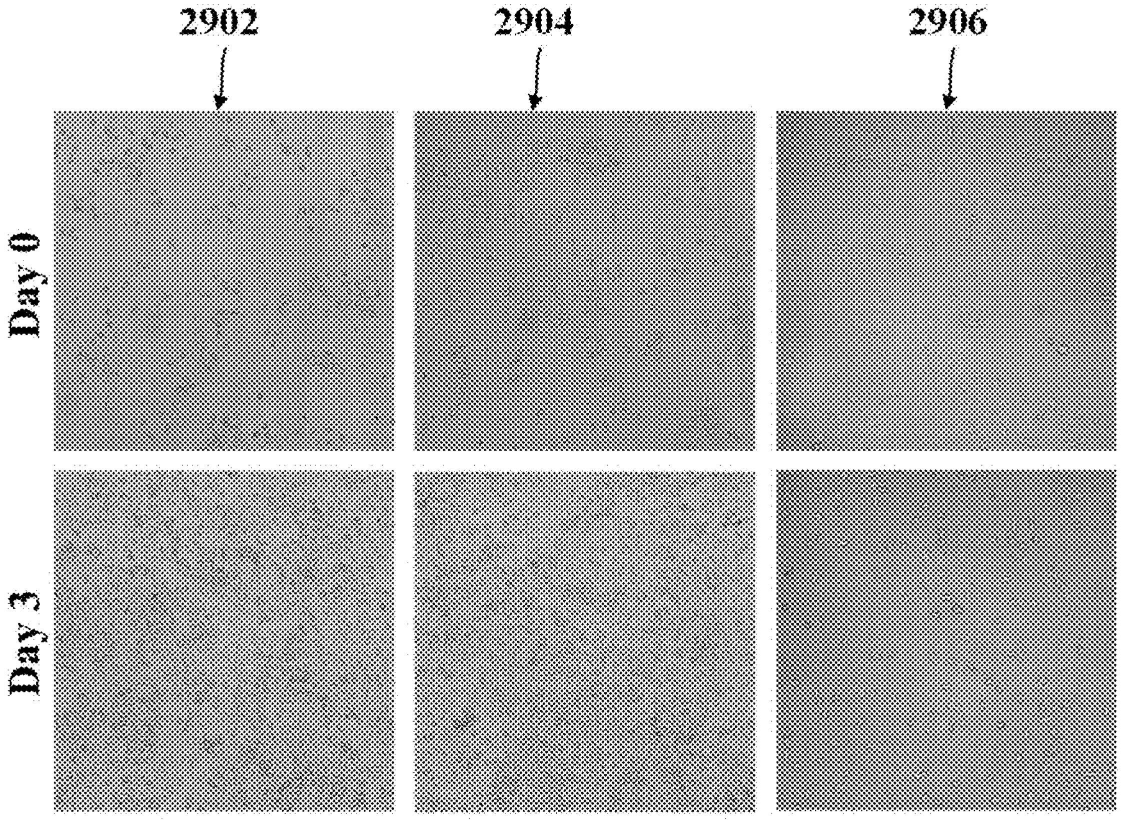
FIG. 29A shows proliferative analysis of control group cells without circulation, −pure positive electrostatic charge stimulated (−PPECS) cells, and +PPECS cells treated by +10 kV electrostatic field by optical microscopy, consistent with one or more exemplary embodiments of the present disclosure.
Figure 29B:
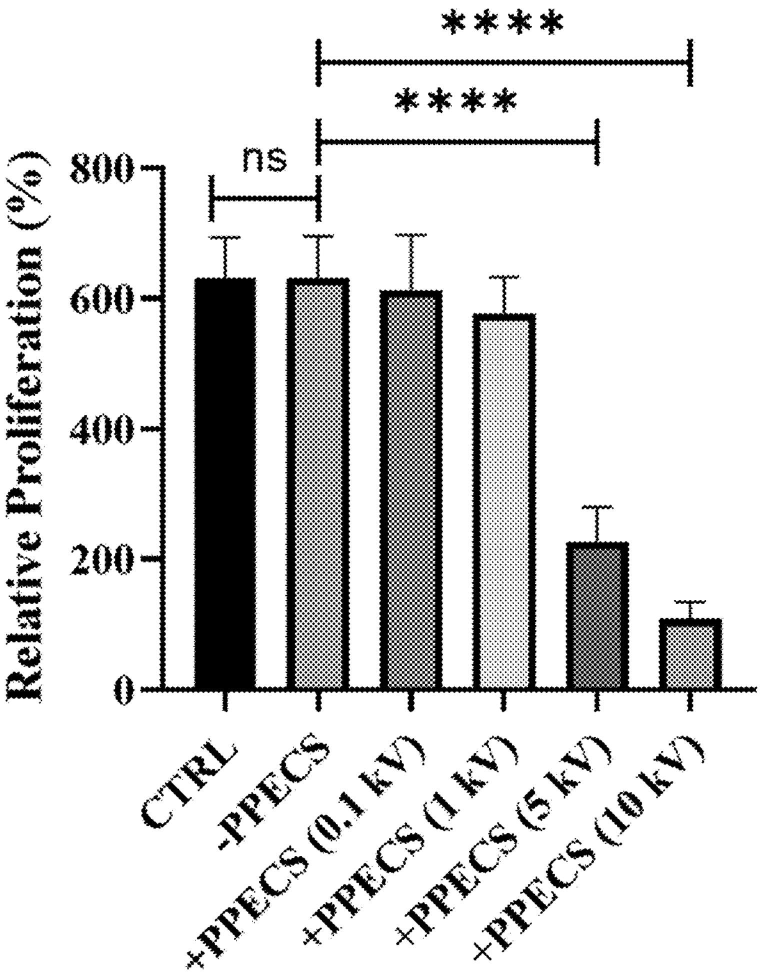
FIG. 29B shows relative proliferative analysis of −/+PPECS cells and control group corresponding to optical microscopy analysis, consistent with one or more exemplary embodiments of the present disclosure.

Control group, treated (+PPECS), and non-treated (−PPECS) circulating cells were individually cultured and investigated by proliferation assay. FIG. 29A shows proliferative analysis of control group cells 2902 without circulation, −PPECS cells 2904, and +PPECS cells 2906 treated by +10 kV electrostatic field by optical microscopy, consistent with one or more exemplary embodiments of the present disclosure. FIG. 29B shows relative proliferative analysis of −/+PPECS cells and control group corresponding to optical microscopy analysis of FIG. 29A, consistent with one or more exemplary embodiments of the present disclosure. As may be seen, PPECS treatment drastically reduced the ability of cellular proliferation (FIG. 29B) and as the strength of the stimulation was increased, the relative proliferation was more suppressed. This phenomenon was accompanied by a reduction of the cell's viability after being exposed to higher intensities of the electric field.

Figure 30:
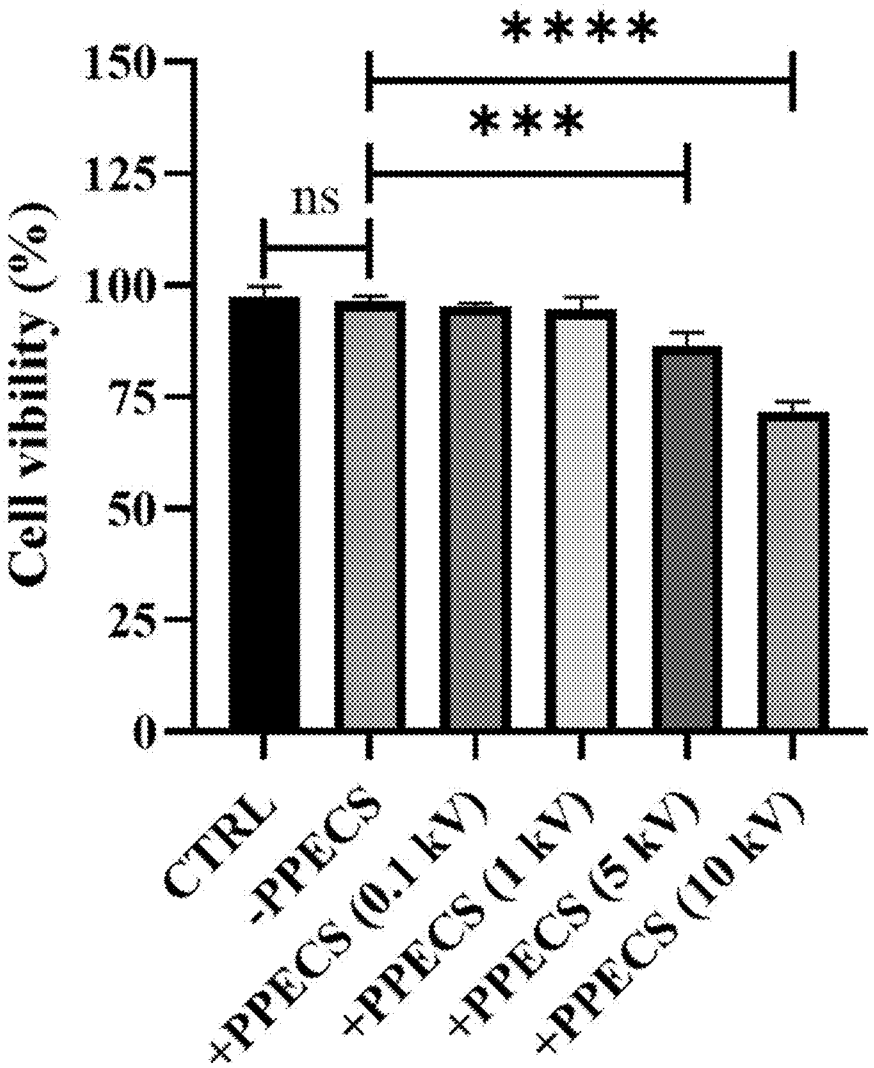
FIG. 30 shows MTT analysis assay for the three groups of Control, −PPECS, and +PPECS with increasing potential, consistent with one or more exemplary embodiments of the present disclosure.
Figure 31:
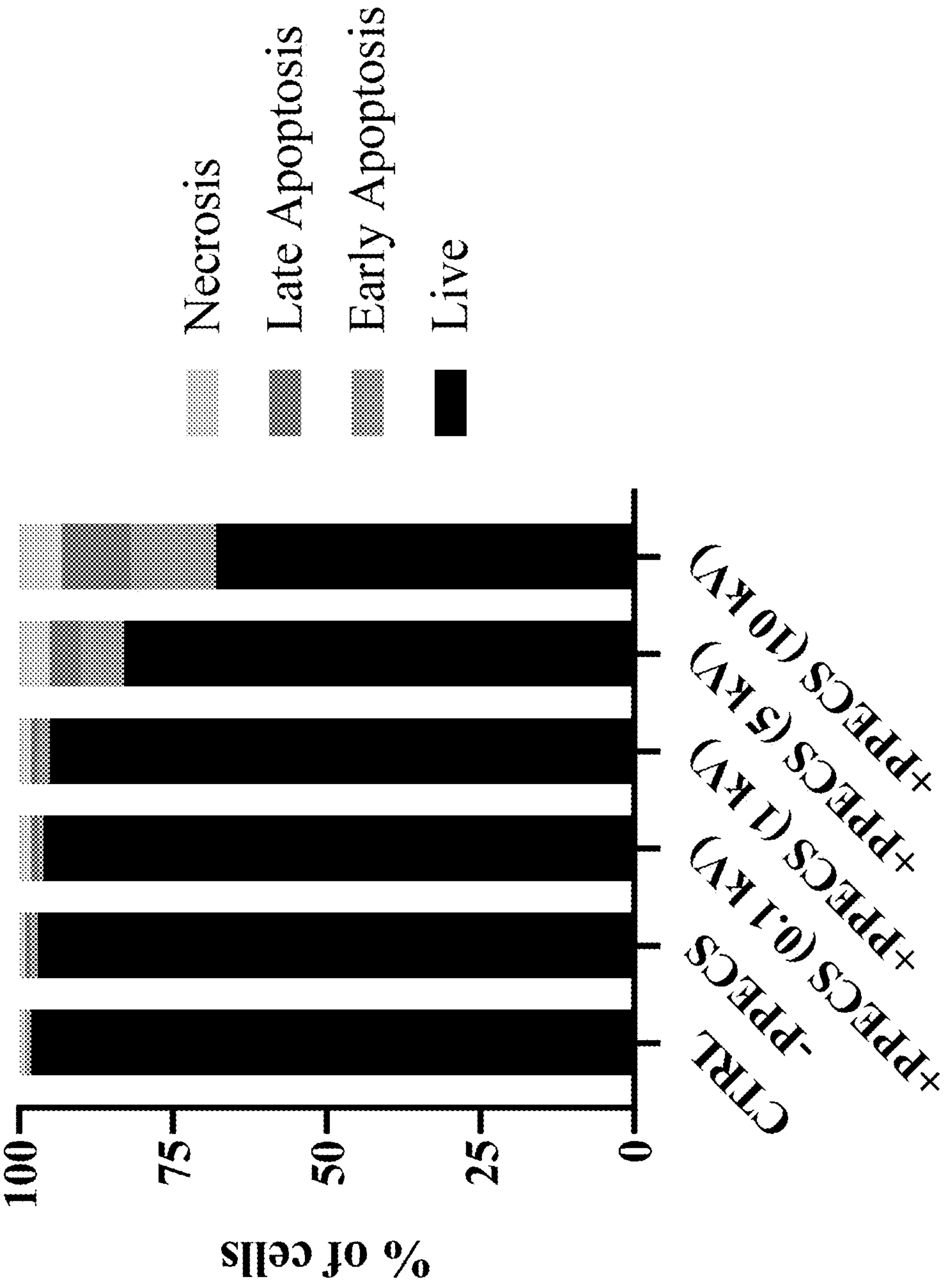
FIG. 31 shows Annexin V/PI apoptosis assay for the three groups of Control, −PPECS, and +PPECS with increasing potential, consistent with one or more exemplary embodiments of the present disclosure.

FIG. 30 shows MTT analysis assay for the three groups of Control, −PPECS, and +PPECS with increasing potential, consistent with one or more exemplary embodiments of the present disclosure. FIG. 31 shows Annexin V/PI apoptosis assay for the three groups of Control, −PPECS, and +PPECS with increasing potential, consistent with one or more exemplary embodiments of the present disclosure. Both MTT and Annexin V/PI (FIG. 2-D) assays showed that circulation had no impact on the viability of the cells and mortality of the circulated cells was just proportional to the potential of the exposing charge source.

Figure 32:
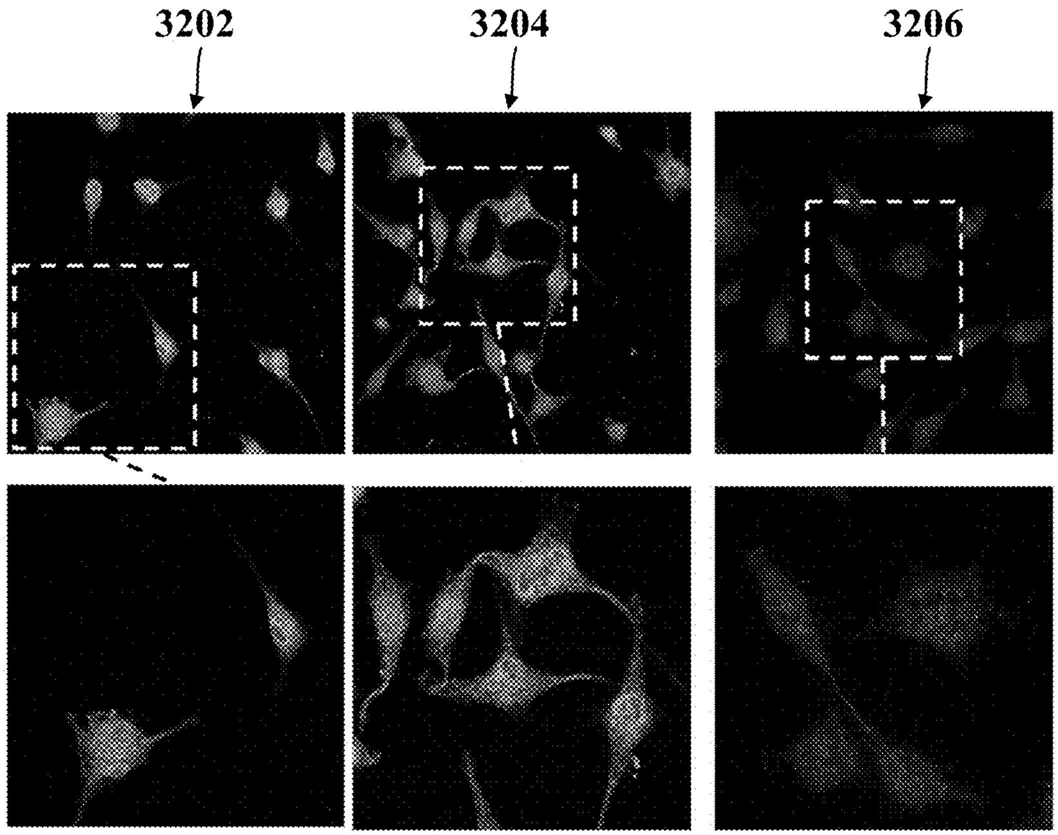
FIG. 32 shows MMP-2 immunofluorescent confocal imaging of the control cells, non-treated cells (−PPECS), and treated MDA-MB-231 (+PPECS) cells by +10 kV electrostatic field, consistent with one or more exemplary embodiments of the present disclosure.
Figure 33:
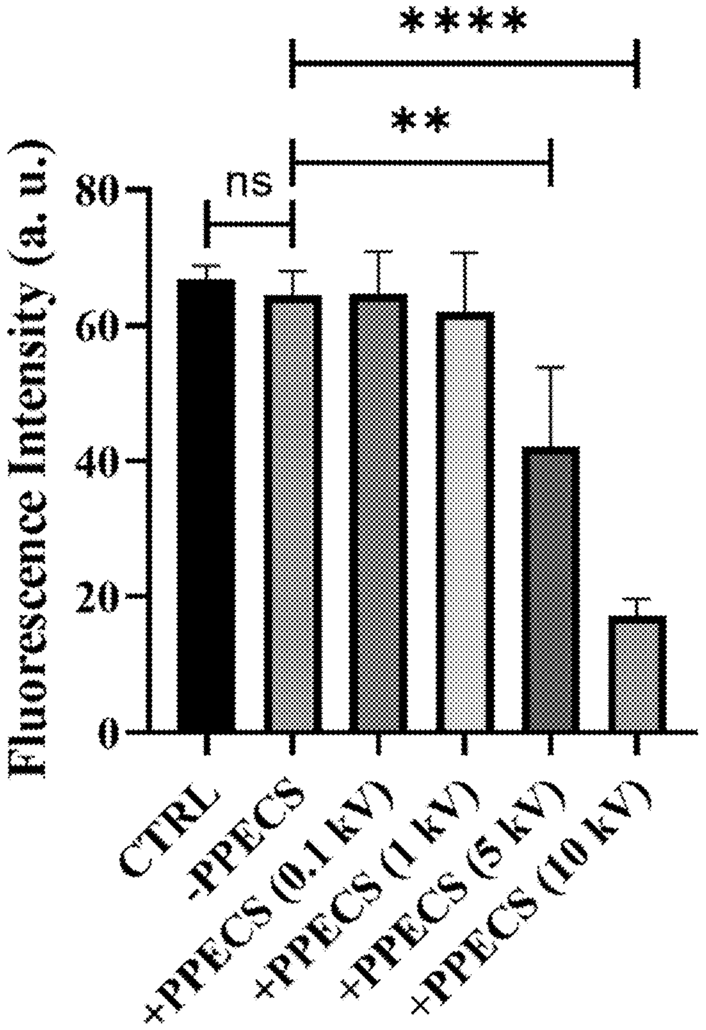
FIG. 33 shows fluorescent intensity analysis relative to MMP-2 immunofluorescent confocal imaging of the control cells, non-treated cells (−PPECS), and treated MDA-MB-231 (+PPECS) cells by +10 kV electrostatic field, consistent with one or more exemplary embodiments of the present disclosure.

Moreover, the effect of PPECS treatment on invasive abilities of circulating cancer cells was investigated. In this regard, all of the three cohorts (including +PPECS, −PPECS, and CTRL) were re-cultured on individual plates and undergone matrix metalloprotease-2 (MMP-2) immunofluorescent assay. FIG. 32 shows MMP-2 immunofluorescent confocal imaging of the control cells 3202, non-treated cells (−PPECS) 3204, and treated MDA-MB-231 (+PPECS) cells 3206 by +10 kV electrostatic field, consistent with one or more exemplary embodiments of the present disclosure. FIG. 33 shows fluorescent intensity analysis relative to MMP-2 immunofluorescent confocal imaging of the control cells, non-treated cells (−PPECS), and treated MDA-MB-231 (+PPECS) cells by +10 kV electrostatic field, consistent with one or more exemplary embodiments of the present disclosure. Expression of MMP-2 on filopodial protrusions of cancer cells may be a well-known indication about the invasive ability of metastatic cancer cells. Analysis of the immunofluorescent images showed meaningful reduction (about 73%) in MMP-2 expression of +PPECS cells (10 kV) with respect to −PPECS group (FIG. 33). Similarly, the results revealed that the sole circulation has no effect on the expression of MMP-2 protein and also, the most down-regulation of protein expression was attributed to the cells had been exposed to the highest intensity of the electrostatic field (FIG. 33).

Figure 34:
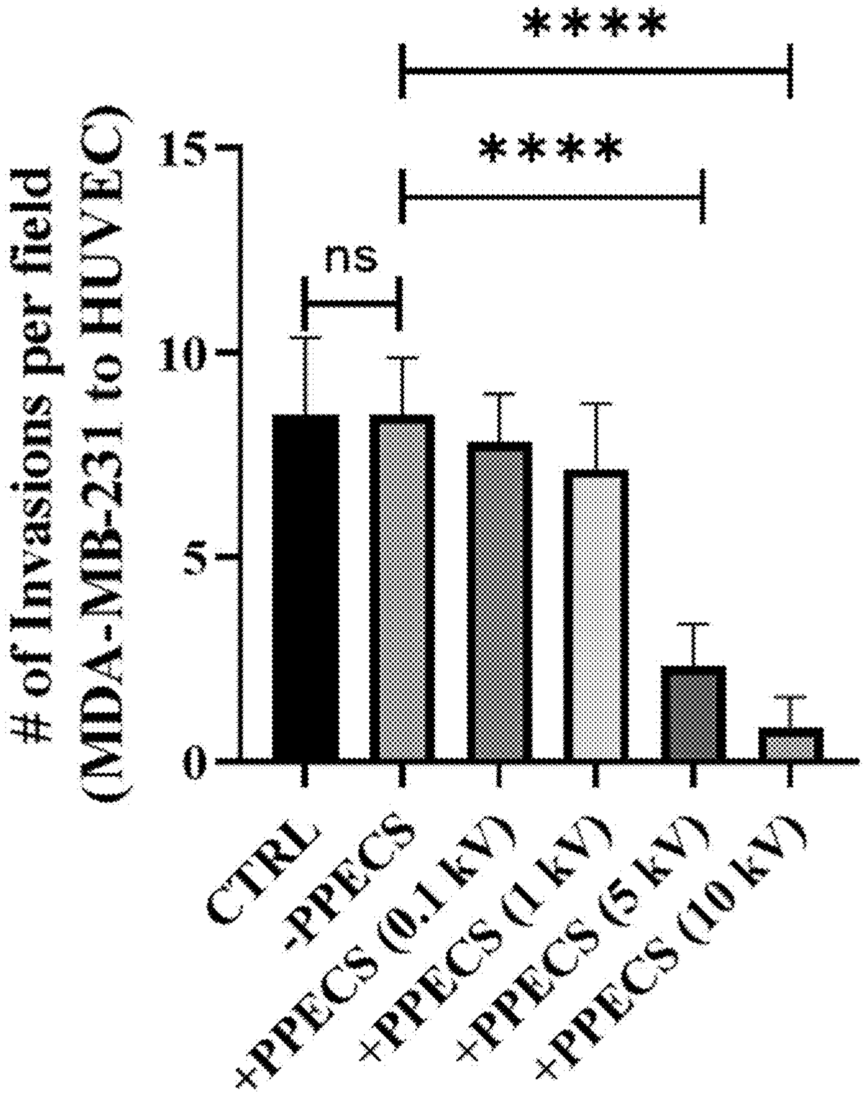
FIG. 34 shows number of attacks by three investigated groups of MDA-MB-231 cells to Human umbilical vein endothelial cells (HUVECs), consistent with one or more exemplary embodiments of the present disclosure.

One of the main prerequisites of metastasis may be the extravasation in which an invasive cancer cell invades and crosses the endothelial barrier. Here, the extravasation process was mimicked by individual interaction of the Control cells (CTRL) as well as both −/+PPECS circulated MDA-MB-231 cells with Human umbilical vein endothelial cells (HUVEC) cell line as a model of an endothelium to evaluate the impact of the PPECS treatment on invasive functions of CTCs. MDA-MB-231 cancer cell and endothelial cells (HUVEC) interactions were time-lapse monitored. Control, as well as-PPECS (non-treated) circulated MDA-MB-231 cells severely invaded to the endothelial barrier induced membrane blebbing to HUVECs as a sign of the invasion while +PPECS cells showed observably weak invasive behavior and very rare retraction of the HUVECs was observed after their interaction by +PPECS CTCs. FIG. 34 shows number of attacks by three investigated groups of MDA-MB-231 cells to the HUVECs, consistent with one or more exemplary embodiments of the present disclosure. The numbers of attacks to HUVECs were assumed as invasive ability of cancer cells which showed an about 88% reduction in +PPECS cells.

Example 8: Effect of PPECS on Blood Cells

In this example, to investigate if PPECS treatment might induce any side effects on circulating blood cells, a small volume of peripheral blood of human donators (repeated 5 times) was removed from the body and circulated under the PPECS stimulation, similar to that had been done for suspended breast cancer cell lines as CTC models.

The crucial biological and functional parameters of the blood for evaluating any abnormality in blood cells were assayed on both cohorts of the −/+PPECS. FIG. 35 shows complete blood count analysis of the blood for −/+PPECS groups, consistent with one or more exemplary embodiments of the present disclosure. No notable changes in abundance of the blood components including white and red blood cells as well as platelets between PPECS treated and non-treated circulated blood was observed.

Figure 36:
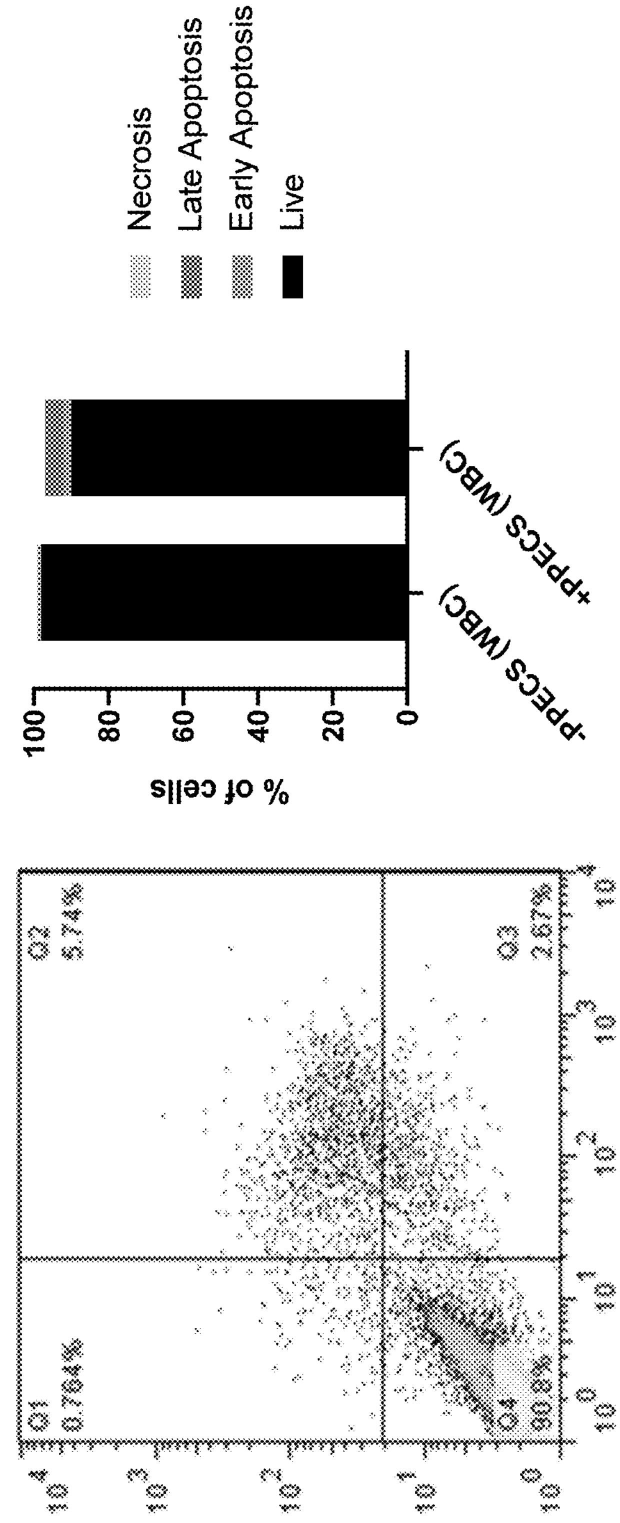
FIG. 36 shows Live/Dead analysis of white blood cells for two groups of treated and non-treated cells by Annexin V/PI method, consistent with one or more exemplary embodiments of the present disclosure.
Figure 37:
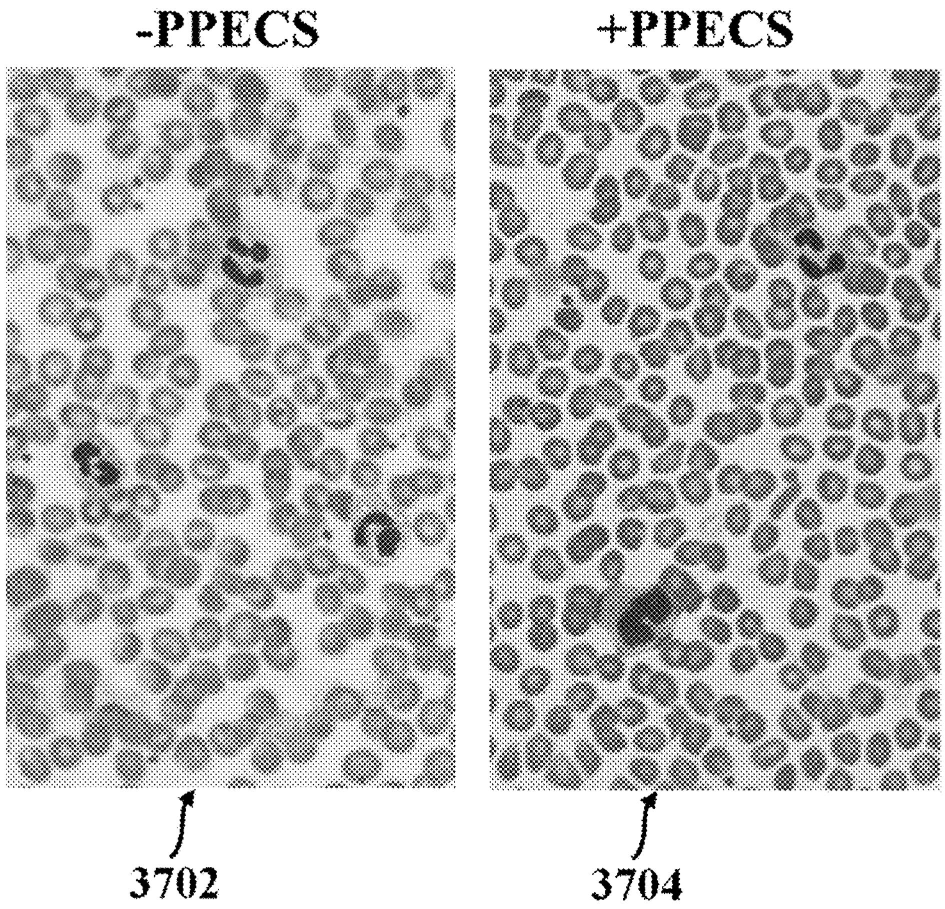
FIG. 37 shows Papanicolaou staining of blood cells for morphological analysis for two groups −PPECS and +PPECS, consistent with one or more exemplary embodiments of the present disclosure.

To evaluate if the PPECS treatment affects the viability of the blood elements, live/dead assay using annexin V/PI flow cytometry was carried out on RBCs and WBCs. FIG. 36 shows Live/Dead analysis of white blood cells for two groups of treated and non-treated cells by Annexin V/PI method, consistent with one or more exemplary embodiments of the present disclosure. Additionally, FIG. 37 shows Papanicolaou staining of blood cells for morphological analysis for two groups −PPECS (image 3702) and +PPECS (image 3704), consistent with one or more exemplary embodiments of the present disclosure. As shown in FIGS. 36 and 37, whole population of the WBCs after circulation without PPECS treatment were almost viable. Moreover, more than about 90% of the +PPECS treated group remained alive. Moreover, cytopathological staining of the blood components may confirm that no morphological deformation was induced to the WBCs and RBCs by the electrostatic stimulation system (FIG. 37).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for in-vivo deactivating circulating cancer cells (CTCs), comprising:
deactivating CTCs by applying a positive electrostatic field to bloodstream of a cancer patient, comprising:
accumulating positive electrostatic charges on an electrically conductive element by applying a positive electrostatic voltage in a range of 50 V to 50 kV to the electrically conductive element utilizing an electrostatic charge generator; and
exposing the bloodstream to the accumulated positive electrostatic charges by placing the electrically conductive element with the accumulated positive electrostatic charges thereon at a distance of less than 10 cm from a portion of the bloodstream, exposing the bloodstream to the accumulated positive electrostatic charges comprising exposing the bloodstream daily for a range of 1 hour to 5 hours for at least three days to the accumulated positive electrostatic charges,
wherein deactivating CTCs comprises at least one of reducing viability of CTCs and destroying CTCs.

2. A method for in-vivo deactivating circulating cancer cells (CTCs), comprising:
deactivating CTCs by applying a positive electrostatic field to bloodstream of a cancer patient,
wherein deactivating CTCs comprises at least one of reducing viability of CTCs and destroying CTCs.

3. The method of claim 2, wherein applying the positive electrostatic field to the bloodstream of the cancer patient comprises:
accumulating positive electrostatic charges on an electrically conductive element by applying a positive electrostatic voltage in a range of 50 V to 50 kV to the electrically conductive element utilizing an electrostatic charge generator; and
exposing the bloodstream to the accumulated positive electrostatic charges by placing the electrically conductive element with the accumulated positive electrostatic charges thereon at a distance of less than 10 cm from a portion of the bloodstream.

4. The method of claim 3, wherein deactivating CTCs by applying the positive electrostatic field to the bloodstream of the cancer patient is done daily for a range of 1 hour to 5 hours for at least three days.

5. The method of claim 3, wherein deactivating CTCs by applying the positive electrostatic field to the bloodstream of the cancer patient comprises:
circulating the portion of the bloodstream of the cancer patient's body inside a fluidic channel, comprising:
extracting the portion of the bloodstream of the cancer patient's body into the fluidic channel; and
re-injecting the portion of the bloodstream from the fluidic channel to the cancer patient's body,
wherein extracting the portion of the bloodstream and re-injecting the portion of the bloodstream are done continuously in a cycle;
placing the electrically conductive element on the fluidic channel containing the circulating portion of the bloodstream;
accumulating positive electrostatic charges on the electrically conductive element by applying the positive electrostatic voltage to the electrically conductive element utilizing the electrostatic charge generator; and
forming deactivated CTCs in the circulating portion of the bloodstream responsive to electrostatically stimulating of CTCs induced by the accumulated positive electrostatic charges.

6. The method of claim 5, wherein circulating the portion of the bloodstream of the cancer patient's body inside the fluidic channel comprises circulating the portion of the bloodstream of the cancer patient's body inside a spiral u-shaped tube.

7. The method of claim 5, wherein circulating the portion of the bloodstream comprises circulating the portion of the bloodstream at a flow rate in a range of 5 ml/min to 500 ml/min.

8. The method of claim 5, wherein circulating the portion of the bloodstream comprises:
extracting the portion of the bloodstream from the cancer patient's body utilizing a first peristaltic pump;
passing the extracted portion of the bloodstream through the fluidic channel utilizing the first peristaltic pump; and
transmitting the portion of the bloodstream from the fluidic channel to the cancer patient's body utilizing a second peristaltic pump.

9. The method of claim 8, wherein a flow rate of the portion of the bloodstream through each of the first peristaltic pump and the second peristaltic pump is adjusted at a flow rate defined by:

$$\text{Flow rate of bloodstream circulation (ml/min)} = 4 \times \text{Weight of the cancer patient (Kg)}.$$

10. The method of claim 5, wherein placing the electrically conductive element on the fluidic channel comprises placing at least one of an electrical conductive plate and an electrical conductive tape on the fluidic channel.

11. The method of claim 5, wherein placing the electrically conductive element on the fluidic channel comprises:
covering a layer of an electrically conductive material on at least one of an electrical insulator plate and an electrical insulator tape; and
placing the at least one of the electrical insulator plate and the electrical insulator tape with the covered layer of the electrically conductive material thereon on the fluidic channel.

12. The method of claim 3, wherein deactivating CTCs by applying the positive electrostatic field to the bloodstream of the cancer patient comprises:
placing the electrically conductive element over skin of the cancer patient at a location of a superficial vein of the cancer patient;
accumulating positive electrostatic charges on the electrically conductive element by applying the positive electrostatic voltage to the electrically conductive element utilizing the electrostatic charge generator; and
forming deactivated CTCs in the bloodstream of the cancer patient responsive to electrostatically stimulating of CTCs induced by the accumulated positive electrostatic charges.

13. The method of claim 12, wherein placing the electrically conductive element over skin of the cancer patient comprises placing a layer of an electrically conductive material over skin of the cancer patient.

14. The method of claim 13, wherein placing the electrically conductive element over skin of the cancer patient comprises:

forming the electrically conductive element by attaching the layer of the electrically conductive material on a substrate; and placing the formed electrically conductive element over skin of the cancer patient.

15. The method of claim 14, wherein attaching the layer of the electrically conductive material on the substrate comprises attaching the layer of the electrically conductive material on a layer of an electrical insulator material.

16. The method of claim 14, wherein attaching the layer of the electrically conductive material on the substrate comprises attaching a layer of electrically conductive nanostructures on the substrate.

17. The method of claim 16, wherein attaching the layer of electrically conductive nanostructures on the substrate comprises attaching a layer of at least one of carbon nanotubes (CNTs), vertically aligned multi-walled carbon nanotube (VAMWCNTs), graphene, zinc dioxide (ZnO), Silicon nanowires (SiNWs), Silicon nanograss, $TiO_2$ nanotubes, $TiO_2$ nanowires, metallic layers and combinations thereof on the substrate.

18. The method of claim 14, wherein attaching the layer of the electrically conductive material on the substrate comprises attaching the layer of the electrically conductive material on a three-layer substrate, the three-layer substrate comprising:

a layer of silicon (Si);

a layer of silicon dioxide ($SiO_2$) grown on the layer of silicon; and a catalyst layer deposited on the layer of $SiO_2$, the catalyst layer configured to grow the layer of electrically conductive nanostructures thereon.

* * * * *